United States Patent
Kaplan et al.

(10) Patent No.: US 11,298,443 B2
(45) Date of Patent: Apr. 12, 2022

(54) INNERVATED ARTIFICIAL SKIN

(71) Applicant: Trustees of Tufts College, Medford, MA (US)

(72) Inventors: David L. Kaplan, Concord, MA (US); Sarah Lightfoot Vidal, Woburn, MA (US); Rosalyn Abbott, Lynnfield, MA (US); Siwei Zhao, Waltham, MA (US); Dana Cairns, Sommerville, MA (US); Fiorenzo G. Omenetto, Lexington, MA (US)

(73) Assignee: Trustees of Tufts College, Medford, MA (US)

( * ) Notice: Subject to any disclaimer, the term of this patent is extended or adjusted under 35 U.S.C. 154(b) by 438 days.

(21) Appl. No.: 16/314,169

(22) PCT Filed: Jun. 30, 2017

(86) PCT No.: PCT/US2017/040423
§ 371 (c)(1),
(2) Date: Dec. 28, 2018

(87) PCT Pub. No.: WO2018/006037
PCT Pub. Date: Jan. 4, 2018

(65) Prior Publication Data
US 2020/0306415 A1    Oct. 1, 2020

Related U.S. Application Data

(60) Provisional application No. 62/357,775, filed on Jul. 1, 2016.

(51) Int. Cl.
*A61L 27/60* (2006.01)
*A61L 27/22* (2006.01)
(Continued)

(52) U.S. Cl.
CPC ............. *A61L 27/60* (2013.01); *A61L 27/227* (2013.01); *A61L 27/3637* (2013.01);
(Continued)

(58) Field of Classification Search
None
See application file for complete search history.

(56) References Cited

U.S. PATENT DOCUMENTS

| 4,806,355 A | 2/1989 | Goosen et al. |
| 5,015,476 A | 5/1991 | Cochrum et al. |

(Continued)

FOREIGN PATENT DOCUMENTS

| WO | 1997008315 | 3/1997 |
| WO | 2004000915 | 12/2003 |

(Continued)

OTHER PUBLICATIONS

Park et al, International Journal of Biological Macromolecules, 2016, vol. 93, pp. 1567-1574. (Year: 2016).*

(Continued)

*Primary Examiner* — Allison M Fox
(74) *Attorney, Agent, or Firm* — Quarles & Brady, LLP

(57) ABSTRACT

The present invention provides, in some embodiments, multi-layer silk compositions including a first layer comprising silk fibroin and keratinocytes, a second layer comprising silk fibroin and fibroblasts, a third layer comprising silk fibroin and adipocytes, and a plurality of nervous system cells, wherein at least some of the plurality of nervous system cells span at least two layers, and methods of making and using the same. In some embodiments, provided methods and compositions further include immune cells and/or endothelial cells.

20 Claims, 44 Drawing Sheets

SKIN, FAT, NEURONS

SKIN, NEURONS

FAT, NEURONS

SKIN CONTROL

(51) Int. Cl.
*A61L 27/36* (2006.01)
*A61L 27/38* (2006.01)
*C12N 5/071* (2010.01)

(52) U.S. Cl.
CPC ....... *A61L 27/3641* (2013.01); *A61L 27/3813* (2013.01); *A61L 27/3834* (2013.01); *A61L 27/3891* (2013.01); *C12N 5/0698* (2013.01)

(56) References Cited

U.S. PATENT DOCUMENTS

| | | | |
|---|---|---|---|
| 5,093,489 A | 3/1992 | Diamantoglou | |
| 5,245,012 A | 9/1993 | Lombari et al. | |
| 5,263,992 A | 11/1993 | Guire | |
| 5,270,419 A | 12/1993 | Domb | |
| 5,576,881 A | 11/1996 | Doerr et al. | |
| 5,902,800 A | 5/1999 | Green et al. | |
| 6,127,143 A | 10/2000 | Gunasekaran | |
| 6,245,537 B1 | 6/2001 | Williams et al. | |
| 6,267,776 B1 | 7/2001 | O'Connell | |
| 6,302,848 B1 | 10/2001 | Larson et al. | |
| 6,310,188 B1 | 10/2001 | Mukherjee | |
| 6,325,810 B1 | 12/2001 | Hamilton et al. | |
| 6,337,198 B1 | 1/2002 | Levene et al. | |
| 6,372,244 B1 | 4/2002 | Antanavich et al. | |
| 6,379,690 B2 | 4/2002 | Blanchard et al. | |
| 6,387,413 B1 | 5/2002 | Miyata | |
| 6,395,734 B1 | 5/2002 | Tang et al. | |
| 2004/0097709 A1 | 5/2004 | Armato et al. | |
| 2005/0260706 A1 | 11/2005 | Kaplan et al. | |
| 2009/0263430 A1 | 10/2009 | Scheibel et al. | |
| 2010/0017830 A1 | 1/2010 | Burnap | |
| 2011/0171239 A1 | 7/2011 | Kaplan et al. | |
| 2012/0171256 A1 | 7/2012 | Zhang et al. | |
| 2014/0093580 A1 | 4/2014 | Kaplan et al. | |
| 2014/0112973 A1 | 4/2014 | Steinberg | |
| 2017/0296696 A1 | 10/2017 | Kaplan et al. | |

FOREIGN PATENT DOCUMENTS

| | | |
|---|---|---|
| WO | 2005012606 | 2/2005 |
| WO | 2005123114 | 12/2005 |
| WO | 2007016524 | 2/2007 |
| WO | 2008150861 | 12/2008 |
| WO | 2011005381 | 1/2011 |

OTHER PUBLICATIONS

Murphy, L. J. "The role of the insulin-like growth factors and their binding proteins in glucose homeostasis." Journal of Diabetes Research 4.4 (2003): 213-224.

Napolitano, A., et al. "Concentrations of adipsin in blood and rates of adipsin secretion by adipose tissue in humans with normal, elevated and diminished adipose tissue mass." International journal of obesity and related metabolic disorders: journal of the International Association for the Study of Obesity 18.4 (1994): 213-218.

Nazarov, R, et al. "Porous 3-D scaffolds from regenerated silk fibroin." Biomacromolecules 5.3 (2004): 718-726.

Newton, J. P., et al. "CD31 (PECAM-1) exists as a dimer and is heavily N-glycosylated." Biochemical and biophysical research communications 261.2 (1999): 283-291.

Nyame TT, et al. Clinical Applications of Skin Substitutes. Surg Clin North Am 2014; 94: 839-850.

Odegaard, J. I., et al. "Pleiotropic actions of insulin resistance and inflammation in metabolic homeostasis." Science 339.6116 (2013): 172-177.

Partlow et al., Highly tunable elastomeric silk biomaterials, 2014, Adv Funct Mater, 24(29): 4615-4624.

Patrick Jr, C. W. "Tissue engineering strategies for adipose tissue repair." The Anatomical Record: An Official Publication of the American Association of Anatomists 263.4 (2001): 361-366.

Peng, Z, et al. "Tissue engineering chamber promotes adipose tissue regeneration in adipose tissue engineering models through induced aseptic inflammation." Tissue Engineering Part C: Methods 20.11 (2014): 875-885.

Pickup, J. C., et al. "NIDDM as a disease of the innate immune system: association of acute-phase reactants and interleukin-6 with metabolic syndrome X." Diabetologia 40.11 (1997): 1286.

Picone, O., et al. "Hyperlipidic hypercholesterolemic diet in prepubertal rabbits affects gene expression in the embryo, restricts fetal growth and increases offspring susceptibility to obesity." Theriogenology 75.2 (2011): 287-299.

Ramachandra R, et al. NaV1.8 channels are expressed in large, as well as small, diameter sensory afferent neurons. Channels (Austin) 2013; 7: 34-37.

Ray, H., et al. "Depot-specific differences in perilipin and hormone-sensitive lipase expression in lean and obese." Lipids in health and disease 8.1 (2009): 58.

Reisfeld PL. A hard subject: Use of a durometer to assess skin hardness. Journal of the American Academy of Dermatology 1994; 31: 515.

Renehan, A. G., et al. "Obesity and cancer risk: the role of the insulin-IGF axis." Trends in Endocrinology & Metabolism 17.8 (2006): 328-336.

Rockwood DN, et al. Materials fabrication from Bombyx mori silk fibroin. Nat Protoc 2011; 6: 1612-31.

Roggenkamp D, et al. Atopic Keratinocytes Induce Increased Neurite Outgrowth in a Coculture Model of Porcine Dorsal Root Ganglia Neurons and Human Skin Cells. J Invest Dermatol 2012; 132: 1892-1900.

Roggenkamp D, et al. Epidermal nerve fibers modulate keratinocyte growth via neuropeptide signaling in an innervated skin model. J Invest Dermatol 2013; 133: 1620-8.

Roh JD, et al. Tissue-engineered vascular grafts transform into mature blood vessels via an inflammation-mediated process of vascular remodeling. Proceedings of the National Academy of Sciences of the United States of America 2010; 107: 4669-74.

Rollins, B. J., et al. "Recombinant human MCP-1/JE induces chemotaxis, calcium flux, and the respiratory burst in human monocytes." Blood 78.4 (1991): 1112-1116.

Saha, S., et al. "Informing future cartilage repair strategies: a comparative study of three different human cell types for cartilage tissue engineering." Cell and tissue research 352.3 (2013): 495-507.

Samad, F., et al. "Elevated expression of transforming growth factor-ß in adipose tissue from obese mice." Molecular medicine 3.1 (1997): 37-48.

Samad, F., et al. "Tumor necrosis factor a is a key component in the obesity-linked elevation of plasminogen activator inhibitor 1." Proceedings of the National Academy of Sciences 96.12 (1999): 6902-6907.

Sanchez-Infantes, D., et al. "Oncostatin m is produced in adipose tissue and is regulated in conditions of obesity and type 2 diabetes." The Journal of Clinical Endocrinology & Metabolism 99.2 (2014): E217-E225.

Serlachius, M. et al. "Upregulated expression of stanniocalcin-1 during adipogenesis." Experimental cell research 296.2 (2004): 256-264.

Shen, J.-f., et al. "Dedifferentiated fat cells: an alternative source of adult multipotent cells from the adipose tissues." International journal of oral science 3.3 (2011): 117.

Shevchenko R V, et al. A review of tissue-engineered skin bioconstructs available for skin reconstruction. J R Soc Interface 2010; 7: 229-258.

Shulman, G. I. "Cellular mechanisms of insulin resistance." The Journal of clinical investigation 106.2 (2000): 171-176.

Skalli, O., et al. "Alpha-smooth muscle actin, a differentiation marker of smooth muscle cells, is present in microfilamentous bundles of pericytes." Journal of Histochemistry & Cytochemistry 37.3 (1989): 315-321.

Škopková, M., et al. "Protein array reveals differentially expressed proteins in subcutaneous adipose tissue in obesity." Obesity 15.10 (2007): 2396-2406.

Small, C. J., et al. "Chronic CNS administration of Agouti-related protein (Agrp) reduces energy expenditure." International journal of obesity 27.4 (2003): 530.

(56) References Cited

OTHER PUBLICATIONS

Spiller, K.L. et al., 2014. Sequential delivery of immunomodulatory cytokines to facilitate the M1-to-M2 transition of macrophages and enhance vascularization of bone scaffolds. Biomaterials, 37, pp. 194-207.
Strassburg, S., et al. "Human adipose-derived stem cells enhance the angiogenic potential of endothelial progenitor cells, but not of human umbilical vein endothelial cells." Tissue engineering Part A 19.1-2 (2012): 166-174.
Sugihara, H., et al. "Primary cultures of unilocular fat cells: characteristics of growth in vitro and changes in differentiation properties." Differentiation 31.1 (1986): 42-49.
Sugihara, H., et al. "Proliferation of unilocular fat cells in the primary culture." Journal of lipid research 28.9 (1987): 1038-1045.
Sugihara, H., et al. "Unilocular fat cells in three-dimensional collagen gel matrix culture." Journal of lipid research 29.5 (1988): 691-697.
Sun BK, et al. Advances in skin grafting and treatment of cutaneous wounds. Science (80- ) 2015; 346: 941-945.
Sun, T., et al. "Culture of skin cells in 3D rather than 2D improves their ability to survive exposure to cytotoxic agents." Journal of biotechnology 122.3 (2006): 372-381.
Taira, B. R., et al. "Rosiglitazone, a PPAR-? ligand, reduces burn progression in rats." Journal of burn care & research 30.3 (2009): 499-504.
Toda, S., et al. "Adipose tissue-organotypic culture system as a promising model for studying adipose tissue biology and regeneration." Organogenesis 5.2 (2009): 50-56.
Trottier, V., et al. "IFATS collection: Using human adipose-derived stem/stromal cells for the production of new skin substitutes." Stem cells 26.10 (2008): 2713-2723.
Turner, P. A., et al. "Three-dimensional spheroid cell model of in vitro adipocyte inflammation." Tissue Engineering Part A 21.11-12 (2015): 1837-1847.
Turtzo LC, et al. Cross-talk between sympathetic neurons and adipocytes in coculture. Proc Natl Acad Sci U S A 2001; 98: 12385-12390.
Unger, R. H. "Minireview: weapons of lean body mass destruction: the role of ectopic lipids in the metabolic syndrome." Endocrinology 144.12 (2003): 5159-5165.
Van Harmalen, V., et al. "Effect of BMI and age on adipose tissue cellularity and differentiation capacity in women." International journal of obesity 27.8 (2003): 889.
Vancíková, O., et al. "Disappearance of tyrosine residues in collagen with age. Suggestion of a possible reaction mechanism." Experimental gerontology 9.3 (1974): 123-130.
Vermette, M., et al. "Production of a new tissue-engineered adipose substitute from human adipose-derived stromal cells." Biomaterials 28.18 (2007): 2850-2860.
Vistisen, D., et al. "Patterns of obesity development before the diagnosis of type 2 diabetes: the Whitehall II cohort study." PLoS medicine 11.2 (2014): e1001602.
Wajchenberg, B.L. "Subcutaneous and visceral adipose tissue: their relation to the metabolic syndrome." Endocrine reviews 21.6 (2000): 697-738.
Wang, L., et al. "Combining decellularized human adipose tissue extracellular matrix and adipose-derived stem cells for adipose tissue engineering." Acta biomaterialia 9.11 (2013): 8921-8931.
Wang, Y., et al. "In vivo degradation of three-dimensional silk fibroin scaffolds." Biomaterials 29.24-25 (2008): 3415-3428.
Wang, Y., et al. "Pref-1, a preadipocyte secreted factor that inhibits adipogenesis." The Journal of nutrition 136.12 (2006): 2953-2956.
Wang, Y., et al. "Stem cell-based tissue engineering with silk biomaterials." Biomaterials 27.36 (2006): 6064-6082.
Wang, Y.-H., et al. "Characterization and evaluation of the differentiation ability of human adipose-derived stem cells growing in scaffold-free suspension culture." Cytotherapy 16.4 (2014): 485-495.
Ward, A., et al. "Noninvasive metabolic imaging of engineered 3D human adipose tissue in a perfusion bioreactor." PLoS one 8.2 (2013): e55696.
Welss, T., et al. "In vitro skin irritation: facts and future. State of the art review of mechanisms and models." Toxicology in vitro 18.3 (2004): 231-243.
Wisse BE. The inflammatory syndrome: the role of adipose tissue cytokines in metabolic disorders linked to obesity. J Am Soc Nephrol 2004; 15: 2792-800.
Wissink, M. J. B., et al. "Endothelial cell seeding on crosslinked collagen: effects of crosslinking on endothelial cell proliferation and functional parameters." Thrombosis and haemostasis 84.08 (2000): 325-331.
Wittmann, K., et al. "Development of volume-stable adipose tissue constructs using polycaprolactone-based polyurethane scaffolds and fibrin hydrogels." Journal of tissue engineering and regenerative medicine 10.10 (2016): E409-E418.
Wu, I., et al. "An injectable adipose matrix for soft tissue reconstruction." Plastic and reconstructive surgery 129.6 (2012): 1247.
Yamamoto, T., et al. "Lipopolysaccharide signal transduction in oral keratinocytes—involvement of CD59 but not CD14." Cellular signalling 15.9 (2003): 861-869.
Zhang, H. H., et al. "Ceiling culture of mature human adipocytes: use in studies of adipocyte functions." Journal of Endocrinology 164.2 (2000): 119-128.
Zhao S, et al. Bio-functionalized silk hydrogel microfluidic systems. Biomaterials 2016; 93: 60-70.
Zhao, F et al. "Perfusion bioreactor system for human mesenchymal stem cell tissue engineering: dynamic cell seeding and construct development." Biotechnology and bioengineering 91.4 (2005): 482-493.
Zimmermann K, et al. Sensory neuron sodium channel Nav1.8 is essential for pain at low temperatures. Neuroforum 2007; 13: 100-101.
Abbott RD, et al. Strategies for improving the physiological relevance of human engineered tissues. Trends Biotechnol 2015; 33 : 401-407.
Abbott RD, et al. The use of silk as a scaffold for mature, sustainable unilocular adipose 3D tissue engineered systems. Advanced Healthcare Materials 2016; In Press.
Abbott RD, et al. "Long term perfusion system supporting adipogenesis." Methods 84 (2015): 84-89.
Abrahamsson, C. K., et al. "Chondrogenesis and mineralization during in vitro culture of human mesenchymal stem cells on three-dimensional woven scaffolds." Tissue Engineering Part A 16.12 (2010): 3709-3718.
Acharya, C., et al. "Performance evaluation of a silk protein-based matrix for the enzymatic conversion of tyrosine to L-DOPA." Biotechnology Journal: Healthcare Nutrition Technology 3.2 (2008): 226-233.
Altman, A. M., et al. "IFATS collection: human adipose-derived stem cells seeded on a silk fibroin-chitosan scaffold enhance wound repair in a murine soft tissue injury model." Stem cells 27.1 (2009): 250-258.
Altman, G. H., et al. "Silk matrix for tissue engineered anterior cruciate ligaments." Biomaterials 23.20 (2002): 4131-4141.
Altman, G. H., et al. "Silk-based biomaterials." Biomaterials 24.3 (2003): 401-416.
Andrae, J. et al. "Role of platelet-derived growth factors in physiology and medicine." Genes & development 22.10 (2008): 1276-1312.
Arner, P. "Techniques for the measurement of white adipose tissue metabolism: a practical guide." International journal of obesity and related metabolic disorders: journal of the International Association for the Study of Obesity 19.7 (1995): 435-442.
Bayraktar, O, et al. "Silk fibroin as a novel coating material for controlled release of theophylline." European Journal of Pharmaceutics and Biopharmaceutics 60.3 (2005): 373-381.
Bellas, E et al. "Sustainable three-dimensional tissue model of human adipose tissue." Tissue Engineering Part C: Methods 19.10 (2013): 745-754.

(56) References Cited

OTHER PUBLICATIONS

Bellas, E, et al. "In vitro 3D full-thickness skin-equivalent tissue model using silk and collagen biomaterials." Macromolecular bioscience 12.12 (2012): 1627-1636.
Bellas, E, et al. "Sustained volume retention in vivo with adipocyte and lipoaspirate seeded silk scaffolds." Biomaterials 34.12 (2013): 2960-2968.
Bhushan B, et al. Nanomechanical characterization of skin and skin cream. Journal of Microscopy 2010; 240: 135-144.
Blakytny R, et al. The molecular biology of chronic wounds and delayed healing in diabetes. Diabetic Medicine 2006; 23: 594-608.
Bouillon, R, et al. "Vitamin D and energy homeostasis—of mice and men." Nature Reviews Endocrinology 10.2 (2014): 79.
Boulais N, et al. The epidermis: a sensory tissue. European Journal of Dermatology 2008; 18: 119-127.
Cairns D, et al. Expandable and Rapidly Differentiating Human Induced Neural Stem Cell Lines for Multiple Tissue Engineering Applications. Stem Cell Reports 2016; 7: 1-14.
Carlson MW, et al. Three-dimensional tissue models of normal and diseased skin. Current Protocols in Cell Biology 2008; 1-17.
Chang, K-H, et al. "Preparation and characterization of gelatin/hyaluronic acid cryogels for adipose tissue engineering: In vitro and in vivo studies." Acta biomaterialia 9.11 (2013): 9012-9026.
Chen W-N, et al. Roles of ASIC3, TRPV1, and NaV1.8 in the transition from acute to chronic pain in a mouse model of fibromyalgia. Mol Pain 2014; 10:40.
Cheung, H. K., et al. "Composite hydrogel scaffolds incorporating decellularized adipose tissue for soft tissue engineering with adipose-derived stem cells." Biomaterials35.6 (2014): 1914-1923.
Choi, J. H., et al. "Adipogenic differentiation of human adipose-derived stem cells on 3D silk scaffolds." Methods in molecular biology (Clifton, NJ) 702 (2011): 319-330.
Choi, J. H., et al. "Effects of hyperinsulinemia on lipolytic function of three-dimensional adipocyte/endothelial co-cultures." Tissue Engineering Part C: Methods 16.5 (2010): 1157-1165.
Choi, J. H., et al. "Lipolytic function of adipocyte/endothelial cocultures." Tissue Engineering Part A17.9-10 (2011): 1437-1444.
Chu C-C, et al. Harnessing dendritic cells in inflammatory skin diseases. Seminars in immunology 2011; 23: 28-41.
Coppack SW. Pro-inflammatory cytokines and adipose tissue. The Proceedings of the Nutrition Society 2001; 60: 349-56.
Curat, C. A., et al. "Macrophages in human visceral adipose tissue: increased accumulation in obesity and a source of resistin and visfatin." Diabetologia 49.4 (2006): 744.
Danforth Jr, E. "Failure of adipocyte differentiation causes type II diabetes mellitus?." Nature genetics 26.1 (2000): 13.
Demura, M et al. "Immobilization of glucose oxidase with Bombyx mori silk fibroin by only stretching treatment and its application to glucose sensor." Biotechnology and bioengineering 33.5 (1989): 598-603.
Desruisseaux, M. S., et al. "Adipocyte, adipose tissue, and infectious disease." Infection and immunity 75.3 (2007): 1066-1078.
Deyl, Z., et al. "Fluorescence of collagen—properties of tyrosine residues and another fluorescent element in calf skin collagen." FEBS letters 5.3 (1969): 187-191.
Egles, C et al. "Three-dimensional human tissue models of wounded skin." Epidermal Cells. Humana Press, Totowa, NJ, 2010. 345-359.
Eyre, H, et al. "Preventing Cancer, Cardiovascular Disease, and Diabetes: A Common Agenda for the American Cancer Society, the American Diabetes//Association, and the American." Stroke—a Journal of Cerebral Circulation 35.8 (2004): 1999-2010.
Fain, J. N. "Release of interleukins and other inflammatory cytokines by human adipose tissue is enhanced in obesity and primarily due to the nonfat cells." Vitamins & Hormones 74 (2006): 443-477.
Fain, J. N., et al. "Comparison of the release of adipokines by adipose tissue, adipose tissue matrix, and adipocytes from visceral and subcutaneous abdominal adipose tissues of obese humans." Endocrinology 145.5 (2004): 2273-2282.
Falanga V, et al. Use of a durometer to assess skin hardness. J Am Acad Dermatol 1993; 29: 47-51.

Fan, X., et al. "Preparation and characterization of acellular adipose tissue matrix." Zhongguo xiu fu chong jian wai ke za zhi= Zhongguo xiufu chongjian waike zazhi= Chinese journal of reparative and reconstructive surgery 28.3 (2014): 377-383. English Abstract.
Fang, X., et al. "trkA is expressed in nociceptive neurons and influences electrophysiological properties via Nav1. 8 expression in rapidly conducting nociceptors." Journal of Neuroscience 25.19 (2005): 4868-4878.
Fantuzzi, G. "Adipose tissue, adipokines, and inflammation." Journal of Allergy and clinical immunology115.5 (2005): 911-919.
Festuccia, W. T., et al. "PPAR? agonism increases rat adipose tissue lipolysis, expression of glyceride lipases, and the response of lipolysis to hormonal control." Diabetologia 49.10 (2006): 2427-2436.
Frazier, T. P., et al. "Serially transplanted nonpericytic CD146- adipose stromal/stem cells in silk bioscaffolds regenerate adipose tissue in vivo." Stem Cells 34.4 (2016): 1097-1111.
Fredriksson, L., et al. "The PDGF family: four gene products form five dimeric isoforms." Cytokine & growth factor reviews 15.4 (2004): 197-204.
Gao, D., et al. "Interleukin-1ß mediates macrophage-induced impairment of insulin signaling in human primary adipocytes." American Journal of Physiology—Endocrinology and Metabolism 307.3 (2014): E289-E304.
Gerlach, J. C., et al. "Adipogenesis of human adipose-derived stem cells within three-dimensional hollow fiber-based bioreactors." Tissue Engineering Part C: Methods 18.1 (2011): 54-61.
Girandon, L., et al. "In vitro models for adipose tissue engineering with adipose-derived stem cells using different scaffolds of natural origin." Folia Biol (Praha) 57.2 (2011): 47-56.
Grienberger C, et al. Imaging Calcium in Neurons. Neuron 2012; 73: 862-885.
Grzesiak JJ, et al. Enhancement of cell interactions with collagen/glycosaminoglycan matrices by RGD derivatization. Biomaterials 1997; 18: 1625-1632.
Han Y-P, et al. Interleukin-1a-induced proteolytic activation of metalloproteinase-9 by human skin. Surgery 2005; 5: 932-939.
Haskill, S. et al., 1990. Identification of three related human GRO genes encoding cytokine functions. Proceedings of the National Academy of Sciences of the United States of America, 87(October), pp. 7732-7736.
Haug, V., et al. "Comparison between endothelial progenitor cells and human umbilical vein endothelial cells on neovascularization in an adipogenesis mouse model." Microvascular research 97 (2015): 159-166.
Herder, C., et al. "Association of systemic chemokine concentrations with impaired glucose tolerance and type 2 diabetes: results from the Cooperative Health Research in the Region of Augsburg Survey S4 (KORA S4)." Diabetes54.suppl 2 (2005): S11-S17.
Herder, C., et al. "Constitutive and regulated expression and secretion of interferon-?-inducible protein 10 (IP-10/CXCL10) in human adipocytes." International journal of obesity 31.3 (2007): 403.
Hersel U, et al. RGD modified polymers: Biomaterials for stimulated cell adhesion and beyond. Biomaterials 2003; 24: 4385-4415.
Hirsch, J et al. "Methods for the determination of adipose cell size in man and animals." Journal of lipid research 9.1 (1968): 110-119.
Hofmann, S., et al. "Silk fibroin as an organic polymer for controlled drug delivery." Journal of Controlled Release 111.1-2 (2006): 219-227.
Hu, X, et al. "Regulation of silk material structure by temperature-controlled water vapor annealing." Biomacromolecules 12.5 (2011): 1686-1696.
Huang, S.-J., et al. "Adipose-derived stem cells: isolation, characterization, and differentiation potential." Cell transplantation 22.4 (2013): 701-709.
Ibisch, C. et al., 2007. Upregulation of TNF-a Production by IFN-? and LPS in Cultured Canine Keratinocytes: Application to Monosaccharides Effects. Veterinary Research Communications, 31(7), pp. 835-846.
Im, G.-I. "Coculture in musculoskeletal tissue regeneration." Tissue Engineering Part B: Reviews 20.5 (2014): 545-554.
International Searching Authority, International Search Report and Written Opinion, PCT/US2017/040423, dated Jan. 4, 2018, 8 pages.

(56) References Cited

OTHER PUBLICATIONS

Jaikumar, D, et al. "Injectable alginate-O-carboxymethyl chitosan/nano fibrin composite hydrogels for adipose tissue engineering." International journal of biological macromolecules 74 (2015): 318-326.
Jensen LE. Targeting the IL-1 family members in skin inflammation. Current opinion in investigational drugs. 2010; 11: 1211-1220.
Jensen, M. D. "Role of body fat distribution and the metabolic complications of obesity." The Journal of Clinical Endocrinology & Metabolism 93.11_supplement_1 (2008): s57-s63.
Jin, H.-J., et al. "Water-stable silk films with reduced ß-sheet content." Advanced Functional Materials 15.8 (2005): 1241-1247.
Kang, J. H., et al. "In vitro 3D model for human vascularized adipose tissue." Tissue Engineering Part A 15.8 (2009): 2227-2236.
Khan, S., et al. "Role of adipokines and cytokines in obesity-associated breast cancer: therapeutic targets." Cytokine & growth factor reviews 24.6 (2013): 503-513.
Kim, H. J., et al. "Bone tissue engineering with premineralized silk scaffolds." Bone 42.6 (2008): 1226-1234.
Kim, H.-S. "Role of insulin-like growth factor binding protein-3 in glucose and lipid metabolism." Annals of pediatric endocrinology & metabolism 18.1 (2013): 9.
Kim, U.-J., et al. "Three-dimensional aqueous-derived biomaterial scaffolds from silk fibroin." Biomaterials 26.15 (2005): 2775-2785.
Klok, M. D., et al. "The role of leptin and ghrelin in the regulation of food intake and body weight in humans: a review." Obesity reviews 8.1 (2007): 21-34.
Koch, A. E., et al. "Interleukin-8 as a macrophage-derived mediator of angiogenesis." Science 258.5089 (1992): 1798-1801.
Korurer, E., et al. "Production of a composite hyaluronic acid/gelatin blood plasma gel for hydrogel-based adipose tissue engineering applications." Journal of Biomedical Materials Research Part A 102.7 (2014): 2220-2229.
Kuwahara Y, et al. Quantification of hardness, elasticity and viscosity of the skin of patients with systemic sclerosis using a novel sensing device (Vesmeter): A proposal for a new outcome measurement procedure. Rheumatology 2008; 47: 1018-1024.
Lebonvallet N, et al. Effects of the re-innervation of organotypic skin explants on the epidermis. Experimental Dermatology 2012; 21: 156-158.
Lebonvallet N, et al. The evolution and use of skin explants: potential and limitations for dermatological research. European Journal of Dermatology 2010; 20: 671-684.
Li, M., et al. "Study on porous silk fibroin materials. II. Preparation and characteristics of spongy porous silk fibroin materials." Journal of Applied Polymer Science 79.12 (2001): 2192-2199.
Li, S.-L., et al. "Construction of engineering adipose-like tissue in vivo utilizing human insulin gene-modified umbilical cord mesenchymal stromal cells with silk fibroin 3D scaffolds." Journal of tissue engineering and regenerative medicine 9.12 (2015): E267-E275.
Límová M. Active Wound Coverings: Bioengineered Skin and Dermal Substitutes. Surgical Clinics of North America 2010; 90: 1237-1255.
Liu, K., et al. "The dependence of in vivo stable ectopic chondrogenesis by human mesenchymal stem cells on chondrogenic differentiation in vitro." Biomaterials 29.14 (2008): 2183-2192.
Liu, W., et al. "Directing parthenogenetic stem cells differentiate into adipocytes for engineering injectable adipose tissue." Stem cells international 2014 (2014).
Loryman, C. et al., 2008. Inhibition of keratinocyte migration by lipopolysaccharide. Wound Repair and Regeneration, 16(1), pp. 45-51.
Lowes MA, et al. Pathogenesis and therapy of psoriasis. Nature 2007; 445: 866-73.
Lu, S., et al. "Stabilization of enzymes in silk films." Biomacromolecules 10.5 (2009): 1032-1042.
Lucero, HA., et al. "Lysyl oxidase: an oxidative enzyme and effector of cell function." Cellular and Molecular Life Sciences CMLS 63.19-20 (2006): 2304-2316.
Lumeng, C. N., et al. "Inflammatory links between obesity and metabolic disease." The Journal of clinical investigation 121.6 (2011): 2111-2117.
Luo, B., et al. "Porous ovalbumin scaffolds with tunable properties: A resource-efficient biodegradable material for tissue engineering applications." Journal of biomaterials applications 29.6 (2015): 903-911.
MacDougald OA, et al. "Regulated expression of the obese gene product (leptin) in white adipose tissue and 3T3-L1 adipocytes." Proceedings of the National Academy of Sciences 92.20 (1995): 9034-9037.
MacNeil S. Progress and opportunities fortissue-engineered skin. Nature 2007; 445: 874-880.
Maione AG, et al. Three-Dimensional Human Tissue Models That Incorporate Diabetic Foot Ulcer-Derived Fibroblasts Mimic In Vivo Features of Chronic Wounds. Tissue Engineering Part C: Methods 2015; 21: 499-508.
Mathes SH, et al. The use of skin models in drug development. Advanced Drug Delivery Reviews 2014; 69-70: 81-102.
Mauney, J. R., et al. "Engineering adipose-like tissue in vitro and in vivo utilizing human bone marrow and adipose-derived mesenchymal stem cells with silk fibroin 3D scaffolds." Biomaterials 28.35 (2007): 5280-5290.
Meinel, L., et al. "The inflammatory responses to silk films in vitro and in vivo." Biomaterials 26.2 (2005): 147-155.
Metcalfe AD, et al. Tissue engineering of replacement skin: the crossroads of biomaterials, wound healing, embryonic development, stem cells and regeneration. J R Soc Interface 2007; 4: 413-437.
Miller, A. M. "Role of IL-33 in inflammation and disease." Journal of inflammation 8.1 (2011): 22.
Min, S., et al. "Preparation and characterization of crosslinked porous silk fibroin gel." Sen'i Gakkaishi 54.2 (1998): 85-92.
Misery L. Langerhans cells in the neuro-immuno-cutaneous system. J Neuroimmunol 1998; 89: 83-87.
Miyairi, S., et al. "Properties of ß-Glucosidase Immobilized in Serichin Membrane." Journal of fermentation technology 56.4 (1978): 303-308.
Monfort, A. et al. "Strategies for human adipose tissue repair and regeneration." Journal of Cosmetics, Dermatological Sciences and Applications 2.02 (2012): 93.

\* cited by examiner

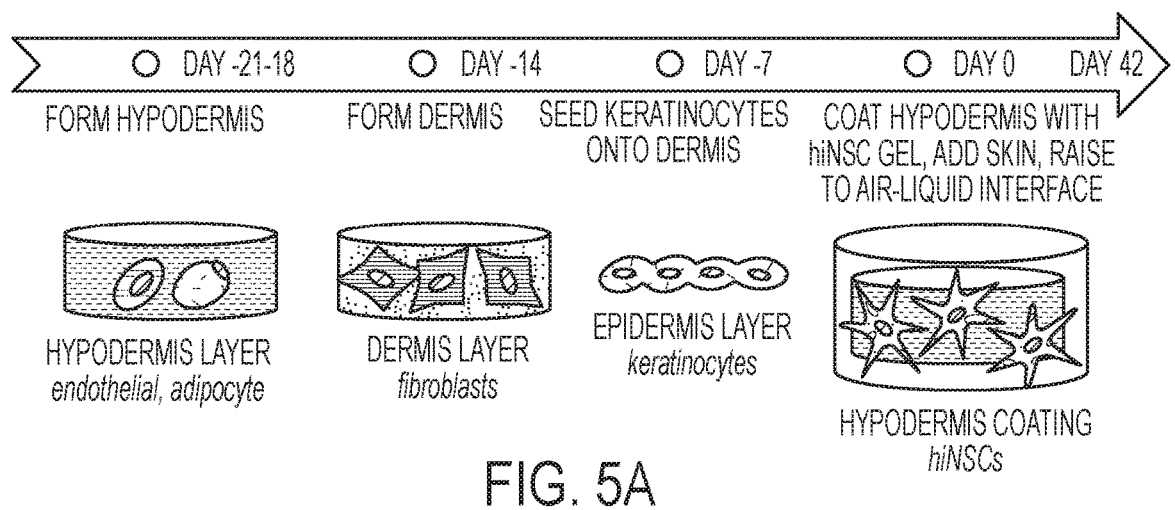
FIG. 5A
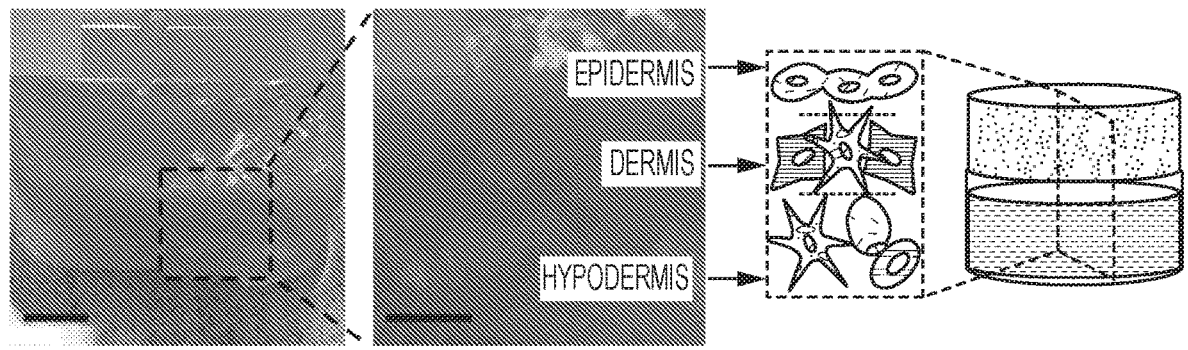
FIG. 5B
FIG. 5C

| SAMPLE | EPIDERMIS | GROUP |
|---|---|---|
| C - COLLAGEN DERMIS | A - WITHOUT KERATINOCYTES | 1 - SKIN CONTROL |
|  |  | 2 - INNERVATED SKIN |
| SC - SILK-COLLAGEN-HRP CROSSLINKED DERMIS | B - WITH KERATINOCYTES | 3 - INNERVATED SKIN WITH HYPODERMIS |
|  |  | 4 - HYPODERMIS CONTROL |

E.G. SCA1 = SILK-COLLAGEN-HRP DERMIS WITHOUT KERATINOCYTES, SKIN CONTROL GROUP

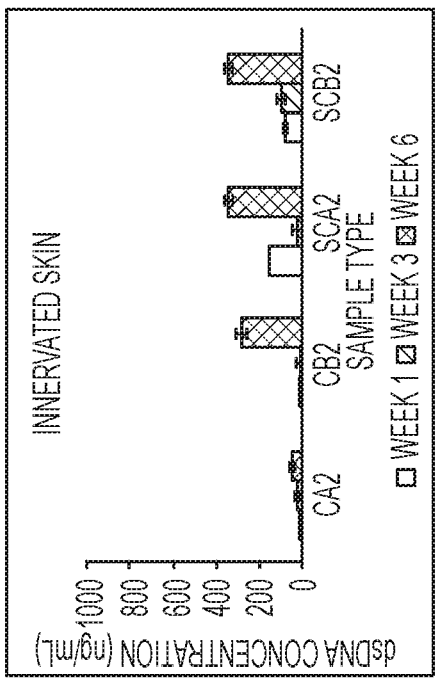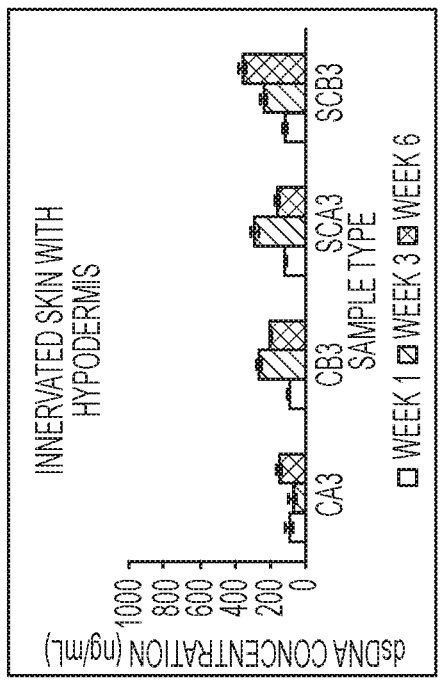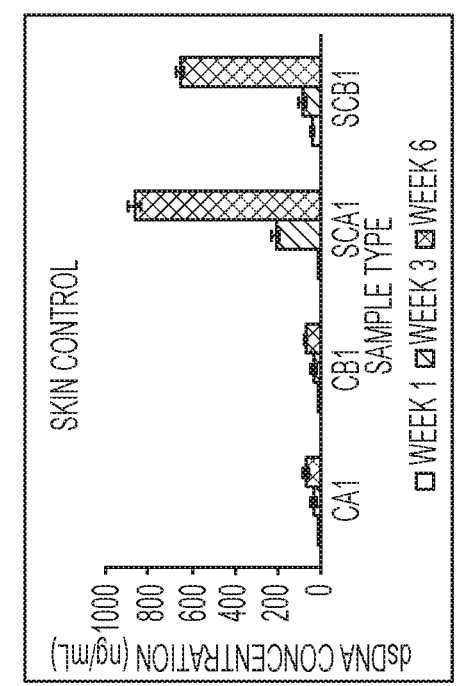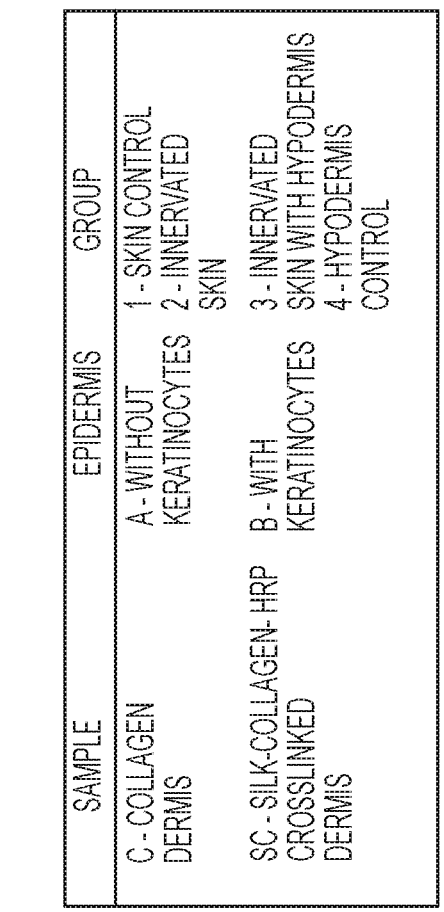
FIG. 22A, FIG. 22B, FIG. 22C

DUROMETER READINGS RECORDED OVER INDEX FINGER PAD IN NORMAL CONTROL SUBJECTS AND IN SCLERODERMA PATIENTS WITH DIFFERENT SKIN SCORES. VALUES ON Y AXIS REPRESENT MEAN ± STANDARD DEVIATION OF QUADRUPLICATE DETERMINATIONS. ☐, NORMAL CONTROL SUBJECTS; ☰, PATIENTS WITH SCLERODERMA.
*TYPE O DUROMETER*

ANALYSIS OF ELECTRICALLY STIMULATED NERVES VIA MULTIELECTRODE ARRAY

INNERVATED ARTIFICIAL SKIN

CROSS-REFERENCE TO RELATED APPLICATIONS

This application represents the national stage entry of PCT/US2017/040423, filed Jun. 30, 2017, which claims benefit of U.S. Provisional Patent Application 62/357,775 filed Jul. 1, 2016. The contents of these applications are hereby incorporated by reference as set forth in their entirety herein.

GOVERNMENT SUPPORT

This invention was made with government support under grant number EB002520 awarded by the National Institutes of Health. The government has certain rights in the invention.

BACKGROUND

Despite extensive knowledge regarding the human skin, the vastly complexity thereof, both in terms of structure and in physiology, has led to only limited success in the development of tissue engineered skin equivalents (HSEs) due to their lack of similarity to human skin. Previously known HSEs lack the structure, cellular and extracellular matrix components of human skin, thus lacking in physiological relevance.

SUMMARY

The present invention provides, among other things, compositions comprising new, powerful human skin equivalents, and methods for making and using such compositions. In particular, provided compositions allow for the creation of multi-layered human skin equivalents including all human cells (e.g. human primary cells), and including innervation across tissue layers. Without wishing to be held to a particular theory, it is contemplated that the inclusion of silk fibroin in provided compositions allows for a degree of mechanical and functional tuning, as well as biocompatibility, not achievable using previously known methods and compositions. In addition, prior to the present invention, there has been no satisfactory HSE which simultaneously addresses the importance of nerve cells while simultaneously including a hypodermis. Thus, in some embodiments, the present invention provides the first HSE to account for the neuro-immuno-cutaneous system using only human cells, and the first to demonstrate innervation of the hypodermis. Further, in some embodiments, this system is also unique in: physiological relevance due to the types of cells and multilayer approach, sustainability for both acute (hours to days) and chronic (weeks to months) studies related to the impact of drugs, disease and other factors on skin functions, pain readout (due to neurological integration), and real time inputs and outputs (due to the electronics integration). In addition, in some embodiments, using a multi layered silk composite gel allows cell cultures to be extended in vitro for longer time frames than previously known compositions which rapidly degrade, thus also allowing studies of chronic disease progression.

In some embodiments, the present invention provides multi-layer silk compositions including a first layer comprising silk fibroin and keratinocytes, a second layer comprising silk fibroin and fibroblasts, a third layer comprising silk fibroin and adipocytes, and a plurality of nervous system cells, wherein at least some of the plurality of nervous system cells span at least two layers.

In some embodiments, the present invention provides methods of making a multi-layer silk compositions including the steps of providing a first layer comprising silk fibroin and keratinocytes, providing a second layer comprising silk fibroin and fibroblasts, providing a third layer comprising silk fibroin and adipocytes, providing a plurality of nervous system cells, and associating the first layer, second layer, third layer, and plurality of nervous system cells to form a multi-layer silk composition, wherein at least some of the plurality of nervous system cells span at least two layers.

In some embodiments, the present invention provides methods including the steps of providing a composition as described herein, wherein at least some of the cells in the composition are cancer cells, exposing the composition to one or more therapeutic agents and/or inflammatory agents, and characterizing the response of the cells in the composition to the one or more therapeutic agents. In some embodiments, the one or more therapeutics agents comprise at least one cancer therapeutic agent. In some embodiments, the inflammatory agents comprise a pro-inflammatory agent. In some embodiments, the inflammatory agents comprise an anti-inflammatory agent. In some embodiments, the one or more inflammatory agents are selected from the group consisting of anti-histamines, antimicrobial agents (e.g., antibacterial, antifungal, and/or antiviral agents), methotrexate, anti-itch agents, oils (e.g., mineral oil, sunflower seed oil, etc), vitamins (e.g., vitamin D), retinoids, capsaicin, salicylic acid, steroids, lipopolysaccharide, allergens, and toxins.

In some embodiments, some, most, or substantially all of the cells in each of the first, second and third layers are human cells. In some embodiments, some, most, or substantially all of the human cells are primary cells or cell lines.

In some embodiments, nervous system cells comprise at least one of neurons, glia, and neural stem cells. In some embodiments, at least a plurality of the nervous system cells are functional.

In some embodiments, provided compositions and methods may further include a plurality of at least one type of immune cells. In some embodiments, the at least one type of immune cells includes macrophages.

In some embodiments, provide methods and compositions may further include a plurality of at least one type of endothelial cell. In some embodiments, the endothelial cells comprise a monolayer. In some embodiments, a monolayer may be in the shape of a tube or portion of a tube.

In some embodiments, provided methods and compositions may further include one or more electrical devices that are functionally connected to at least some of the plurality nervous system cells. In some embodiments, activation of one or more such electrical devices results in the firing of one or more neurons and/or the activation of a plurality of cells in or on the multi-layer silk composition. In some embodiments, the one or more electrical devices are or comprise at least one electrode. In some embodiments, the one or more electrical devices comprise silk fibroin.

In some embodiments, provided methods and compositions may include one or more active agents. In some embodiments, an active agent may be or comprise at least one of collagen, laminin, fibronectin, hyaluronic acid, fibrinogen, sulfated glycosaminoglycans, and/or one or more growth factors. In some embodiments, the one or more growth factors are or comprise epidermal growth factor, fibroblast growth factor, nerve growth factor, platelet-derived growth actor, insulin-like growth factor, or tumor necrosis factor-β, and combinations thereof. In some embodiments at least one active agent may be present in at least one layer of the multi-layer silk composition.

In some embodiments, at least one layer of the multi-layer silk composition is exposed to an air-liquid interface. In some embodiments, an epidermal layer is exposed to an air-liquid interface.

As used in this application, the terms "about" and "approximately" are used as equivalents. Any citations to publications, patents, or patent applications herein are incorporated by reference in their entirety. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The foregoing and other objects, aspects, features, and advantages of the present disclosure will become more apparent and better understood by referring to the following description taken in conjunction with the accompanying figures in which:

FIG. 5a-c shows an exemplary provided method for forming full-thickness innervated skin. 5a shows a timeline of certain provided methods. 5b is silk-collagen three-layered skin, scale is 3.5 mm, 5c is a close up of silk-collagen three-layered skin, scale is 1.75 mm. Images are of formalin-fixed samples after 42 days in culture.

FIG. 22a-c shows double stranded DNA (dsDNA) concentration from certain exemplary embodiments and control conditions. 22a shows exemplary dsDNA concentration from control skin compositions. 22b shows exemplary dsDNA concentration from innervated skin compositions. 22c shows exemplary dsDNA concentration from innervated skin compositions including a hypodermis layer.

FIG. 30 shows, inter alia, methods of electrically stimulating certain provided innervated compositions.

DEFINITIONS

Figure 1:
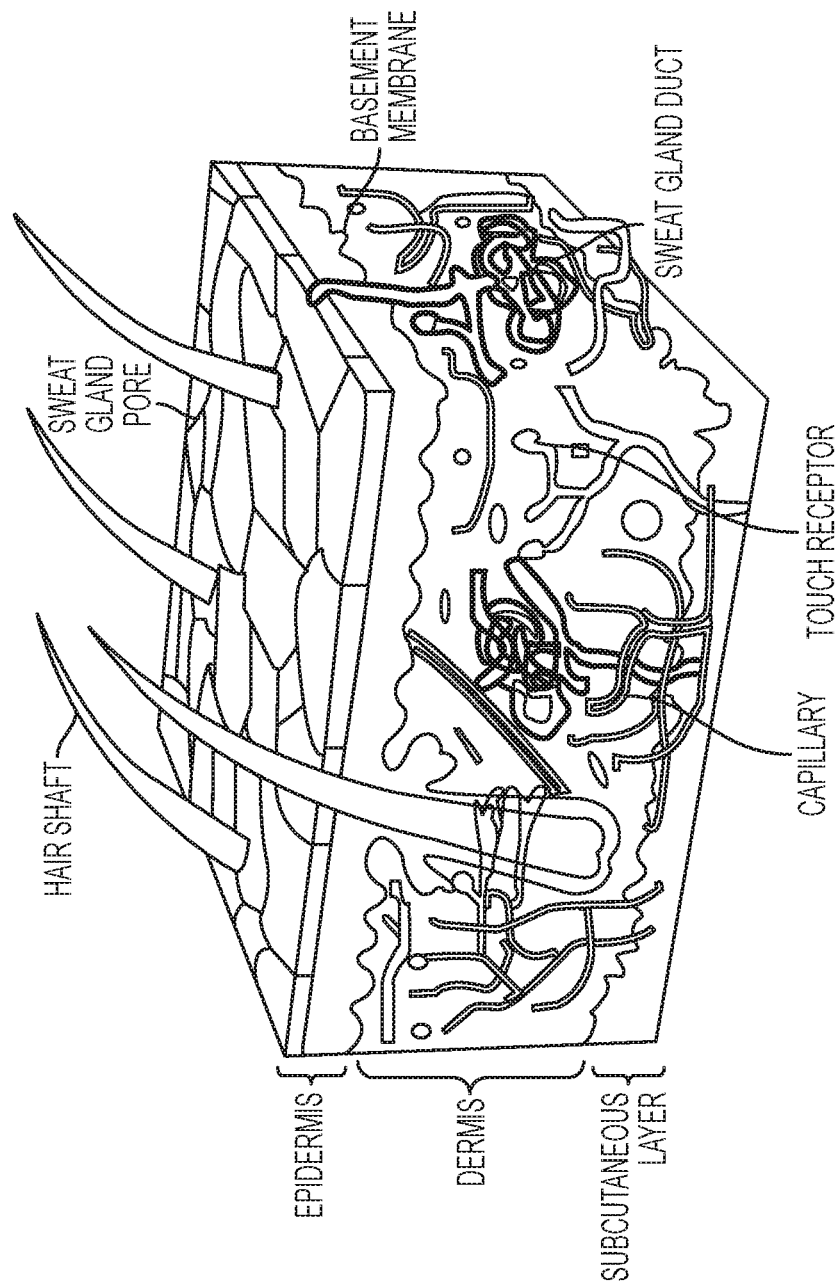
FIG. 1 shows an exemplary cross section of human skin including nerves extending into the epidermis.

In order for the present disclosure to be more readily understood, certain terms are first defined below. Additional definitions for the following terms and other terms are set forth throughout the specification.

In this application, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps. Where ranges are provided herein, the endpoints are included. As used in this application, the term "comprise" and variations of the term, such as "comprising" and "comprises," are not intended to exclude other additives, components, integers or steps.

"About": As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": As used herein, the term "administration" refers to the administration of a composition to a subject. Administration may be by any appropriate route. For example, in some embodiments, administration may be bronchial (including by bronchial instillation), enteral, interdermal, intradermal, intramedullary, intramuscular, intraperitoneal, intrathecal, intravenous, intraventricular, mucosal, nasal, rectal, subcutaneous, topical, transdermal, vaginal and vitreal.

"Amino acid": As used herein, the term "amino acid," in its broadest sense, refers to any compound and/or substance that can be incorporated into a polypeptide chain, e.g., through formation of one or more peptide bonds. In some embodiments, an amino acid has the general structure $H_2N$—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide.

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated entities are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Biocompatible": The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

"Biodegradable": As used herein, the term "biodegradable" refers to materials that, when introduced into cells, are broken down (e.g., by cellular machinery, such as by enzymatic degradation, by hydrolysis, and/or by combinations thereof) into components that cells can either reuse or dispose of without significant toxic effects on the cells. In certain embodiments, components generated by breakdown of a biodegradable material are biocompatible and therefore do not induce significant inflammation and/or other adverse effects in vivo. In some embodiments, biodegradable polymer materials break down into their component monomers. In some embodiments, breakdown of biodegradable materials (including, for example, biodegradable polymer materials) involves hydrolysis of ester bonds. Alternatively or additionally, in some embodiments, breakdown of biodegradable materials (including, for example, biodegradable polymer materials) involves cleavage of urethane linkages. Exemplary biodegradable polymers include, for example, polymers of hydroxy acids such as lactic acid and glycolic acid, including but not limited to poly(hydroxyl acids), poly(lactic acid)(PLA), poly(glycolic acid)(PGA), poly(lactic-co-glycolic acid)(PLGA), and copolymers with PEG, polyanhydrides, poly(ortho)esters, polyesters, polyurethanes, poly(butyric acid), poly(valeric acid), poly(caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

"Comparable": The term "comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

"Conjugated": As used herein, the terms "conjugated," "linked," and "attached," when used with respect to two or more moieties, means that the moieties are physically connected with one another, either directly or via one or more additional moieties that serves as a linking agent, to form a structure that is sufficiently stable so that the moieties remain physically connected under the conditions in which structure is used, e.g., physiological conditions. Typically the moieties are attached either by one or more covalent bonds or by a mechanism that involves specific binding. Alternately, a sufficient number of weaker interactions can provide sufficient stability for moieties to remain physically connected.

"Corresponding to": As used herein, the term "corresponding to" is often used to designate the position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the 190th residue in the first polymer but rather corresponds to the residue found at the 190th position in the reference polymer; those of ordinary skill in the art readily appreciate how to identify "corresponding" amino acids, including through use of one or more commercially-available algorithms specifically designed for polymer sequence comparisons.

"Encapsulated": The term "encapsulated" is used herein to refer to substances that are substantially completely surrounded by another material.

"Functional": As used herein, a "functional" biological molecule is a biological molecule in a form in which it exhibits a property and/or activity by which it is characterized. A biological molecule may have two functions (i.e., bi-functional) or many functions (i.e., multifunctional).

"High Molecular Weight Polymer": As used herein, the term "high molecular weight polymer" refers to polymers and/or polymer solutions comprised of polymers (e.g., protein polymers, such as silk) having molecular weights of at least about 200 kDa, and wherein no more than 30% of the silk fibroin has a molecular weight of less than 100 kDa. In some embodiments, high molecular weight polymers and/or polymer solutions have an average molecular weight of at least about 100 kDa or more, including, e.g., at least about 150 kDa, at least about 200 kDa, at least about 250 kDa, at least about 300 kDa, at least about 350 kDa or more. In some embodiments, high molecular weight polymers have a molecular weight distribution, no more than 50%, for example, including, no more than 40%, no more than 30%, no more than 20%, no more than 10%, of the silk fibroin can have a molecular weight of less than 150 kDa, or less than 125 kDa, or less than 100 kDa.

"Hydrolytically degradable": As used herein, the term "hydrolytically degradable" is used to refer to materials that degrade by hydrolytic cleavage. In some embodiments, hydrolytically degradable materials degrade in water. In some embodiments, hydrolytically degradable materials degrade in water in the absence of any other agents or materials. In some embodiments, hydrolytically degradable materials degrade completely by hydrolytic cleavage, e.g., in water. By contrast, the term "non-hydrolytically degradable" typically refers to materials that do not fully degrade by hydrolytic cleavage and/or in the presence of water (e.g., in the sole presence of water).

"Hydrophilic": As used herein, the term "hydrophilic" and/or "polar" refers to a tendency to mix with, or dissolve easily in, water.

"Hydrophobic": As used herein, the term "hydrophobic" and/or "non-polar", refers to a tendency to repel, not combine with, or an inability to dissolve easily in, water.

"Low Molecular Weight Polymer": As used herein, the term "low molecular weight polymer" refers to polymers and/or polymer solutions, such as silk, comprised of polymers (e.g., protein polymers) having molecular weights within the range of about 3 kDa-about 200 kDa. In some embodiments, low molecular weight polymers (e.g., protein polymers) have molecular weights within a range between a lower bound (e.g., about 10 kDa, about 20 kDa, about 30 kDa, about 40 kDa, about 50 kDa, about 60 kDa, or more) and an upper bound (e.g., about 400 kDa, about 375 kDa, about 350 kDa, about 325 kDa, about 300 kDa, or less). In some embodiments, low molecular weight polymers (e.g., protein polymers such as silk) are substantially free of polymers having a molecular weight above about 200 kD. In some embodiments, the highest molecular weight polymers in provided hydrogels are less than about 100-about 200 kD (e.g., less than about 200 kD, less than about 175 kD, less than about 150 kD, less than about 125 kD, less than about 100 kD, etc). In some embodiments, a low molecular weight polymer and/or polymer solution can comprise a population of polymer fragments having a range of molecular weights, characterized in that: no more than 15% of the total moles of polymer fragments in the population has a molecular weight exceeding 200 kDa, and at least 50% of the total moles of the silk fibroin fragments in the population has a molecular weight within a specified range, wherein the specified range is between about 3 kDa and about 150 kDa, between about 3 kDa and about 140 kDa, between about 3 kDa and about 130 kDa, between about 3 kDa and about 120 kDa or between about 5 kDa and about 125 kDa.

"Nucleic acid": As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 6.8 to about 8.0 and a temperature range of about 20-40 degrees Celsius, about 25-40° C., about 30-40° C., about 35-40° C., about 37° C., and atmospheric pressure of about 1. In some embodiments, physiological conditions utilize or include an aqueous environment (e.g., water, saline, Ringers solution, or other buffered solution); in some such embodiments, the aqueous environment is or comprises a phosphate buffered solution (e.g., phosphate-buffered saline).

"Polypeptide": The term "polypeptide" as used herein, refers to a string of at least three amino acids linked together by peptide bonds. In some embodiments, a polypeptide comprises naturally-occurring amino acids; alternatively or additionally, in some embodiments, a polypeptide comprises one or more non-natural amino acids (i.e., compounds that do not occur in nature but that can be incorporated into a polypeptide chain; see, for example, www.cco.caltech.edu/~dadgrp/Unnatstruct.gif, which displays structures of non-natural amino acids that have been successfully incorporated into functional ion channels) and/or amino acid analogs as are known in the art may alternatively be employed). For example, a polypeptide can be a protein. In some embodiments, one or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc.

"Polysaccharide": The term "polysaccharide" refers to a polymer of sugars. Typically, a polysaccharide comprises at least three sugars. In some embodiments, a polypeptide comprises natural sugars (e.g., glucose, fructose, galactose, mannose, arabinose, ribose, and xylose); alternatively or additionally, in some embodiments, a polypeptide comprises one or more non-natural amino acids (e.g. modified sugars such as 2'-fluororibose, 2'-deoxyribose, and hexose).

"Porosity": The term "porosity" as used herein, refers to a measure of void spaces in a material and is a fraction of volume of voids over the total volume, as a percentage between 0 and 100%. A determination of porosity is known to a skilled artisan using standardized techniques, for example mercury porosimetry and gas adsorption (e.g., nitrogen adsorption).

"Protein": As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

"Small molecule": As used herein, the term "small molecule" is used to refer to molecules, whether naturally-occurring or artificially created (e.g., via chemical synthesis), having a relatively low molecular weight and being an organic and/or inorganic compound. Typically, a "small molecule" is monomeric and have a molecular weight of less than about 1500 g/mol. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.).

"Solution": As used herein, the term "solution" broadly refers to a homogeneous mixture composed of one phase. Typically, a solution comprises a solute or solutes dissolved in a solvent or solvents. It is characterized in that the properties of the mixture (such as concentration, temperature, and density) can be uniformly distributed through the volume. In the context of the present application, therefore, a "silk fibroin solution" refers to silk fibroin protein in a soluble form, dissolved in a solvent, such as water. In some embodiments, silk fibroin solutions may be prepared from a solid-state silk fibroin material (i.e., silk matrices), such as silk films and other scaffolds. Typically, a solid-state silk fibroin material is reconstituted with an aqueous solution, such as water and a buffer, into a silk fibroin solution. It should be noted that liquid mixtures that are not homogeneous, e.g., colloids, suspensions, emulsions, are not considered solutions.

"Stable": The term "stable," when applied to compositions herein, means that the compositions maintain one or more aspects of their physical structure and/or activity over a period of time under a designated set of conditions. In some embodiments, a period of time is at least about one hour; in some embodiments, the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, about thirty-six (36) months, or longer. In some embodiments, the period of time is within the range of about one (1) day to about twenty-four (24) months, about two (2) weeks to about twelve (12) months, about two (2) months to about five (5) months, etc. In some embodiments, the designated conditions are ambient conditions (e.g., at room temperature and ambient pressure). In some embodiments, the designated conditions are physiologic conditions (e.g., in vivo or at about 37° C. for example in serum or in phosphate buffered saline). In some embodiments, the designated conditions are under cold storage (e.g., at or below about 4° C., −20° C., or −70° C.). In some embodiments, the designated conditions are in the dark.

"Substantially": As used herein, the term "substantially", and grammatical equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Sustained release": The term "sustained release" is used herein in accordance with its art-understood meaning of release that occurs over an extended period of time. The extended period of time can be at least about 3 days, about 5 days, about 7 days, about 10 days, about 15 days, about 30 days, about 1 month, about 2 months, about 3 months, about 6 months, or even about 1 year. In some embodiments, sustained release is substantially burst-free. In some embodiments, sustained release involves steady release over the extended period of time, so that the rate of release does not vary over the extended period of time more than about 5%, about 10%, about 15%, about 20%, about 30%, about 40% or about 50%. In some embodiments, sustained release involves release with first-order kinetics. In some embodiments, sustained release involves an initial burst, followed by a period of steady release. In some embodiments, sustained release does not involve an initial burst. In some embodiments, sustained release is substantially burst-free release.

DETAILED DESCRIPTION OF CERTAIN EMBODIMENTS

Prior to the present invention, there has been no acceptable human skin equivalent (HSE) that is suitable for both research and/or commercial use. In part, this is because no previously known HSE was able to replicate the interactions of the nervous system, immune system, and/or endocrine system with the skin. In contrast, as described herein, the present invention, in various embodiments, does provide compositions that are able to replicate and/or substitute for one or more aspects of the so called "neuro-immuno-cutaneous system" including the development of functional innervation across multiple layers (e.g., dermal, epidermal, and/or hypodermal layers). In addition, in accordance with several embodiments, provided compositions comprise all human cells (e.g., human primary cells). Even more, aspect of the present invention may include one or more electrical devices that may be functionally associated with provided compositions.

Skin Anatomy

The skin is composed of three main layers: the epidermis containing keratinocytes, Langerhans cells, Merkel cells, and melanocytes; the dermis containing fibroblasts and macrophages, and the hypodermis which contains adipocytes. Cutaneous nerves located in the epidermis and dermis originate from dorsal root ganglion (DRG) cells located at the spinal cord. The axons of these cells extend into the skin, terminating freely or wrapping around hair follicles or blood vessels.

The skin also contains many functional components including sweat glands, touch receptors and nerve endings, and blood vessels (see FIG. 1, from MacNeil S. Progress and opportunities for tissue-engineered skin. *Nature* 2007; 445: 874-880). Without wishing to be held to a particular theory, it is possible that epidermal cells participate in expression of various sensory proteins and can release certain neuropeptides which allow these cells to purposefully interact with nerve endings in the skin.

Human Skin Equivalents

Despite the knowledge that the human skin is vastly complex both in terms of structure and in physiology, there has been limited success in the development of tissue engineered skin equivalents due to their lack of similarity to human skin including in terms of both functional and/or mechanical properties. Skin models can be used clinically for myriad issues including trauma, chronic wounds and surgeries and in research and development, in vitro models can be used for pharmaceutical development as alternatives to animal testing, disease models (cancer, psoriasis, eczema, etc.), and wound healing. A major limitation of current commercially available HSE models is size, with larger sized wounds being much more difficult to treat with previously known systems and unfortunately these wound dressings, while capable of covering large surface areas, lack the structure, cellular and extracellular matrix (ECM) components and are unable to do much more than prevent infection.

However, a major limitation of previously known HSEs, both clinical and in the research literature, is the lack of complete physiological relevance. Commercially available systems only include two cell types: keratinocytes and fibroblasts, and therefore lack Langerhans, Merkel cells, melanocytes, and macrophages which are all located in the dermis. No commercial model to our knowledge contains adipocytes of the hypodermis. Further, while many 3-dimensional models for skin do exist, they also lack vital components like blood vessels, nerves, and glands. Three-dimensional clinical models are typically composed of bovine collagen sheets or gels containing keratinocytes and fibroblasts (see table 1).

TABLE 1

Summary of current commercially available HSEs.

| Type | Selected method(s) delivery | Components |
|---|---|---|
| Epithelial cover | Integrated sheet (Epicell-Genzyme) Cell spray (CellSpray-Clinical Cell Culture) | Autologous keratinocytes |
| Dermal-only replacements | Donor skin Synthetic material with fibroblasts (Dermagraft-Advanced Biohealing) | Screened donor dermis Donor fibroblasts |
| Epidermal/dermal replacements | Bovine collagen sheet containing cells (Apligraf-Organogenesis) and (Permaderm-Cambrex) | Allogenic (Apligraf) or autologous (Permaderm) keratinocytes and fibroblasts |

Multi-Layer Silk Fibroin Compositions

In contrast to the above attempts, the present invention, in some embodiments, provides functionally innervated HSEs including a hypodermis component/layer. In some embodiments, the present invention provides multi-layer silk compositions including a first layer comprising silk fibroin and keratinocytes, a second layer comprising silk fibroin and fibroblasts, a third layer comprising silk fibroin and adipocytes, and a plurality of nervous system cells, wherein at least some of the plurality of nervous system cells span at least two layers. In some embodiments, provided compositions comprise all or substantially all human cells (e.g., primary human cells). In some embodiments provided compositions include an innervated hypodermal layer. In some embodiments, at least one layer of provided multi-layer silk compositions is exposed to an air-liquid interface.

In some embodiments, provided multi-layer silk compositions may be biocompatible suitable for in vivo use (e.g., as a transplant). In some embodiments, provided compositions may be used in vitro (e.g., to study certain diseases and/or test therapeutic candidates).

In accordance with various embodiments, two or more of the layers of provided multi-layer silk compositions may be associated (e.g., linked, adhered, integrated, etc) via any of a variety of ways. In some embodiments, two or more of the layers of provided multi-layer silk compositions may be associated (e.g., linked, adhered, integrated, etc) via collagen and/or elastic fibers. In some embodiments, two or more of the layers of provided multi-layer silk compositions may be associated (e.g., linked, adhered, integrated) with a fibrin glue. In some embodiments, two or more layers are simply placed one upon the other with no particular adherent or other linking agent. In some embodiments, two or more layers are placed together (e.g., one upon the other) during a gelation process.

Silk Fibroin

Compositions provided herein include compositions comprising a plurality of layers, each containing silk fibroin. Silk fibroin, derived from *Bombyx mori* silkworm cocoons, is a biocompatible material that degrades slowly in the body, is readily modified into a variety of formats, and generates mechanically robust materials.

As used herein, the term "fibroin" includes, but is not limited to, silkworm fibroin and insect or spider silk protein. In some embodiments, fibroin is obtained from a solution containing a dissolved silkworm silk or spider silk. In some embodiments silkworm silk protein is obtained, for example, from *Bombyx mori*, and spider silk is obtained from *Nephila clavipes*. In some embodiments, silk proteins suitable for use in the present invention may be obtained from a solution containing a genetically engineered silk, such as from bacteria, yeast, mammalian cells, transgenic animals or transgenic plants. See, for example, WO 97/08315 and U.S. Pat. No. 5,245,012.

In some embodiments, layers comprising silk fibroin may be made using one or more silk solutions, which are known to be highly customizable and allow for the production of any of a variety of end products. As such, in some embodiments, provided compositions (e.g., multi layered compositions with each layer comprising silk fibroin) may be produced using any of a variety of silk solutions. Preparation of silk fibroin solutions has been described previously, e.g., in WO 2007/016524, which is incorporated herein by reference in its entirety. The reference describes not only the preparation of aqueous silk fibroin solutions, but also such solutions in conjunction with bioactive agents.

In accordance with various embodiments, a silk solution may comprise any of a variety of concentrations of silk fibroin. In some embodiments, a silk solution may comprise 0.1 to 30% by weight silk fibroin. In some embodiments, a silk solution may comprise between about 0.5% and 30% (e.g., 0.5% to 25%, 0.5% to 20%, 0.5% to 15%, 0.5% to 10%, 0.5% to 5%, 0.5% to 1.0%) by weight silk fibroin, inclusive. In some embodiments, a silk solution may comprise at least 0.1% (e.g., at least 0.5%, 1%, 2%, 3%, 4%, 5%, 6%, 7%, 8%, 9%, 10%, 15%, 20%, 25%) by weight silk fibroin. In some embodiments, a silk solution may comprise at most 30% (e.g., at most 25%, 20%, 15%, 14%, 13%, 12% 11%, 10%, 5%, 4%, 3%, 2%, 1%) by weight silk fibroin.

In accordance with various embodiments, the compositions disclosed herein can comprise any amount/ratio of silk fibroin to the total volume/weight of the overall composition (e.g., an individual layer or total multi-layered composition). In some embodiments, the amount of silk fibroin in the solution used for making a provided silk fibroin composition itself can be varied to vary properties of the end silk fibroin composition. By way of specific example, in some embodiments, silk fibroin comprises at least 1% of a provided composition by weight (e.g., at least 2%, 3%, 4%, 5%, 6%, 7%, 8%, 9% 10%, 15%, 20%, 25% or more). In some embodiments, silk fibroin comprises at most 35% of a provided composition by weight (e.g., at most 30%, 25%, 20%, 15%, 10%, 5% or less). In some embodiments, silk fibroin comprises between 1-35% of a provided composition by weight (e.g., between 1-30%, 1-25%, 1-20%, 1-15%, 1-10%, 1-5%, 5-25%, 5-20%, 5-15%, 5-10%).

Silk fibroin solutions used in methods and compositions described herein may be obtained from a solution containing a dissolved silkworm silk, such as, for example, from *Bombyx mori*. Alternatively, a silk fibroin solution is obtained from a solution containing a dissolved spider silk, such as, for example, from *Nephila clavipes*. Silk fibroin solutions can also be obtained from a solution containing a genetically engineered silk. Genetically engineered silk can, for example, comprise a therapeutic agent, e.g., a fusion protein with a cytokine, an enzyme, or any number of hormones or peptide-based drugs, antimicrobials and related substrates.

In accordance with various embodiments, silk used in provided methods and compositions is degummed silk (i.e. silk fibroin with at least a portion of the native sericin removed). Degummed silk can be prepared by any conventional method known to one skilled in the art. For example, *B. mori* cocoons are boiled for a period of pre-determined time in an aqueous solution. Generally, longer degumming time generates lower molecular silk fibroin. In some embodiments, the silk cocoons are boiled for at least 60 minutes, at least 70 minutes, at least 80 minutes, at least 90 minutes, at least 100 minutes, at least 110 minutes, at least 120 minutes, or longer. Additionally or alternatively, in some embodiments, silk cocoons can be heated or boiled at an elevated temperature. For example, in some embodiments, silk cocoons can be heated or boiled at about 100° C., 101.0° C., at about 101.5° C., at about 102.0° C., at about 102.5° C., at about 103.0° C., at about 103.5° C., at about 104.0° C., at about 104.5° C., at about 105.0° C., at about 105.5° C., at about 106.0° C., at about 106.5° C., at about 107.0° C., at about 107.5° C., at about 108.0° C., at about 108.5° C., at about 109.0° C., at about 109.5° C., at about 110.0° C., at about 110.5° C., at about 111.0° C., at about 111.5° C., at about 112.0° C., at about 112.5° C., at about 113.0° C., 113.5° C., at about 114.0° C., at about 114.5° C., at about 115.0° C., at about 115.5° C., at about 116.0° C., at about 116.5° C., at about 117.0° C., at about 117.5° C., at about 118.0° C., at about 118.5° C., at about 119.0° C., at about 119.5° C., at about 120.0° C., or higher. In some embodiments, such elevated temperature can be achieved by carrying out at least portion of the heating process (e.g., boiling process) under pressure. For example, suitable pressure under which silk fibroin fragments described herein can be produced are typically between about 10-40 psi, e.g., about 11 psi, about 12 psi, about 13 psi, about 14 psi, about 15 psi, about 16 psi, about 17 psi, about 18 psi, about 19 psi, about 20 psi, about 21 psi, about 22 psi, about 23 psi, about 24 psi, about 25 psi, about 26 psi, about 27 psi, about 28 psi, about 29 psi, about 30 psi, about 31 psi, about 32 psi, about 33 psi, about 34 psi, about 35 psi, about 36 psi, about 37 psi, about 38 psi, about 39 psi, or about 40 psi.

In some embodiments, the aqueous solution used in the process of degumming silk cocoons comprises about 0.02M $Na_2CO_3$. The cocoons are rinsed, for example, with water to extract the sericin proteins. The degummed silk can be dried and used for preparing silk powder. Alternatively, the extracted silk can dissolved in an aqueous salt solution. Salts useful for this purpose include lithium bromide, lithium thiocyanate, calcium nitrate or other chemicals capable of solubilizing silk. In some embodiments, the extracted silk can be dissolved in about 8M-12 M LiBr solution. The salt is consequently removed using, for example, dialysis.

In some embodiments, the silk fibroin is substantially depleted of its native sericin content (e.g., 5% (w/w) or less residual sericin in the final extracted silk). In some embodiments, the silk fibroin is entirely free of its native sericin content. As used herein, the term "entirely free" (i.e. "consisting of" terminology) means that within the detection range of the instrument or process being used, the substance cannot be detected or its presence cannot be confirmed. In some embodiments, the silk fibroin is essentially free of its native sericin content. As used herein, the term "essentially free" (or "consisting essentially of") means that only trace amounts of the substance can be detected, is present in an amount that is below detection, or is absent.

If necessary, the solution can then be concentrated using, for example, dialysis against a hygroscopic polymer, for example, PEG, a polyethylene oxide, amylose or sericin. In some embodiments, the PEG is of a molecular weight of 8,000-10,000 g/mol and has a concentration of about 10% to about 50% (w/v). A slide-a-lyzer dialysis cassette (Pierce, MW CO 3500) can be used. However, any dialysis system can be used. The dialysis can be performed for a time period sufficient to result in a final concentration of aqueous silk solution between about 10% to about 30%. In most cases dialysis for 2-12 hours can be sufficient. See, for example, International Patent Application Publication No. WO 2005/

012606, the content of which is incorporated herein by reference in its entirety. Another method to generate a concentrated silk solution comprises drying a dilute silk solution (e.g., through evaporation or lyophilization). The dilute solution can be dried partially to reduce the volume thereby increasing the silk concentration. The dilute solution can be dried completely and then dissolving the dried silk fibroin in a smaller volume of solvent compared to that of the dilute silk solution. In some embodiments, a silk fibroin solution can optionally, at a suitable point, be filtered and/or centrifuged. For example, in some embodiments, a silk fibroin solution can optionally be filtered and/or centrifuged following the heating or boiling step. In some embodiments, a silk fibroin solution can optionally be filtered and/or centrifuged following the dialysis step. In some embodiments, a silk fibroin solution can optionally be filtered and/or centrifuged following the step of adjusting concentrations. In some embodiments, a silk fibroin solution can optionally be filtered and/or centrifuged following the step of reconstitution. In any of such embodiments, the filtration and/or centrifugation step(s) can be carried out to remove insoluble materials. In any of such embodiments, the filtration and/or centrifugation step(s) can be carried out to selectively enrich silk fibroin fragments of certain molecular weight(s).

In some embodiments, provided silk compositions described herein (including individual layers), and methods of making and/or using them may be performed in the absence of any organic solvent. Thus, in some embodiments, provided compositions and methods are particularly amenable to the incorporation of labile molecules, such as bioactive agents or therapeutics, and can, in certain embodiments, be used to produce controlled release biomaterials. In some embodiments, such methods are performed in water only.

In some embodiments, the silk fibroin solution can be produced using organic solvents. Such methods have been described, for example, in Li, M., et al., *J. Appl. Poly Sci.* 2001, 79, 2192-2199; Min, S., et al. *Sen'I Gakkaishi* 1997, 54, 85-92; Nazarov, R. et al., *Biomacromolecules* 2004 5, 718-26, contents of all which are incorporated herein by reference in their entireties. An exemplary organic solvent that can be used to produce a silk solution includes, but is not limited to, hexafluoroisopropanol (HFIP). See, for example, International Application No. WO2004/000915, content of which is incorporated herein by reference in its entirety. In some embodiments, the silk solution is entirely free or essentially free of organic solvents, e.g., solvents other than water.

In some embodiments, biocompatible polymers can also be added to a silk solution to generate composite materials in the methods and processes of the present invention. Exemplary biocompatible polymers useful in some embodiments of the present invention include, for example, polyethylene oxide (PEO) (U.S. Pat. No. 6,302,848), polyethylene glycol (PEG) (U.S. Pat. No. 6,395,734), collagen (U.S. Pat. No. 6,127,143), fibronectin (U.S. Pat. No. 5,263,992), keratin (U.S. Pat. No. 6,379,690), polyaspartic acid (U.S. Pat. No. 5,015,476), polylysine (U.S. Pat. No. 4,806,355), alginate (U.S. Pat. No. 6,372,244), chitosan (U.S. Pat. No. 6,310,188), chitin (U.S. Pat. No. 5,093,489), hyaluronic acid (U.S. Pat. No. 387,413), pectin (U.S. Pat. No. 6,325,810), polycaprolactone (U.S. Pat. No. 6,337,198), polylactic acid (U.S. Pat. No. 6,267,776), polyglycolic acid (U.S. Pat. No. 5,576,881), polyhydroxyalkanoates (U.S. Pat. No. 6,245,537), dextrans (U.S. Pat. No. 5,902,800), and polyanhydrides (U.S. Pat. No. 5,270,419). In some embodiments, two or more biocompatible polymers can be used.

Various embodiments may comprise one or more layers which comprise a three dimensional silk membrane/film comprising pores of various sizes (i.e., porous silk membrane/). In some embodiments, pores in a three dimensional silk membrane have a diameter between about 1-1,000 µm, (e.g., between about 1-100, 20-100, 30-100, 40-100, 50-100, 60-100, 70-100, 80-100, 90-100, 50-1,000, 100-1,000, 200-1,000, 300-1,000, 400-1,000, 500-1,000, 600-1,000, 700-1,000, 800-1,000, or 900-1,000 µm) inclusive. In some embodiments, pores in a three dimensional silk membrane have a diameter between about 500-1,000 µm, inclusive. In some embodiments, pores in a three dimensional silk membrane have a diameter between about 500-600 µm, inclusive.

In some embodiments, silk layers may be made porous through the use of one or more porogens. It is contemplated that any known porogen may be suitable for use according to various embodiments. In some embodiments, a porogen may be or comprise crystals (e.g., sodium chloride crystals), micro- and/or nano-spheres, polymers (such as polyethylene oxide, or PEO), ice crystals, and/or a laser. In some embodiments a porogen may comprise mechanical introduction of pores (e.g., using a needle or other article or device to pierce a layer one or more times, or using stress to introduce one or more tears in a layer).

In accordance with various embodiments, provided silk-containing layers (e.g., porous silk layers) may be of a variety of different thicknesses. In some embodiments, a silk layer is less than or equal to 100 cm thick. In some embodiments, a silk layer is between 0.1 and 100 cm thick (e.g., 0.2-100, 0.5-10, 0.2-9, 0.2-8, 0.2-7, 0.2-6, 0.2-5, 0.2-4, 0.2-3, 0.2-2, 0.2-1, 0.5-1, 0.2-0.9, 0.2-0.8, 0.2-0.7, 0.2-0.6, 0.2-0.5, 0.2-0.4, 0.2-0.3 cm thick). In some embodiments, a silk layer is about 0.2-0.5 cm thick, inclusive. In some embodiments, a silk layer is of a substantially uniform thickness. In some embodiments, a silk layer varies in thickness across a particular length (e.g., a 1 cm, 5 cm, 10 cm, 15 cm, 20 cm, 22 cm, etc).

In some embodiments, one or more layers (and/or silk solutions from which a layer is made) may comprise, for example, low molecular weight silk fibroin fragments (e.g., fragments of silk fibroin between 3 kDa and 200 kDa), though any molecular weight silk may be used in accordance with various embodiments. In any of the embodiments described herein, silk fibroin fragments can include one or more mutations and/or modifications, relative to a naturally occurring (e.g., wild type) sequence of silk fibroin. Such mutation and/or modification in the silk fibroin fragment can be spontaneously occurring or introduced by design. For example, in some embodiments, such mutation and/or modification in the silk fibroin fragment can be introduced using recombinant techniques, chemical modifications, etc.

Silk—Conformational Changes

In some embodiments, a conformational change can be induced in the silk fibroin to control the solubility of the silk fibroin composition. In some embodiments, the conformational change can induce the silk fibroin to become at least partially insoluble. Without wishing to be bound by a theory, an induced conformational change may alter the crystallinity of the silk fibroin, e.g., Silk II beta-sheet crystallinity. In accordance with various embodiments, the conformational change can be induced by any methods known in the art, including, but not limited to, alcohol immersion (e.g., ethanol, methanol), water annealing, shear stress, ultrasound (e.g., by sonication), pH reduction (e.g., pH titration and/or exposure to an electric field) and any combinations thereof. For example, the conformational change can be induced by one or more methods, including but not limited to, controlled slow drying (Lu et al., Biomacromolecules 2009, 10, 1032); water annealing (Jin et al., 15 Adv. Funct. Mats. 2005, 15, 1241; Hu et al., Biomacromolecules 2011, 12, 1686); stretching (Demura & Asakura, Biotech & Bioengin. 1989, 33, 598); compressing; solvent immersion, including methanol (Hofmann et al., J Control Release. 2006, 111, 219), ethanol (Miyairi et al., J. Fermen. Tech. 1978, 56, 303), glutaraldehyde (Acharya et al., Biotechnol J. 2008, 3, 226), and 1-ethyl-3-(3-dimethyl aminopropyl) carbodiimide (EDC) (Bayraktar et al., Eur J Pharm Biopharm. 2005, 60, 373); pH adjustment, e.g., pH titration and/or exposure to an electric field (see, e.g., U.S. Patent App. No. US2011/0171239); heat treatment; shear stress (see, e.g., International App. No.: WO 2011/005381), ultrasound, e.g., sonication (see, e.g., U.S. Patent Application Publication No. U.S. 2010/0178304 and International App. No. WO2008/150861); and any combinations thereof. Contents of all of the references listed above are incorporated herein by reference in their entireties.

In some embodiments, the conformation of the silk fibroin can be altered by water annealing. Without wishing to be bound by a theory, it is believed that physical temperature-controlled water vapor annealing (TCWVA) provides a simple and effective method to obtain refined control of the molecular structure of silk biomaterials. The silk materials can be prepared with control of crystallinity, from a low beta-sheet content using conditions at 4° C. (α helix dominated silk I structure), to higher beta-sheet content of ~60% crystallinity at 100° C. (β-sheet dominated silk II structure). This physical approach covers the range of structures previously reported to govern crystallization during the fabrication of silk materials, yet offers a simpler, green chemistry, approach with tight control of reproducibility. Water or water vapor annealing is described, for example, in PCT application no. PCT/US2004/011199, filed Apr. 12, 2004 and no. PCT/US2005/020844, filed Jun. 13, 2005; and Jin et al., Adv. Funct. Mats. 2005, 15: 1241 and Hu et al., Biomacromolecules, 2011, 12(5): 1686-1696, contents of all of which are incorporated herein by reference in their entireties In some embodiments, alteration in the conformation of the silk fibroin can be induced by immersing in alcohol, e.g., methanol, ethanol, etc. The alcohol concentration can be at least 10%, at least 20%, at least 30%, at least 40%, at least 50%, at least 60%, at least 70%, at least 80%, at least 90% or 100%. In some embodiment, alcohol concentration is 100%. If the alteration in the conformation is by immersing in a solvent, the silk composition can be washed, e.g., with solvent/water gradient to remove any of the residual solvent that is used for the immersion. The washing can be repeated one, e.g., one, two, three, four, five, or more times.

Alternatively, the alteration in the conformation of the silk fibroin can be induced with shear stress. The shear stress can be applied, for example, by passing the silk composition through a needle. Other methods of inducing conformational changes include applying an electric field, applying pressure, or changing the salt concentration.

In some embodiments, alteration in the conformation of the silk fibroin can be induced by horseradish peroxidase (HRP) and hydrogen peroxide ($H_2O_2$). As is known in the art, HRP facilitates crosslinking of the tyrosines in silk fibroin via the formation of free radical species in the presence of hydrogen peroxide. Exemplary methods may be found in Partlow et al., Highly tunable elastomeric silk biomaterials, 2014, Adv Funct Mater, 24(29): 4615-4624.

The treatment time for inducing the conformational change can be any period of time to provide a desired silk II (beta-sheet crystallinity) content. In some embodiments, the treatment time can range from about 1 hour to about 12 hours, from about 1 hour to about 6 hours, from about 1 hour to about 5 hours, from about 1 hour to about 4 hours, or from about 1 hour to about 3 hours. In some embodiments, the sintering time can range from about 2 hours to about 4 hours or from 2.5 hours to about 3.5 hours.

When inducing the conformational change is by solvent immersion, treatment time can range from minutes to hours. For example, immersion in the solvent can be for a period of at least about 15 minutes, at least about 30 minutes, at least about 1 hour, at least about 2 hours, at least 3 hours, at least about 6 hours, at least about 18 hours, at least about 12 hours, at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, or at least about 14 days. In some embodiments, immersion in the solvent can be for a period of about 12 hours to about seven days, about 1 day to about 6 days, about 2 to about 5 days, or about 3 to about 4 days.

After the treatment to induce the conformational change, silk fibroin can comprise a silk II beta-sheet crystallinity content of at least about 5%, at least about 10%, at least about 20%, at least about 30%, at least about 40%, at least about 50%, at least about 60%, at least about 70%, at least about 80%, at least about 90%, or at least about 95% but not 100% (i.e., all the silk is present in a silk II beta-sheet conformation). In some embodiments, silk is present completely in a silk II beta-sheet conformation, i.e., 100% silk II beta-sheet crystallinity.

In some embodiments, the silk fibroin may comprise a protein structure that substantially includes β-turn and β-strand regions. Without wishing to be bound by a theory, the silk β sheet content can impact gel function and in vivo longevity of the composition. It is to be understood that composition including non-β sheet content (e.g., e-gels) can also be utilized. In some embodiments, the silk fibroin has a protein structure including, e.g., about 5% β-turn and β-strand regions, about 10% β-turn and β-strand regions, about 20% β-turn and β-strand regions, about 30% β-turn and β-strand regions, about 40% β-turn and β-strand regions, about 50% β-turn and β-strand regions, about 60% β-turn and β-strand regions, about 70% β-turn and β-strand regions, about 80% β-turn and β-strand regions, about 90% β-turn and β-strand regions, or about 100% β-turn and β-strand regions. In other aspects of these embodiments, the silk fibroin has a protein structure including, e.g., at least 10% β-turn and β-strand regions, at least 20% β-turn and β-strand regions, at least 30% β-turn and β-strand regions, at least 40% β-turn and β-strand regions, at least 50% β-turn and β-strand regions, at least 60% β-turn and β-strand regions, at least 70% β-turn and β-strand regions, at least 80% β-turn and β-strand regions, at least 90% β-turn and β-strand regions, or at least 95% β-turn and β-strand regions. In yet other aspects of these embodiments, the silk fibroin has a protein structure including, e.g., about 10% to about 30% β-turn and β-strand regions, about 20% to about 40% β-turn and β-strand regions, about 30% to about 50% β-turn and β-strand regions, about 40% to about 60% β-turn and β-strand regions, about 50% to about 70% β-turn and β-strand regions, about 60% to about 80% β-turn and β-strand regions, about 70% to about 90% β-turn and β-strand regions, about 80% to about 100% β-turn and β-strand regions, about 10% to about 40% β-turn and β-strand regions, about 30% to about 60% β-turn and β-strand regions, about 50% to about 80% β-turn and β-strand regions, about 70% to about 100% β-turn and β-strand regions, about 40% to about 80% β-turn and β-strand regions, about 50% to about 90% β-turn and β-strand regions, about 60% to about 100% β-turn and β-strand regions, or about 50% to about 100% β-turn and β-strand regions. In some embodiments, silk β sheet content, from less than 10% to ~55% can be used in the silk fibroin compositions disclosed herein.

In some embodiments, the silk fibroin has a protein structure that is substantially-free of α-helix and random coil regions. In aspects of these embodiments, the silk fibroin has a protein structure including, e.g., about 5% α-helix and random coil regions, about 10% α-helix and random coil regions, about 15% α-helix and random coil regions, about 20% α-helix and random coil regions, about 25% α-helix and random coil regions, about 30% α-helix and random coil regions, about 35% α-helix and random coil regions, about 40% α-helix and random coil regions, about 45% α-helix and random coil regions, or about 50% α-helix and random coil regions. In other aspects of these embodiments, the silk fibroin has a protein structure including, e.g., at most 5% α-helix and random coil regions, at most 10% α-helix and random coil regions, at most 15% α-helix and random coil regions, at most 20% α-helix and random coil regions, at most 25% α-helix and random coil regions, at most 30% α-helix and random coil regions, at most 35% α-helix and random coil regions, at most 40% α-helix and random coil regions, at most 45% α-helix and random coil regions, or at most 50% α-helix and random coil regions. In yet other aspects of these embodiments, the silk fibroin has a protein structure including, e.g., about 5% to about 10% α-helix and random coil regions, about 5% to about 15% α-helix and random coil regions, about 5% to about 20% α-helix and random coil regions, about 5% to about 25% α-helix and random coil regions, about 5% to about 30% α-helix and random coil regions, about 5% to about 40% α-helix and random coil regions, about 5% to about 50% α-helix and random coil regions, about 10% to about 20% α-helix and random coil regions, about 10% to about 30% α-helix and random coil regions, about 15% to about 25% α-helix and random coil regions, about 15% to about 30% α-helix and random coil regions, or about 15% to about 35% α-helix and random coil regions.

Epidermal Layers

The epidermis is the outer of the two layers that make up the skin (or cutis), with the inner layer being the dermis (discussed below). The epidermis, among other things, provides a barrier to infection from environmental pathogens and regulates the amount of water released from the body into the atmosphere through transepidermal water loss (TEWL). The outermost part of the epidermis is composed of a stratified layer of flattened cells, that overlie a basal layer (stratum basale) composed of columnar cells arranged perpendicularly.

Provided compositions and methods include at least one epidermal layer. In some embodiments, an epidermal layer may be or comprise silk fibroin and a plurality of keratinocytes. In some embodiments, an epidermal layer may be or comprise silk fibroin, a biocompatible protein, and a plurality of keratinocytes. In some embodiments, a biocompatible protein may be selected from collagen, laminin, fibronectin, hyaluronic acid, fibrinogen, sulfated glycosaminoglycans or other extracellular matrix components or other biocompatible polymers. In some embodiments, an epidermal layer may be or comprise silk fibroin, collagen, and a plurality of keratinocytes. Herein, an epidermal layer may be referred to as a "first" layer. In some embodiments, at least one epidermal layer is exposed to an air-liquid interface.

Dermal Layers

The dermis is a layer of skin between the epidermis and subcutaneous tissues, that primarily consists of dense irregular connective tissue and cushions the body from stress and strain. Generally, it is divided into two layers, a superficial area adjacent to the epidermis called the papillary region and a deep thicker area known as the reticular dermis. The dermis is tightly connected to the epidermis through a basement membrane. Structural components of the dermis include collagen, elastic fibers, and extrafibrillar matrix. The dermis also contains mechanoreceptors that provide the sense of touch and thermoreceptors that provide the sense of heat. In addition, hair follicles, sweat glands, sebaceous glands, apocrine glands, lymphatic vessels and blood vessels are present in the native dermis. Those blood vessels provide nourishment and waste removal for both dermal and epidermal cells.

Provided compositions and methods include at least one dermal layer. In some embodiments, a dermal layer may be or comprise silk fibroin and a plurality of fibroblasts. In some embodiments, an dermal layer may be or comprise silk fibroin, a biocompatible protein, and a plurality of fibroblasts. In some embodiments, a biocompatible protein may be selected from collagen, laminin, fibronectin, hyaluronic acid, fibrinogen, sulfated glycosaminoglycans or other extracellular matrix components or other biocompatible polymers. In some embodiments, a dermal layer may be or comprise silk fibroin, collagen, and a plurality of fibroblasts. Herein, a dermal layer may be referred to as a "second" layer. In some embodiments, a crosslinking agent (e.g., horseradish peroxidase or HRP, hydrogen peroxide) may be used to crosslink at least a portion of a dermal layer. In some embodiments, a dermal layer may further comprise nerve cells and/or immune cells, including those as further described below. In some embodiments, nerves present in the dermal layer originate from outside of the dermal layer.

Hypodermal Layers

The hypodermis is the innermost and thickest layer of the skin. The hypodermis is attached to the dermis by collagen and elastin fibers. The hypodermis is essentially composed of a type of cells specialized in accumulating and storing fats, known as adipocytes. These cells are grouped together in lobules separated by connective tissue. In general, the hypodermis acts as an energy reserve, with fats contained in the adipocytes able to be put back into circulation, via the venous route, during intense effort or when there is a lack of energy providing substances, and are then transformed into energy. The hypodermis participates, passively at least, in thermoregulation since fat is a heat insulator.

Provided compositions and methods include at least one hypodermal layer. In some embodiments, a hypodermal layer may be or comprise silk fibroin and a plurality of adipocytes. In some embodiments, an hypodermal layer may be or comprise silk fibroin, a biocompatible protein, and a plurality of adipocytes. In some embodiments, a biocompatible protein may be selected from collagen, laminin, fibronectin, hyaluronic acid, fibrinogen, sulfated glycosaminoglycans or other extracellular matrix components or other biocompatible polymers. In some embodiments, a hypodermal layer may be or comprise silk fibroin, collagen, and a plurality of adipocytes. Herein, a hypodermal layer may be referred to as a "third" layer. In some embodiments, a hypodermal layer may be created by applying a liquefied adipose tissue directly onto a silk fibroin composition (e.g., a silk fibroin composition including epidermal and dermal layers).

Nervous System Cells

In some embodiments, provided methods and compositions include a plurality of at least one type of nervous system cells. In some embodiments, nervous system cells comprise at least one of neurons, glia, and neural stem cells. In some embodiments, at least a plurality of the nervous system cells are functional. In some embodiments, substantially all of the nervous system cells are functional (e.g., capable of firing a plurality of action potentials or differentiating into one or more cell types). In some embodiments, at least some of the plurality of nervous system cells are present in at least two layers. In some embodiments, at least some of the plurality of nervous system cells are present across at least two layers, for example, with the cell body in one layer and the axon spanning a second layer. In some embodiments, at least some of the plurality of nervous system cells are present in a gel or hydrogel.

In some embodiments, the function of at least some of the plurality of nervous system cells may be assessed via any known method. For example, in some embodiments, the function of at least some of the plurality of nervous system cells may be assessed via real time calcium imaging, magnetic resonance imaging, assays of metabolic function including neurotransmitter production, etc.

In some embodiments, at least some of the plurality of nervous system cells may be at least partially myelinated. In some embodiments, at least some of the plurality of nervous system cells may be fully myelinated (e.g., with a pattern of myelination substantially similar to those found in vivo). In some embodiments, the degree and/or quality of myelination may be assessed using any known method (e.g., via CARS laser).

Immune Cells

In some embodiments, provided methods and compositions include a plurality of at least one type of immune cells. In some embodiments, the at least one type of immune cells includes at least one of macrophages, leukocytes, mast cells, Merkel cells, and/or Langerhans cells. In some embodiments at least some of the plurality of immune cells are functional immune cells (e.g., capable of carrying out their function substantially as if in vivo). In some embodiments, at least some of the plurality of immune cells are present in at least two layers.

In some embodiments, the at least one type of immune cells is exposed to the composition as a gel or hydrogel. In some embodiments, the at least one type of immune cells is exposed to the composition via perfusion. In some embodiments, the at least one type of immune cells is exposed to the composition as a combination of gel or hydrogel, and perfusion.

Endothelial Cells

In some embodiments, provided methods and compositions may further include a plurality of at least one type of endothelial cell. In some embodiments, the endothelial cells comprise a monolayer. In some embodiments, a monolayer may be in the shape of a tube or portion of a tube. In some embodiments, endothelial cells may perform some or all of the functions of a functional vasculature (e.g., transporting nutrients and/or energy, removing wastes, providing cooling). In some embodiments, at least some of the plurality of endothelial cells are present in at least two layers.

In some embodiments, endothelial cells may be introduced to provided compositions as preformed/pregrown conduits. In some embodiments, such preformed conduits may interact with one or more of the other cell types in a provided composition (e.g. nerve cells, immune cells, or others). In some embodiments, endothelial cells may be introduced to provided compositions via seeding or co-seeding the endothelial cells onto a partially or fully formed multi-layer silk composition.

In some embodiments, the at least one type of endothelial cell is exposed to the composition as a gel or hydrogel. In some embodiments, the at least one type of endothelial cell is exposed to the composition via perfusion.

Other Cells

In some embodiments, provided methods and compositions may further include at least one additional cell type. In some embodiments, the additional cell type may be Merkel cells, sebaceous gland cells, hair follicle cells, or melanocytes. In some embodiments, the at least one additional cell type may be cancer cells (e.g., melanoma cells).

Active Agents

In some embodiments, provided methods and compositions may include one or more active agents. In some embodiments, one or more active agents may be present in all layers of a provided composition. In some embodiments, one or more active agents may be present in fewer than all layers (e.g., absent from at least one layer). In some embodiments at least one active agent is present only in a single layer. In some embodiments, at least one active agent is distributed substantially homogenously throughout at least one layer. In some embodiments, at least one active agent is distributed substantially as a gradient in at least one layer. In some embodiments, an active agent may be a therapeutic agent or an inflammatory agent. In some embodiments, a therapeutic agent may be or comprise a cancer therapeutic agent. In some embodiments, the cancer therapeutic is an approved cancer therapeutic agent (e.g., an agent for treating melanoma). In some embodiments a cancer therapeutic agent is an investigational therapeutic agent (i.e., a candidate therapeutic agent). In some embodiments, an active agent may be or comprise an anti-eczema agent. In some embodiments, an active agent may be or comprise an anti-psoriasis agent. In some embodiments, an active agent may be or comprise a wound healing agent (e.g., for treating diabetic ulcers, scar tissue formation, etc). In some embodiments, an active agent may be or comprise an anti-wrinkling agent. In some embodiments, an active agent may be or comprise a cosmetic composition. In some embodiments, an active agent may be or comprise a moisturizer (e.g., a moisturization barrier).

In some embodiments, an active agent may be or comprise one or more inflammatory agents. In some embodiments, an inflammatory agent may be or comprise an anti-inflammatory agent. In some embodiments, an inflammatory agent may be or comprise a pro-inflammatory agent. In some embodiments, wherein the one or more inflammatory agents are selected from the group consisting of anti-histamines, antimicrobial agents (e.g., antibacterial, antifungal, and/or antiviral agents), methotrexate, anti-itch agents, oils (e.g., mineral oil, sunflower seed oil, etc), vitamins (e.g., vitamin D), retinoids, capsaicin, salicylic acid, steroids, lipopolysaccharide, allergens, and toxins. In some embodiments, an active agent may be or comprise application of light to a provided composition (e.g., application of ultraviolet B light).

In some embodiments, an active agent may be or comprise at least one of collagen, laminin, fibronectin, hyaluronic acid, fibrinogen, melanin, sulfated glycosaminoglycans, and/or one or more growth factors. In some embodiments, the one or more growth factors are or comprise epidermal growth factor, fibroblast growth factor, nerve growth factor, platelet-derived growth actor, insulin-like growth factor, or tumor necrosis factor-β, and combinations thereof. In some embodiments at least one active agent may be present in at least one layer of the multi-layer silk composition. In some embodiments, an active agent may be or comprise one or more anti-oxidants and/or one or more polyphenols, or pro-inflammatory agents including lipopolysaccharide or capsaicin.

Electrical Devices

In some embodiments, provided compositions may comprise one or more electrical devices. In some embodiments, provided methods and compositions may further include one or more electrical devices that are functionally connected to at least some of the plurality nervous system cells. In some embodiments, activation of one or more such electrical devices results in the firing of one or more neurons and/or the activation of a plurality of cells in or on the multi-layer silk composition. In some embodiments, the one or more electrical devices are or comprise at least one electrode. In some embodiments, the one or more electrical devices comprise silk fibroin.

In some embodiments, the one or more electrical devices is/are functionally connected to at least some of the plurality nervous system cells. In some embodiments, activation of the one or more electrical devices results in the firing of one or more neurons. In accordance with various embodiments, one or more electrical devices may be introduced above, below, and/or within any particular layer of a provided composition.

In some embodiments, provided compositions may comprise one or more optical devices (e.g., optical fibers). In accordance with various embodiments, one or more optical devices may be introduced above, below, and/or within any particular layer of a provided composition. In some embodiments, the one or more optical devices are biodegradable. In some embodiments, the one or more optical devices comprise silk fibroin. In some embodiments, the one or more optical devices are non-biodegradable.

Exemplary Methods of Making

In some embodiments, the present invention provides methods of making a multi-layer silk compositions including the steps of providing a first layer comprising silk fibroin and keratinocytes, providing a second layer comprising silk fibroin and fibroblasts, providing a third layer comprising silk fibroin and adipocytes, providing a plurality of nervous system cells, and associating the first layer, second layer, third layer, and plurality of nervous system cells to form a multi-layer silk composition, wherein at least some of the plurality of nervous system cells span at least two layers.

In some embodiments, after formation of the "skin" (dermal and epidermal layers) and hypodermal layers are formed, the constructs may be moved and combined on a substrate (e.g., Delrin "waffles", which are wafers with holes to allow nutrients reach the bottom of the matrix) which floats in liquid, to expose the system to air-liquid interface more reliably than, for example, in transwell cultures. Another option, in some embodiments, is to bioprint the individual layers (e.g., using a three dimensional printer), however, due to the complexity of the hypodermal layer specifically (as it is a silk-sponge coated in a collagen gel), such manufacturing is likely to require significant optimization. Alternatively or additionally, in some embodiments, provided compositions may be manufactured using roll to roll manufacturing, where the individual layers (sponger, gels, membranes) with or without cells are made and stamped to combine, to automate and scale the process.

Long-Term Use and Exemplary Uses

In some embodiments, provided compositions may be maintained for a long period of time. In some embodiments, a long period of time is at least one week (e.g., at least 2 weeks, 3 weeks, 4 weeks, 5, weeks, 6 weeks, 7 weeks, 8 weeks, 9 weeks, 10 weeks, 11 weeks, 12 weeks, or more).

Figure 2:
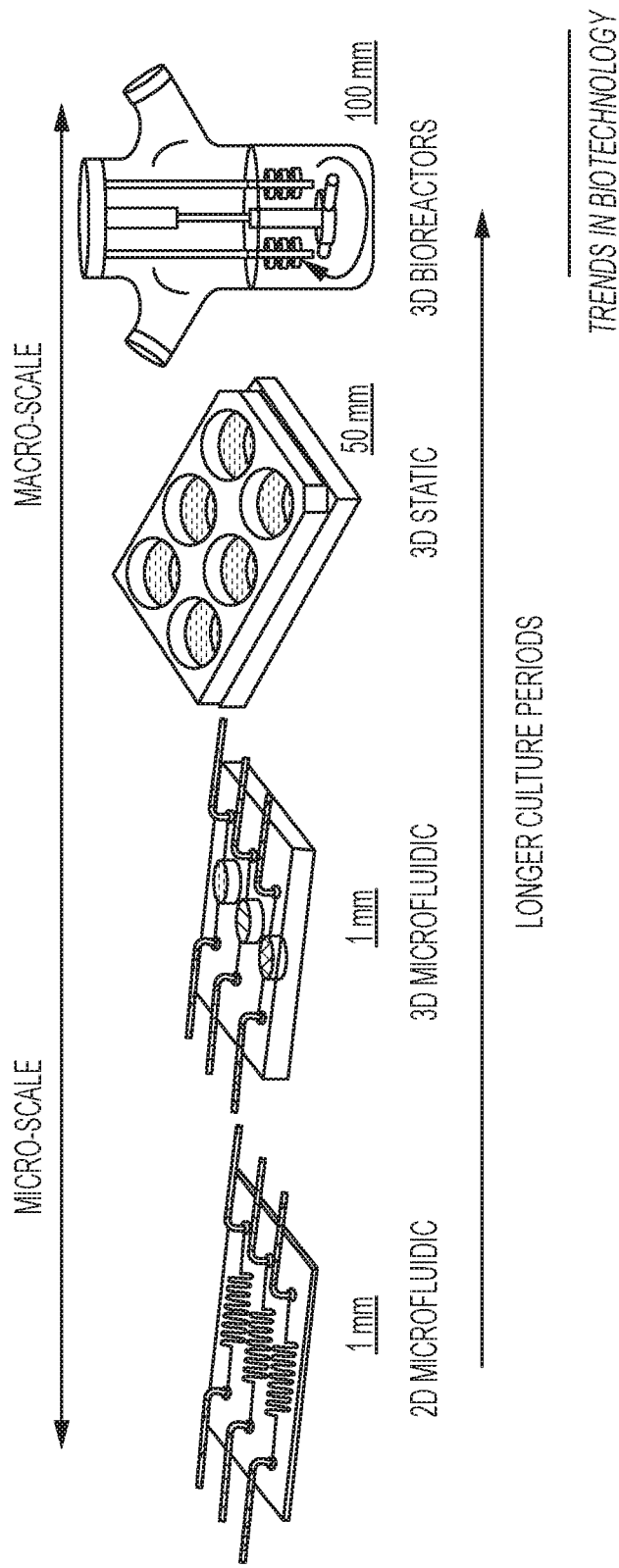
FIG. 2 shows an exemplary formats compatible with certain embodiments of provided compositions at different scales, for example, for long term maintenance of certain provided compositions.

In some embodiments, particular formats may be advantageous in achieving compositions that are amenable to being maintained for long periods of time and/or for achieving a high throughput screening configuration (e.g., a 48 or 96 well plate, for example). In some embodiments, one or more of the exemplary formats shown in FIG. 2 (from Abbott R D, Kaplan D L. Strategies for improving the physiological relevance of human engineered tissues. *Trends Biotechnol* 2015; 33: 401-407) may be used with provided compositions to achieve long term maintenance of certain provided compositions.

Figure 3:
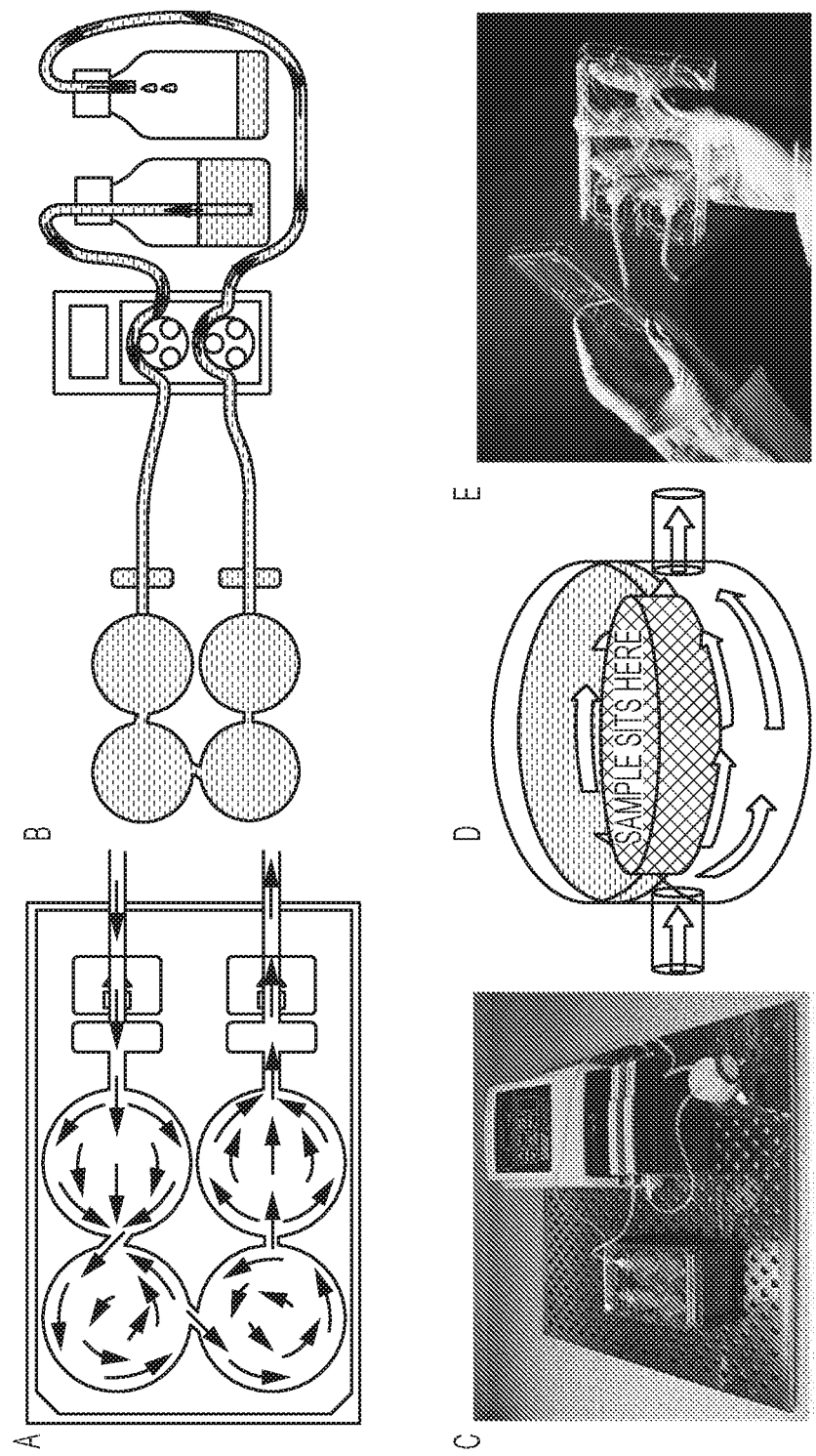
FIG. 3 shows an exemplary skin bioreactor for use with certain compositions provided for herein. Specifically, in panels A and E) Alvetex 6-well perfusion plates were supplied sterile in individual blister packs, which can be connected to non-circulating media or re-circulating media set-ups (panel B). Panel C shows one way that a provided system can be used in a standard cell culture incubator. Panel D illustrates how a substrate (here Delrin waffles) may float on top of perfused media during the cornification stage to allow the epidermis to form at the air-liquid interface.

In some embodiments, provided compositions may be maintained indefinitely. In some embodiments, such long useful life may be achieved through use of a bioreactor type design. A non-limiting, exemplary bioreactor design that is in accordance with various aspects of the present invention is shown in FIG. 3.

While contemplating a wide variety of uses for provided compositions, certain exemplary uses are described below in order to provide a clearer picture of some of the benefits of certain embodiments. In some embodiments, provided multi-layered compositions may be used to assess/characterize the efficacy of certain drugs (e.g., formulated for injection or topical or transdermal delivery). In some embodiments, provided compositions may also be useful in studying certain diseases including fibrosis, certain cancers, inflammation, chronic wounds (including diabetic ulcers), and other skin diseases due to the longevity of sustained cultivation and greater physiological relevance of provided compositions as compared to previously known compositions. In some embodiments, provided compositions may be used as wound dressings and/or to study wound healing. In some embodiments, provided compositions may be used as transplant material (e.g., to replace damaged or missing skin on a patient, for example). In some embodiments, provided compositions may also be useful in testing the effects of one or more active agents, for example, via high throughput screening.

EXAMPLES

Materials and Methods

Unless otherwise specified, the below examples each use the following materials and/or methods, as applicable:

Reagents

Cell culture media and supplements were purchased from Invitrogen unless otherwise noted. Transwells, horseradish peroxidase (Type IV), and hydrogen peroxide were purchased from Sigma. Bovine collagen (3 mg/mL) was purchased from Advanced Biomatrix. Antibodies were purchased from Abcam (Anti-beta III Tubulin, Phalloidin) and Sigma (DAPI).

Silk Processing

The standard silk processing protocols were followed as described by Rockwood et al. (2011) with a 60-minute extraction time. Silk solution was utilized to generate the artificial dermis. To form silk scaffolds, lyophilized 30-minute extracted silk was resolubilized in 17% (w/v) hexafluoro-2-propanol (HFIP). Salt was sieved at 500-600 µm pore size, and 2 mL of silk was poured over 6.8 grams of sieved salt in a polyethylene container for 2 days and sealed. The remaining HFIP was allowed to evaporate by opening the seal for 1 day in a fume hood, after which the containers were submerged in methanol for 1 day followed by an additional day of evaporation in a fume hood. Then the vials were rinsed in 2 L beaker of deionized water, changing the water up to 6 times over a 3 day period. The silk scaffolds were then carefully cut into cylinders (2 mm height×20 mm diameter) and autoclaved before use. Up to 1 day prior to use, scaffolds were submerged in FBS-containing media (1×DMEM, 1×PSF, 10% FBS).

Cell Maintenance

Fibroblasts were maintained in 1×DMEM, 10% FBS, 1×PSF. Keratinocytes were maintained in KGM Gold (Lonza) supplemented with Bullet kits (Lonza). HiNSC were maintained in knockout media (KO) in gelatin-coated tissue culture plastic. Cells were maintained in a 37° C./5% $CO_2$ incubator.

Fat Isolation and Scaffold Preparation for Hypodermis

Lahey clinic provided the primary human adipose tissue from abdominoplasty procedures with institutional review board approval (Protocol #0906007). Briefly, adipose tissue was dissected with blunt dissection tools to isolate adipose tissue. The adipose tissue was liquefied in a blender. The scaffolds and the liquefied adipose tissue were placed in a 50 mL conical tube and placed in the incubator for 30 minutes. After 30 minutes the scaffolds were individually placed into 6 well plates and kept in the incubator for another 2 hours until maintenance media was added (1×DMEM/F12, 10% FBS, 1×PSF).

HFIP scaffolds were cut to 2 mm thick, autoclaved, and soaked in FBS-containing cell culture media in a 37° C. 5% $CO_2$ incubator for at least 2 hours prior to addition of lipoaspirate.

Preparation of Multi-Layer Compositions

Figure 4:
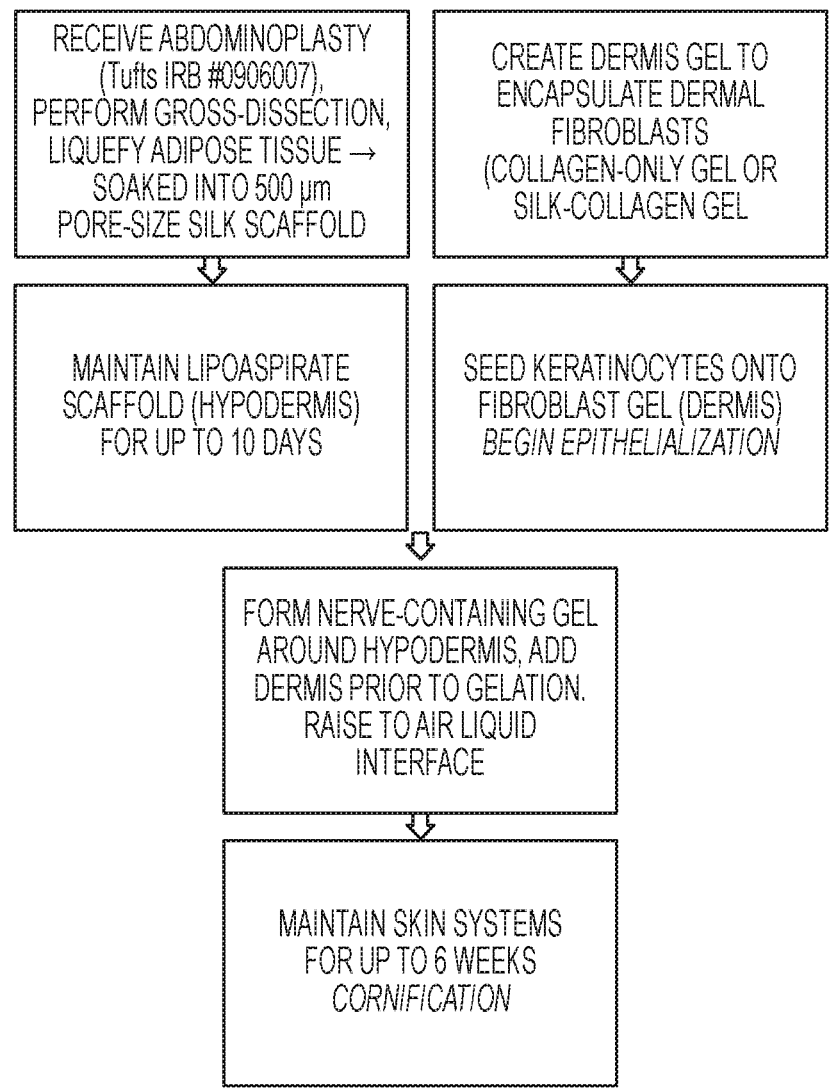
FIG. 4 shows a flowchart of certain exemplary provided methods.

In accordance with various embodiments, the compositions describe in these examples were made substantially in accordance with the some or all of the procedures listed in FIG. 4, FIG. 5 and/or the methods described in Bellas et al., In vitro 3D full-thickness skin-equivalent tissue model using silk and collagen, Macromolecular Bioscience, 2012, 12: 1627-1636, the disclosure of which is hereby incorporated in its entirety.

Figure 6A:
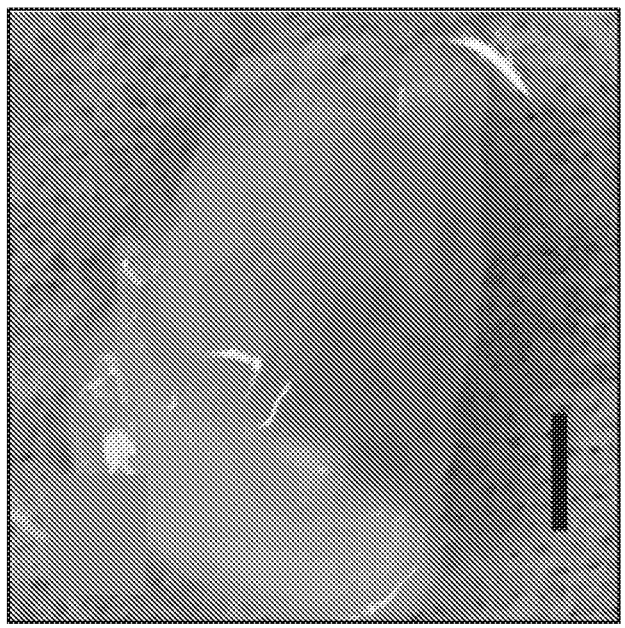
FIG. 6 shows an exemplary comparison of (6A) silk-collagen three-layered skin versus (6B) collagen-only three-layered skin. Samples were cut in half after 42 days in culture after formalin-fixation. Scale is 3.5 mm.
Figure 6B:
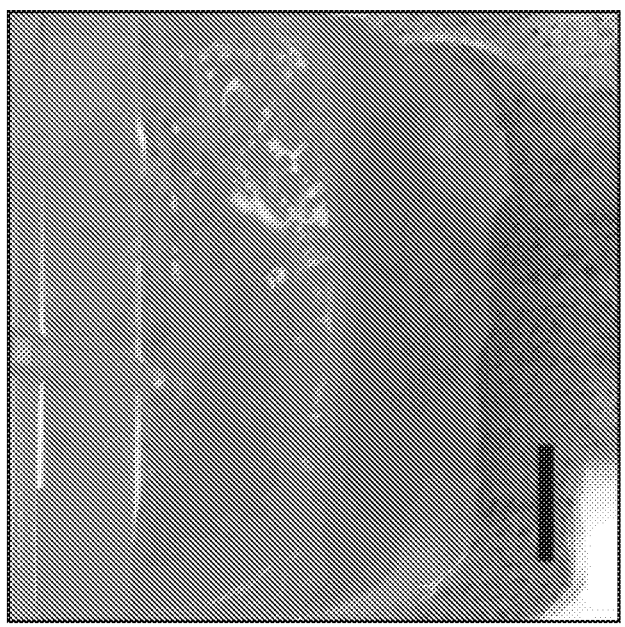

FIG. 6 shows an exemplary comparison between a three layered silk fibroin-collagen composition (panel 6A) and a three layered collagen only composition (panel 6B). The three layers in FIG. 6 are dermal, epidermal and hypodermal layers.

Figure 7:
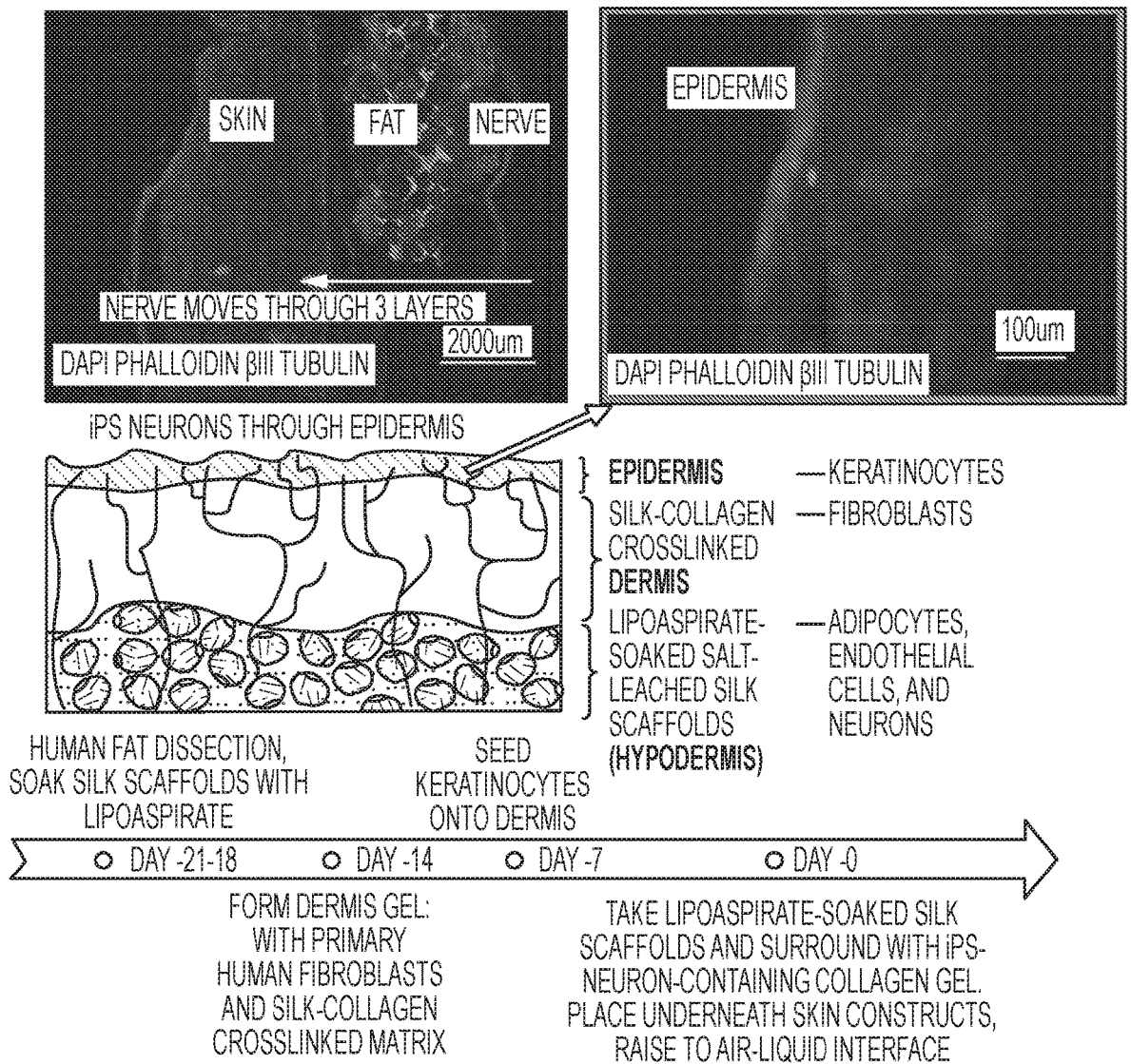
FIG. 7 Summary of exemplary model components Immunohistochemistry of organotypic skin models after 21 days in culture (Top left), βIII Tubulin (a nerve marker) is evident in all three layers: hypodermis, dermis, and at the epidermis (Top right). Timeline of organotypic model formation (Bottom).

FIG. 7 shows an exemplary timeline and methods for the preparation of certain provided compositions. In addition, the top left and top right panels of FIG. 7 show exemplary innervation across layers (top left panel) and within the epidermal layer (top right panel) as is more deeply shown and discussed in the below examples.

Biological Activity—Glycerol Secretion

Cell culture media was frozen in aliquots at −20° C. until analysis. Bioassay systems Enzychrom Adipolysis Assay kit was followed per product instructions (Fisher Scientific catalog number 50-489-245).

Biological Activity—dsDNA Quantification

Samples were frozen at −20° C. in 1× tris-edta lysis buffer until analysis. Product protocol for Invitrogen Quant-IT PicoGreen dsDNA assay kit (P11496).

Biological Activity—Cytokine Array

Cell culture media was frozen in aliquots at −20° C. until analysis. Samples were analyzed with a Human cytokine antibody array (Abcam ab133996) per product instructions and imaged via a chemiluminescent imager. Signal intensity was calculated as a percentage of the signal form the positive control (i.e., biotin-conjugated IgG printed directly on the membrane).

Biological Activity—ELISA (IL-8 and NPY)

Cell culture media was frozen in aliquots at −20° C. until analysis. The ELISA for IL-8 was purchased from abcam (ab46032) and followed per product instructions.

The ELISA for NPY was purchased from EMD Millipore (product number EZHNPY-25K) and performed per product instructions.

Assessment of Function/Mechanical Properties—Durometer

A Rex gauge 1600 series Type 00 (McMaster Carr) was used to analyze durometer readings for each sample. The durometer was held vertically on samples measured via the gravity of the durometer impact on the sample; the durometer was kept in place for 20 seconds per measurement and the reading was recorded. 5 measurements were made per sample in different locations.

Assessment of Function/Mechanical Properties—Compressive Analysis

Samples were cut with an 8 mm biopsy. Samples were analyzed via a percentage of height with respect to strain up to 35%, initial height was recorded for each individual sample to account for size disparity.

Unless otherwise specified, imaging studies were conducted using the reagents in Table 2

TABLE 2

| Immunohistochemistry Reagents | | | |
| --- | --- | --- | --- |
| Antibody | Specificity | Product info | Concentration |
| Cytokeratin 10 (K10) | Keratinocytes | Abcam ab76318 | 1:150 |
| β111 Tubulin (Tuj1) w/Alexafluor 488 | Nerves (all) | Abcam ab195879 | 1:100 |
| Phalloidin-TRITC | Actin | Sigma P1951 | 1:80 |
| DAPI | Nuclei | Sigma D9452 | 1:1000 |
| Secondary goat anti rabbit IgG-FITC | Secondary to K10 | Sigma F0382 | 1:160 |
| NaV1.8 | Sodium channel NaV1.8 | Abcam ab66743 | 1:500 |
| Secondary mouse anti rabbit-TRITC | Secondary to NaV1.8 | (need to verify) | 1:200 |

Histology

Standard haematoxylin and eosin staining procedures were used on 25 μm frozen sections.

Electrical Stimulation of hiNSCs

Cell Culture and Instrumentation 2D samples of HiNSCs or SH-SY5Y cells were cultured in monolayer for 3-5 days on 60 mm petri dishes with gold wires arranged 0.5 cm apart, or on multi-electrode gold arrays on standard glass slides.

Samples were connected to a function generator and stimulated at 1 Hz square wave with 2 ms pulses for 1 hour, between 1.5-2 volts/cm applied.

Media samples were taken before stimulation, immediately after, and 24 hours after stimulation. Cells were stained with Live/Dead and imaged immediately following stimulation. Following imaging, cells were fixed in 10% formalin buffered phosphate for 15 minutes and kept until staining.

Live Imaging

Samples were connected to a function generator and stimulated at 1 Hz square wave with 2 ms pulses for 30 minutes, between 1.5-2 volts/cm applied. Cells were incubated with 2 µM of X-Rhod-AM-1 dye for 30 minutes prior to imaging.

Outcome Measures

Unless otherwise specified, the performance of the exemplary compositions provided in the following examples were assessed using at least some of the potential measures shown in Table 3 below:

TABLE 3

Outcome measures for silk-based human skin equivalents compositions

| Characteristic of model | Functional outcome | Experimental validation |
| --- | --- | --- |
| Cohesive, tri-layered system | Layer-to-layer interactions; bulk interactions | Histology-morphology<br>LIVE/DEAD-cytotoxicity of construct<br>ELISA, cytokine array-cytokine release to determine functional crosstalk |
| Diverse cell types present; proliferating | Physiologically relevant tissue; behaves as skin | Immunostaining-distinct cell types present in physiologically relevant locations (i.e. epidermal stratified keratinocytes, etc.)<br>Pico-green-Temporal analysis of DNA, cell proliferation<br>Reverse transcriptase PCR-Genetic confirmation |
| Length of time to innervation low | Nerve cells present throughout hypodermis, dermis, epidermis | Immunostaining-presence of cells with time<br>Histology-morphological analysis with time |
| Length of time in culture high | Can maintain tissue culture for 3-6 months for analysis of drug interactions, disease | LIVE/DEAD-cytotoxicity with time; TUNEL apoptosis marker via histology |
| Functional nerves throughout skin | Model sensitive to physical/chemical stimuli | Calcium imaging of neurons via confocal microscopy functional calcium ions of nerve cells<br>Monitoring optimal cell density for function<br>Imaging cellular markers |

Example 1—Exemplary Innervated Skin Model Compositions

In this Example, compositions comprising 1) silk fibroin-collagen, 2) collagen only dermis+/−keratinocytes for skin only, 3) innervated skin, 4) innervated skin with hypodermis, and 5) hypodermis only control with nerve (collagen gel with nerve underneath silk sponge with fat) were tested for viability in culture for 3 weeks.

Briefly, adipose tissue was dissected with blunt dissection tools to isolate adipose tissue. The adipose tissue was liquefied in a Ninja blender. The scaffolds and the liquefied adipose tissue were placed in a 50 mL conical tube and placed in the incubator for 30 minutes. After 30 minutes the scaffolds were individually placed into 6 well plates and kept in the incubator for another 2 hours until maintenance media was added (1×DMEM/F12, 10% FBS, 1×PSF).

Figure 8:
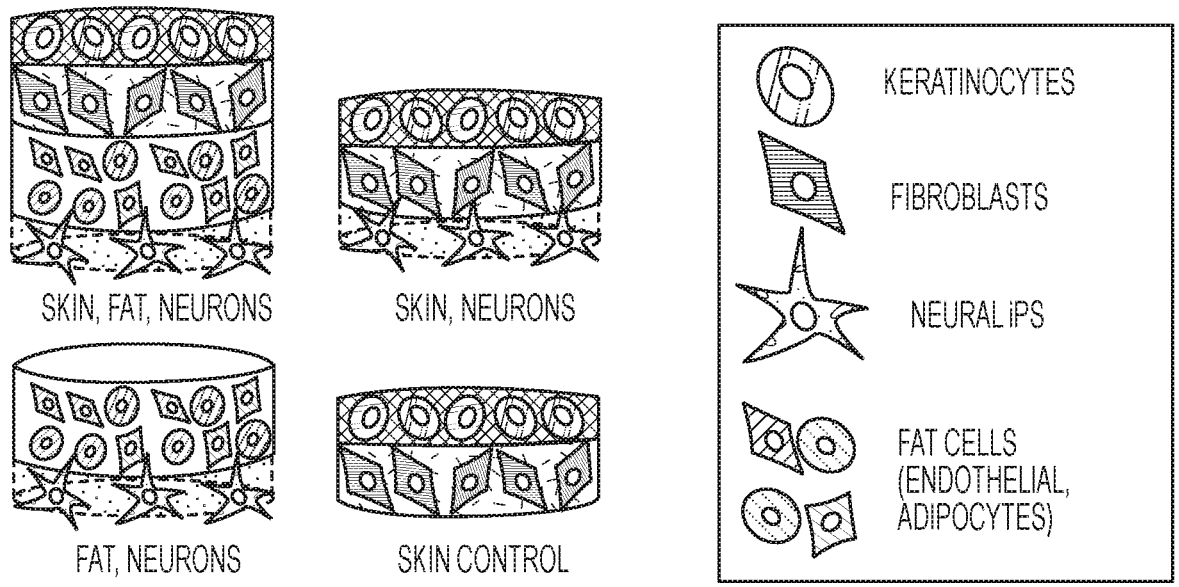
FIG. 8 shows exemplary embodiments with, for example, collagen only dermis and silk-collagen dermis.

In order to demonstrate the capability to innervate provided compositions, a parametric study was designed to explore various conditions to determine whether or not the hypodermis impedes the ability for the nerves to migrate (see FIGS. 10-13). A summary of the experimental groups is shown in FIG. 8; additionally each group had a corresponding control sample without keratinocytes to further examine whether there are any interactions between the nerves and the keratinocytes.

Additionally, in order to increase the tensile strength of the dermis, two conditions were explored: pure collagen gel, and a silk-collagen horseradish peroxidase (HRP)/hydrogen peroxide dityrosine crosslinked gel. While the crosslinked silk hydrogels have been explored before, and are cytocompatible and biocompatible, the crosslinked silk-collagen hydrogels had not yet been explored for skin tissue engineering. However, preliminary data suggests these hydrogels have enhanced mechanical integrity and easier handling compared to the pure collagen gels.

Figure 9:
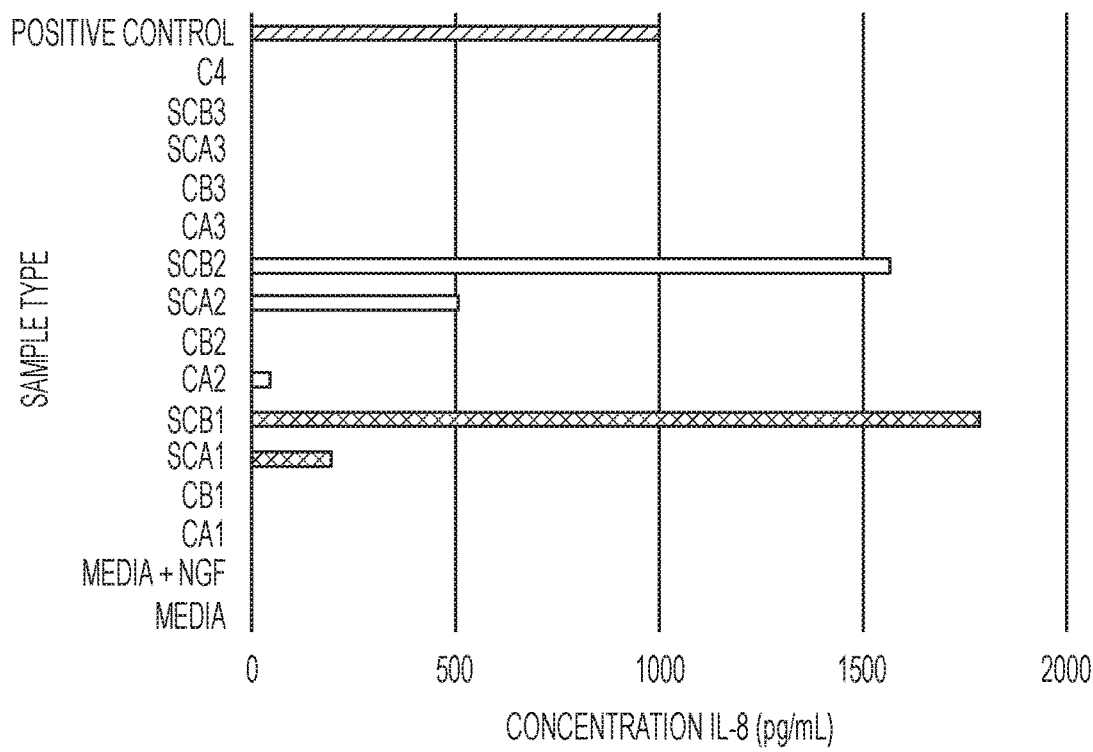
FIG. 9 shows an exemplary graph of interleukin-8 (IL-8) expression in certain exemplary embodiments.

In FIG. 9, inflammatory cytokine interleukin 8 (IL-8) release at 3 weeks in culture (endpoint for this experiment) is shown. Neuropeptide and/or paracrine signaling can cause NGF and IL-8 secretion from keratinocytes. The secreted NGF and IL-8 are main communication signals from the keratinocytes to the nerve.

As shown in FIG. 9, SCA1 (fibroblast only gel) had low signal compared to SCB1 (fibroblast and keratinocyte) which had a much higher concentration of IL-8. When nerve gel was added to this system in SCA2 (fibroblast and nerve), the concentration of IL-8 doubles compared to without nerve (SCA1), but in SCB2 the addition of nerve to the keratinocyte/fibroblast system did not seem to have a major effect in comparison to SCB1. Additionally, no collagen only samples (those without silk fibroin) had a detectable level of IL-8. Based on these results, it appears that the silk fibroin-collagen dermis environment enhances the ability for these cells to communicate.

Figure 10:
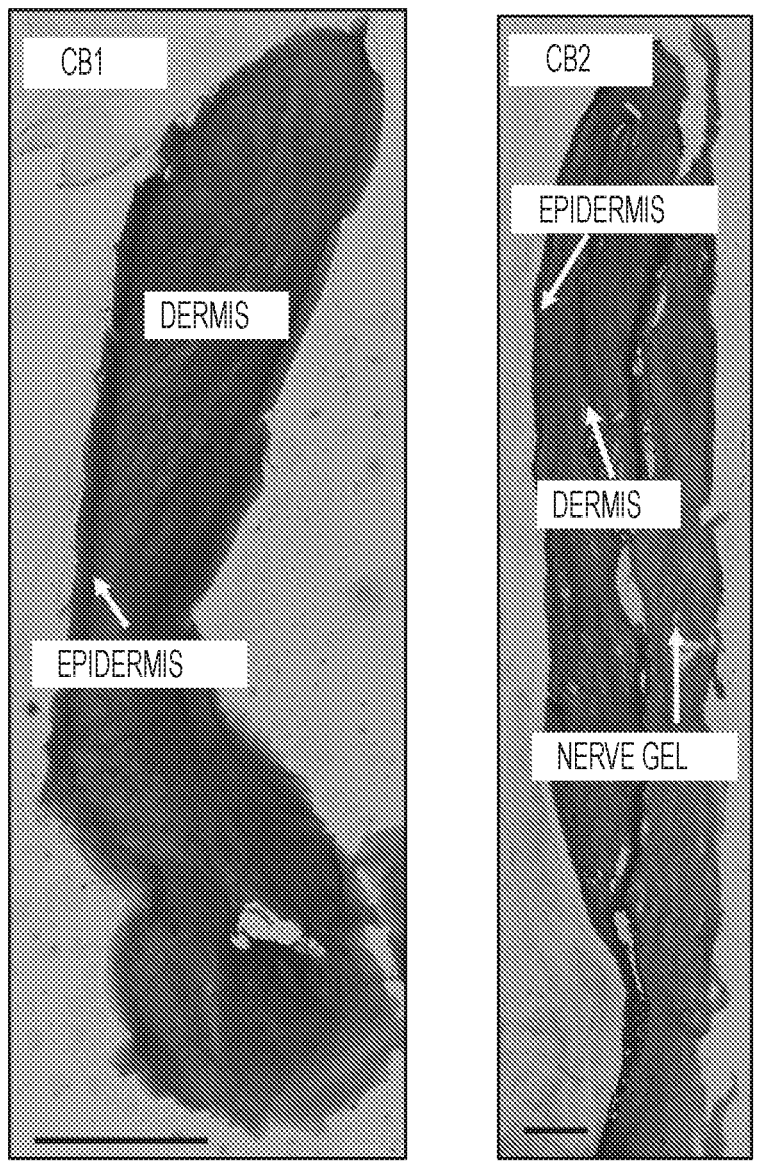
FIG. 10 shows exemplary hematoxylin and eosin staining of certain collagen only (no silk fibroin) compositions including only a dermis and epidermis (CB1), or dermis, epidermis, and nerve cells (CB2). As shown, cell clusters in these compositions are difficult to resolve. Scale bars are 1 cm.
Figure 11:
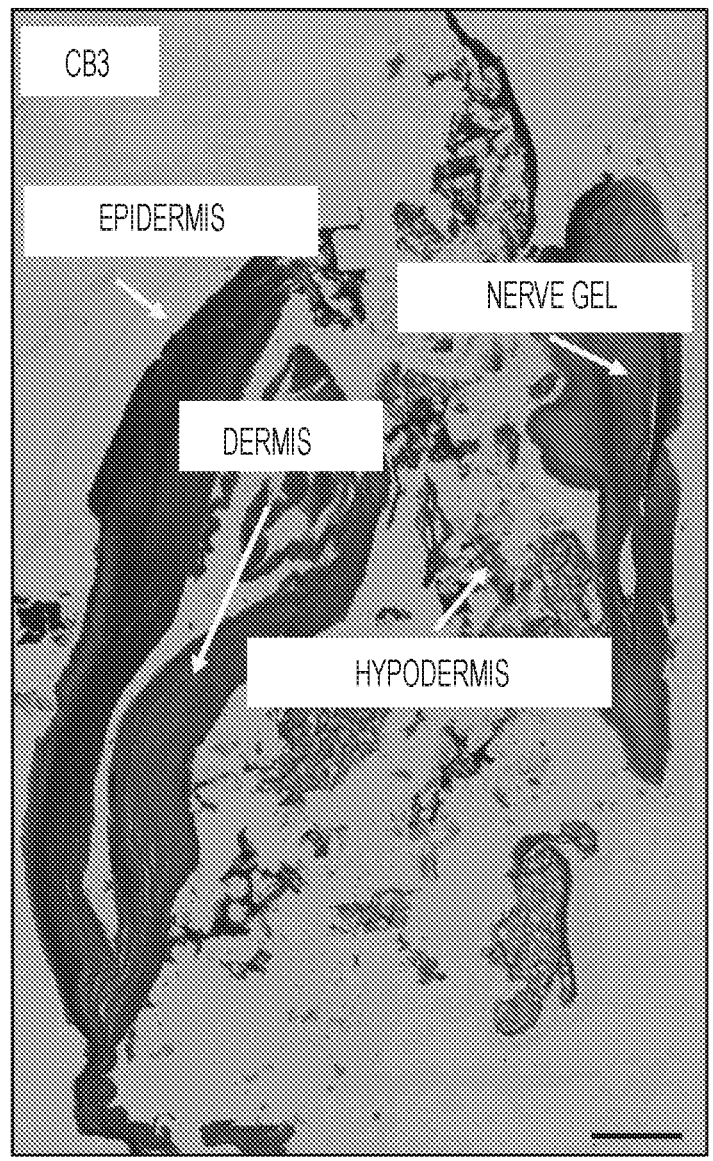
FIG. 11 shows exemplary hematoxylin and eosin staining of certain collagen only (no silk fibroin) compositions including a dermis, epidermis, hypodermis and nerve cells. As is shown in the figure, the hypodermis layer fell apart from this composition, the individual layers peeled, and it was again difficult to resolve individual cell clusters. Scale bar is 1 cm.

A histological comparison was made between silk fibroin-collagen compositions as compared to collagen only compositions in order to accurately assess the relative in situ morphology of the compositions. In FIG. 10, it is clear that the collagen only compositions suffered from poor ability to resolve cell clusters as well as a peeling apart of the dermis versus epidermal layers and, in CB2 of FIG. 10, the nerve gel layer as well. FIG. 11 shows that collagen only compositions including dermal, epidermal, hypodermal, and nerve gel layers also failed to adhere, exhibiting significant peeling and significant difficulty resolving individual cell clusters.

Figure 12:
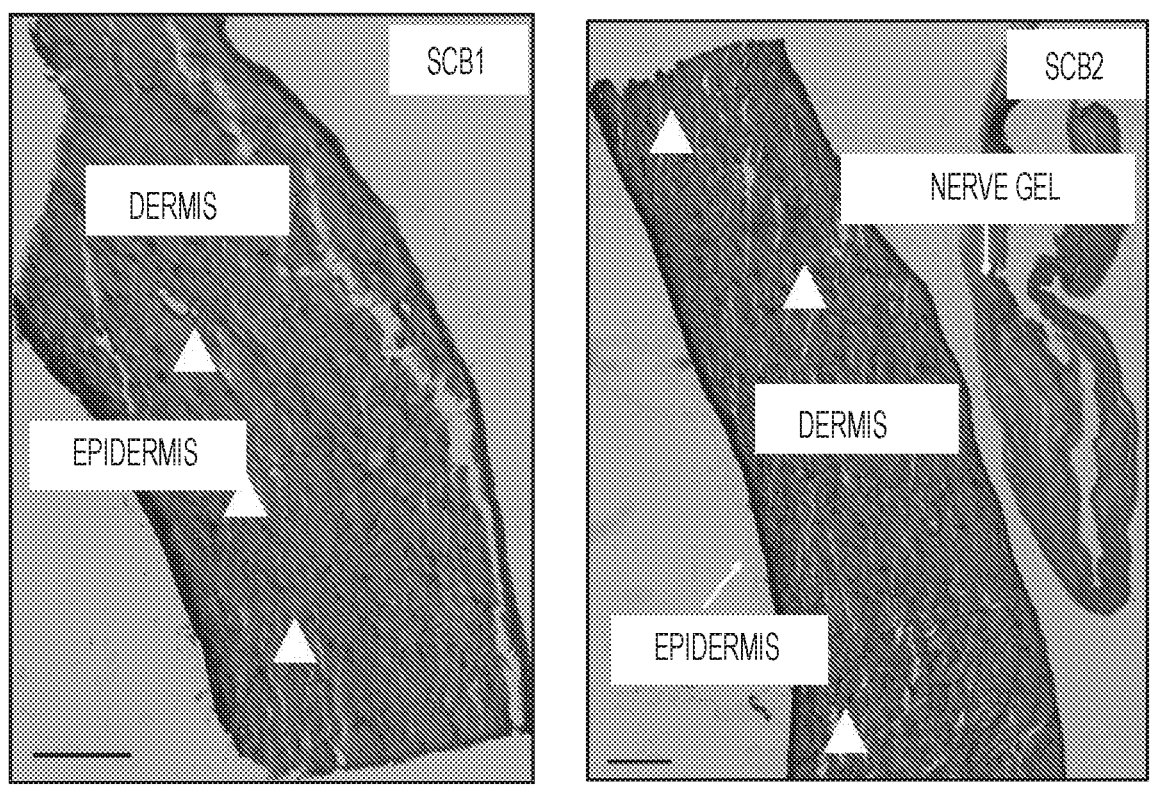
FIG. 12 shows exemplary hematoxylin and eosin staining of certain provided compositions including silk fibroin and collagen. Panel SCB1 shows an exemplary provided composition comprising only a dermis and epidermis, and panel SCB2 shows an exemplary provided composition comprising a dermis, epidermis, and nerve cells. Cell clusters are indicated by white triangles, and scale bars are 1 cm.
Figure 13:
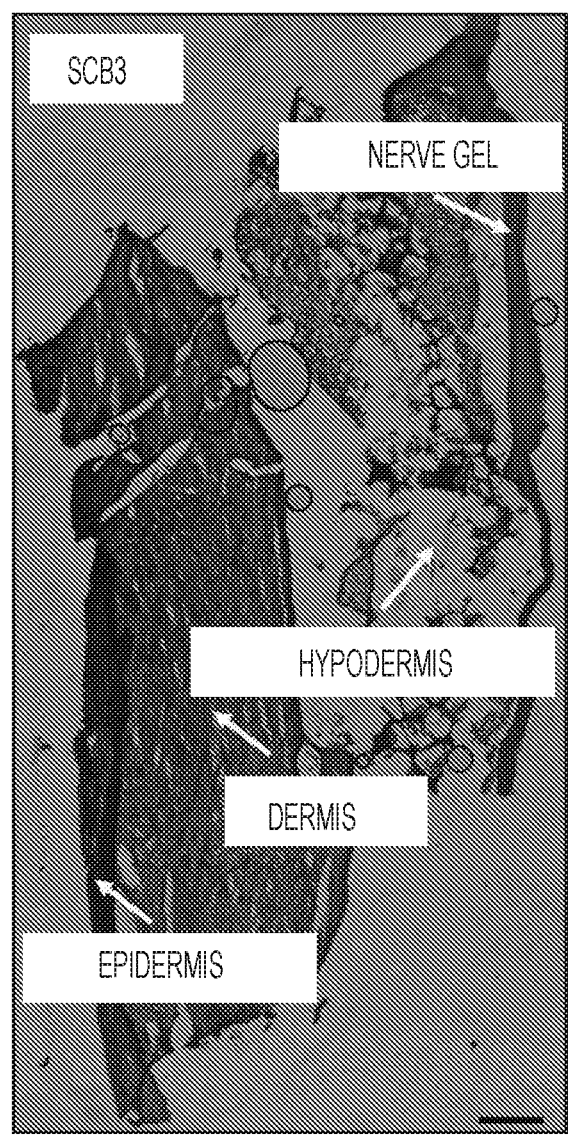
FIG. 13 shows exemplary hematoxylin and eosin staining of certain provided embodiments including silk fibroin and collagen. The exemplary composition includes a dermis, epidermis and hypodermis as well as nerve cells. Scale bar is 1 cm.

In contrast, compositions including both silk-fibroin and collagen showed vastly different results. Specifically, and as shown in FIG. 12, the dermal and epidermal layers showed good adhesion and integration, with individual cell clusters readily resolvable (see the white triangles). Of note is that, as shown in CB2 of FIG. 12, the nerve gel did not adhere to the dermal layer of the exemplary compositions. FIG. 13 shows exemplary silk fibroin-collagen compositions including a dermis, epidermis, hypodermis, and nerve gel layer. As can be seen in FIG. 13, the dermal and epidermal layers integrated well and it was possible to resolve individual cell clusters (white arrows). While the hypodermal and nerve layers still exhibited some peeling, it was less than in the collagen only compositions.

Figure 14:
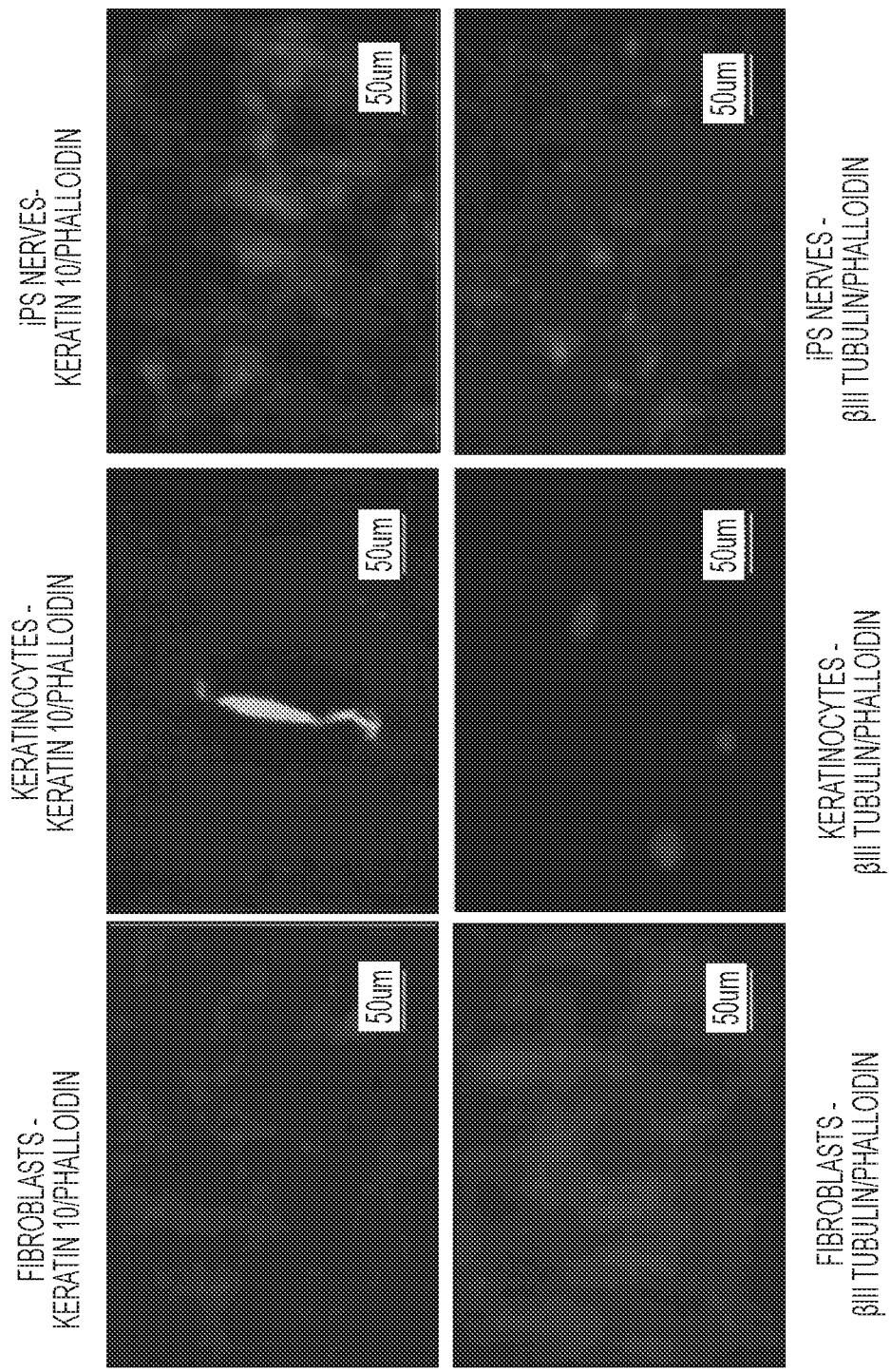
FIG. 14 shows the results of exemplary immunohistochemistry of certain provided embodiments. As is shown in FIG. 14, the antibodies used, K10 (to monitor cytokeratin 10 produced by keratinocytes), and βIII Tubulin (or TUJ1) (to monitor mature neurons) do not react with other cell types present in the exemplary provided compositions. Without wishing to be held to a particular theory, it appears that the observed signals are indeed from the hiNSC nerves introduced into the provided compositions, and not from any non-specific signal.

Next, antibodies for our studies K10 (to monitor cytokeratin 10 produced by keratinocytes) and βIII Tubulin (or TUJ1) (to monitor mature neurons) were used to confirm that these antibodies did not react with other cell types present in these exemplary compositions, specifically fibroblasts, keratinocytes, and iPS nerves. As shown in FIG. 14, no non-specific binding is observed.

Figure 15:
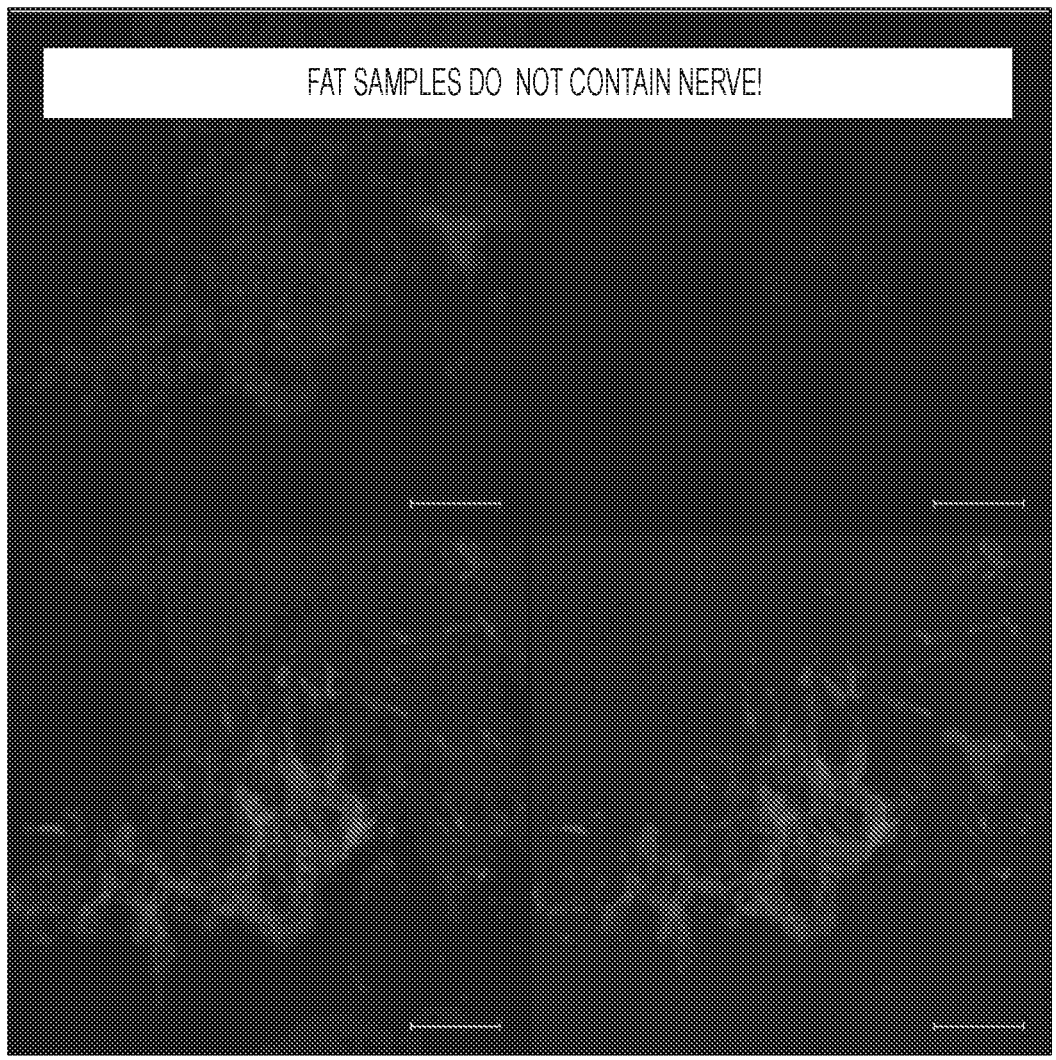
FIG. 15 shows an exemplary photograph of dissected lipoaspirate that is stained for βIII Tubulin after 1 week in culture. As is shown, there is no detectable βIII Tubulin signal (green), indicating that no nerves are present in the dissected lipoaspirate. Scale is 100 um. Lipoaspirate scaffold (fat only, hypodermis equivalent) at 1 week in culture does not stain positive for βIII Tubulin (top right, lack of green signal). Blue is DAPI (top left), red is phalloidin (bottom left), bottom right is merge.

In addition, another important control was needed to determine whether the lipoaspirate isolated for making certain provided compositions had functional nerves remaining after dissection and incorporation into silk scaffolds. As is shown in FIG. 15, no βIII Tubulin was observed in the lipoaspirate used in making the provided compositions in this Example after 1 week in culture. As such, from the negative results in FIGS. 14-15, it is expected that any nerve growth observed presumably occurs as a result of exogenously added nervous system cells, and not from any non-specific signal.

Figure 16:
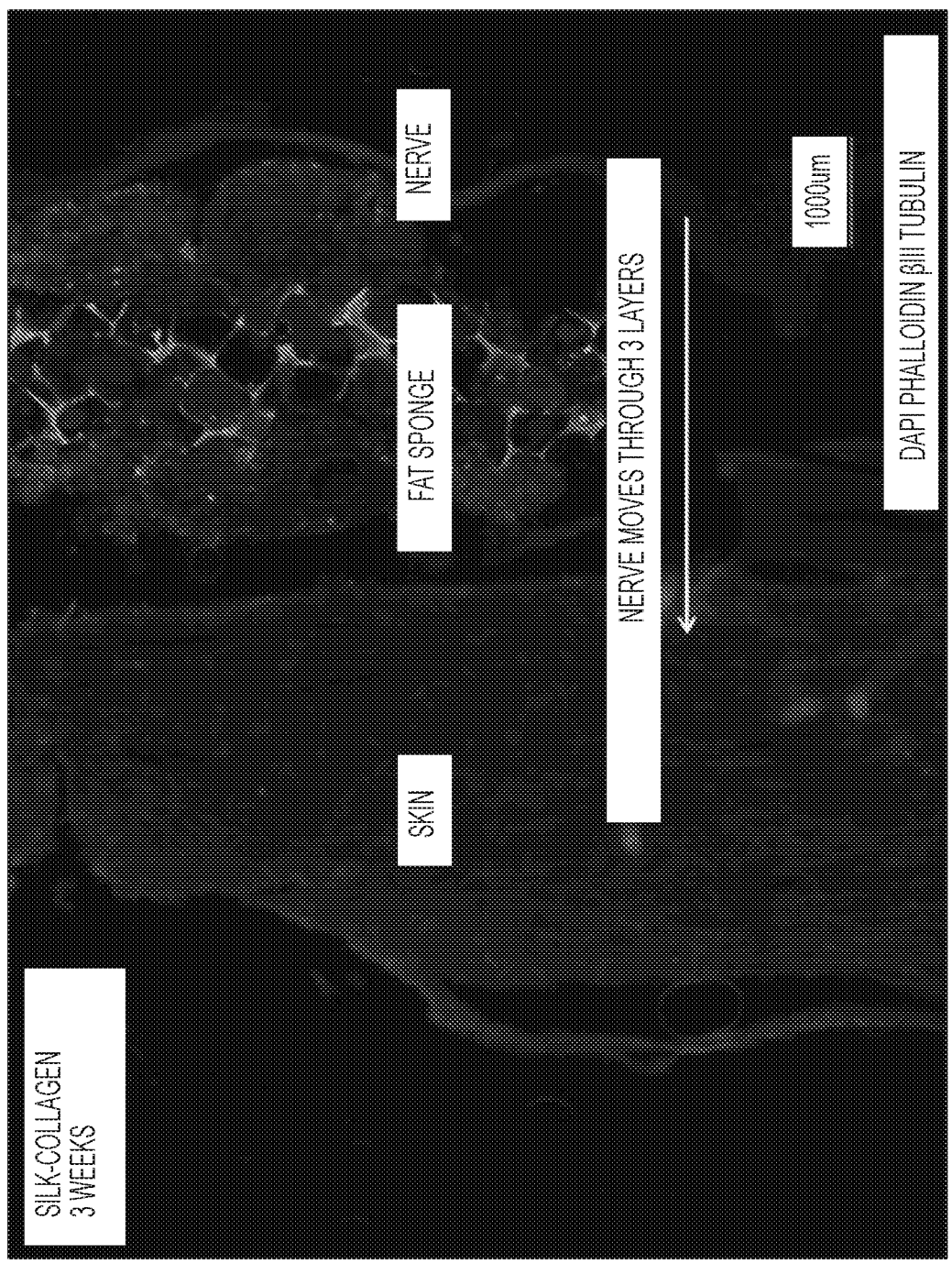
FIG. 16 shows an exemplary photograph of a certain exemplary embodiment comprising silk fibroin and collagen. As can be seen, the provided silk fibroin-collagen composition includes a multi-layer skin portion, a "fat sponge" portion (isolated similarly to the lipoaspirate in FIG. 16), and nerves, which are present in multiple layers after 3 weeks in culture. As is shown, the layers are integrated with one another, including growth of nerves through multi-later skin portion. Scale bar is 1000 μm.
Figure 17:
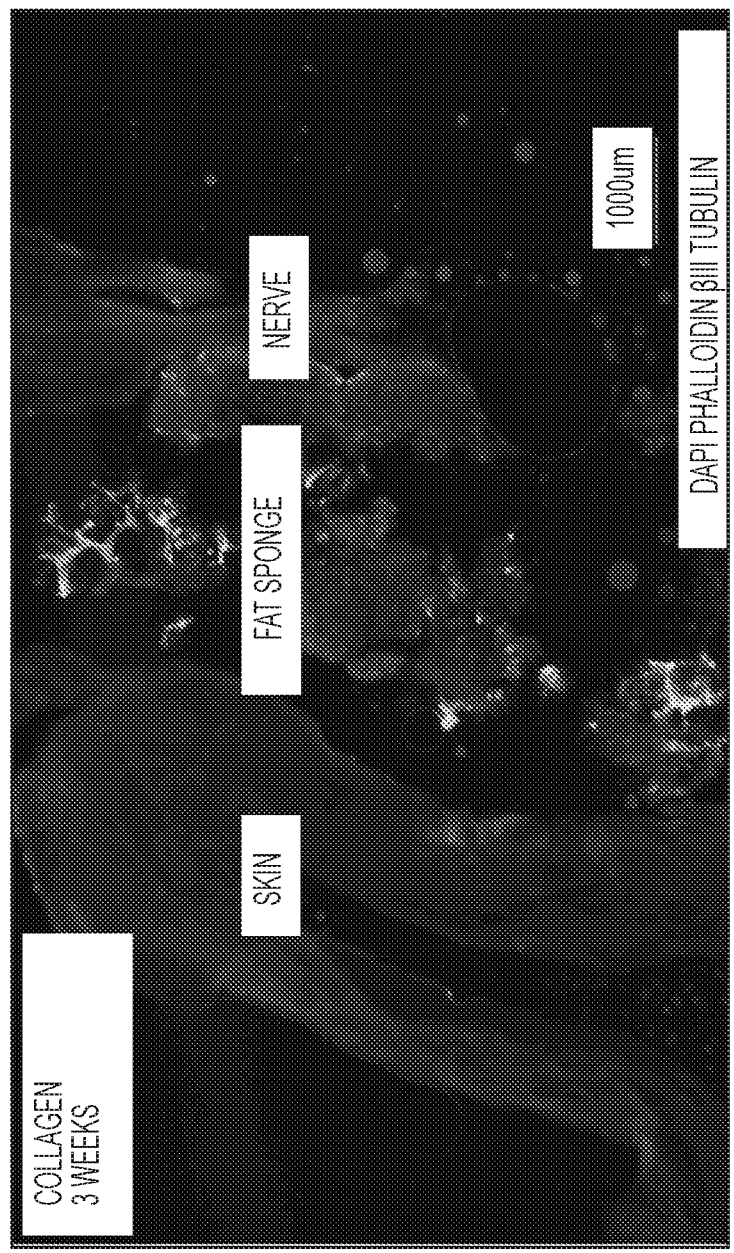
FIG. 17 shows an exemplary photograph of a certain exemplary composition including collagen, but no silk fibroin. As can be seen, the exemplary collagen composition includes a multi-layer skin portion, a "fat sponge" portion (isolated similarly to the lipoaspirate in FIG. 16), and nerves, which are not present in multiple layers after 3 weeks in culture. As is shown, the layers are not well integrated. Scale bar is 1000 μm.

When provided silk fibroin-collagen compositions including dermal and epidermal layers (also referred to as "skin" in these examples), a fat layer and nerve gel layer were assessed, clear nerve growth into the skin layers was observed (see FIG. 16). Specifically, as shown in FIG. 16, mature nerve cells are found in the fat layer as well as in the skin layers, thus showing movement of nerve cells through all three layers of these exemplary provided compositions by 3 weeks in culture. FIG. 17 shows nerve staining in collagen only compositions, where nerves appear to have moved through the fat layer, but are only sporadically found in the dermal layer, in contrast to the silk-fibroin-collagen compositions.

Figure 18:
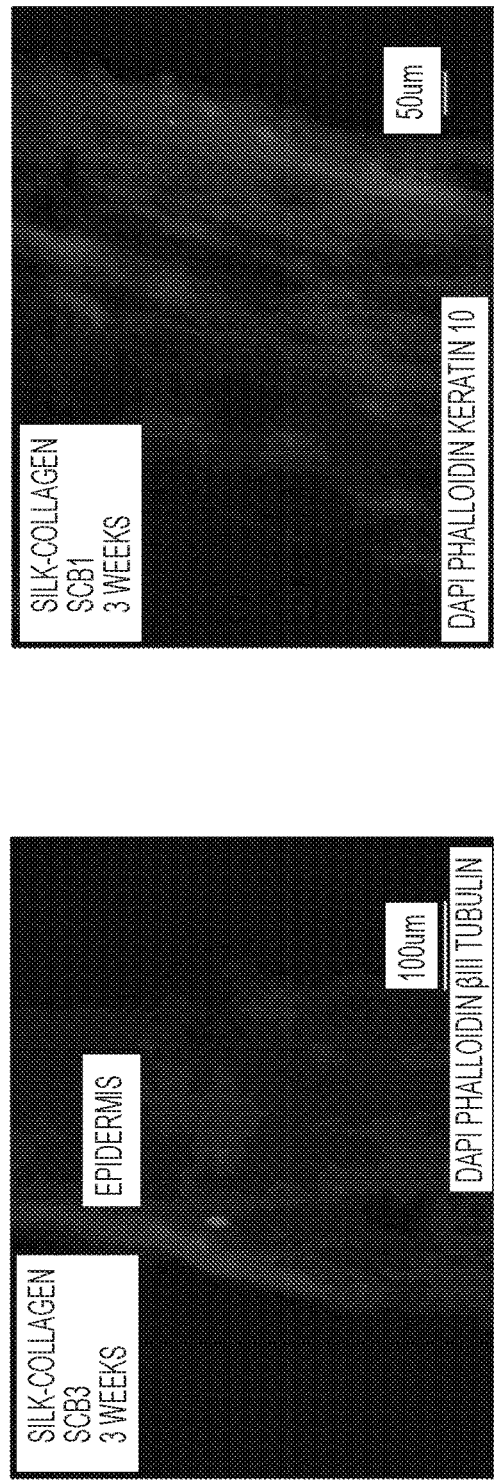
FIG. 18 shows photographs of certain exemplary embodiments. In the top left panel, showing an exemplary silk fibroin-collagen composition, nerves are evident in the epidermal layer. In the top right panel, showing a view of the multi-layer skin portion, keratin is evident along the epidermis. In the bottom panels, exemplary silk fibroin-collagen blend compositions are shown showing cells at the nerve/skin interface (bottom left) and cells at the fat/nerve interface (bottom right).
Figure 18:
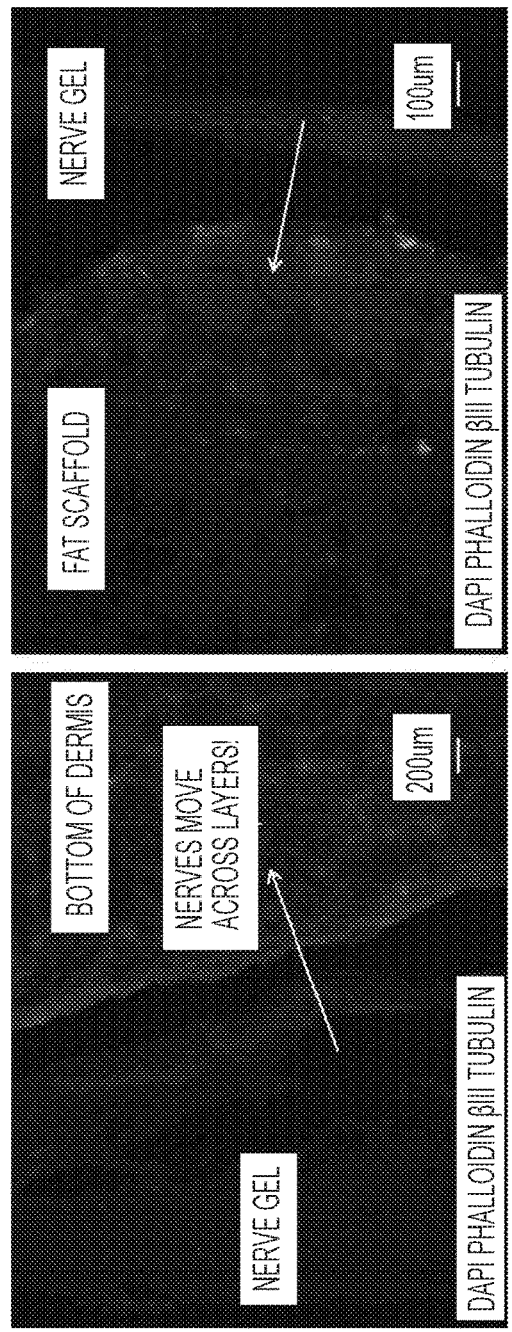

FIG. 18 shows exemplary close views of certain layers. Specifically, in the top left panel of FIG. 18, individual mature neurons may be observed in the epidermal layer of certain provided silk fibroin-collagen compositions after 3 weeks in culture, with the top right panel also showing keratin formation along the epidermal layer. The bottom panels of FIG. 18 show cells at the nerve/skin interface (bottom left) where nerves are seen moving across layers, and also shows cells at the fat/nerve interface (bottom right).

Figure 19:
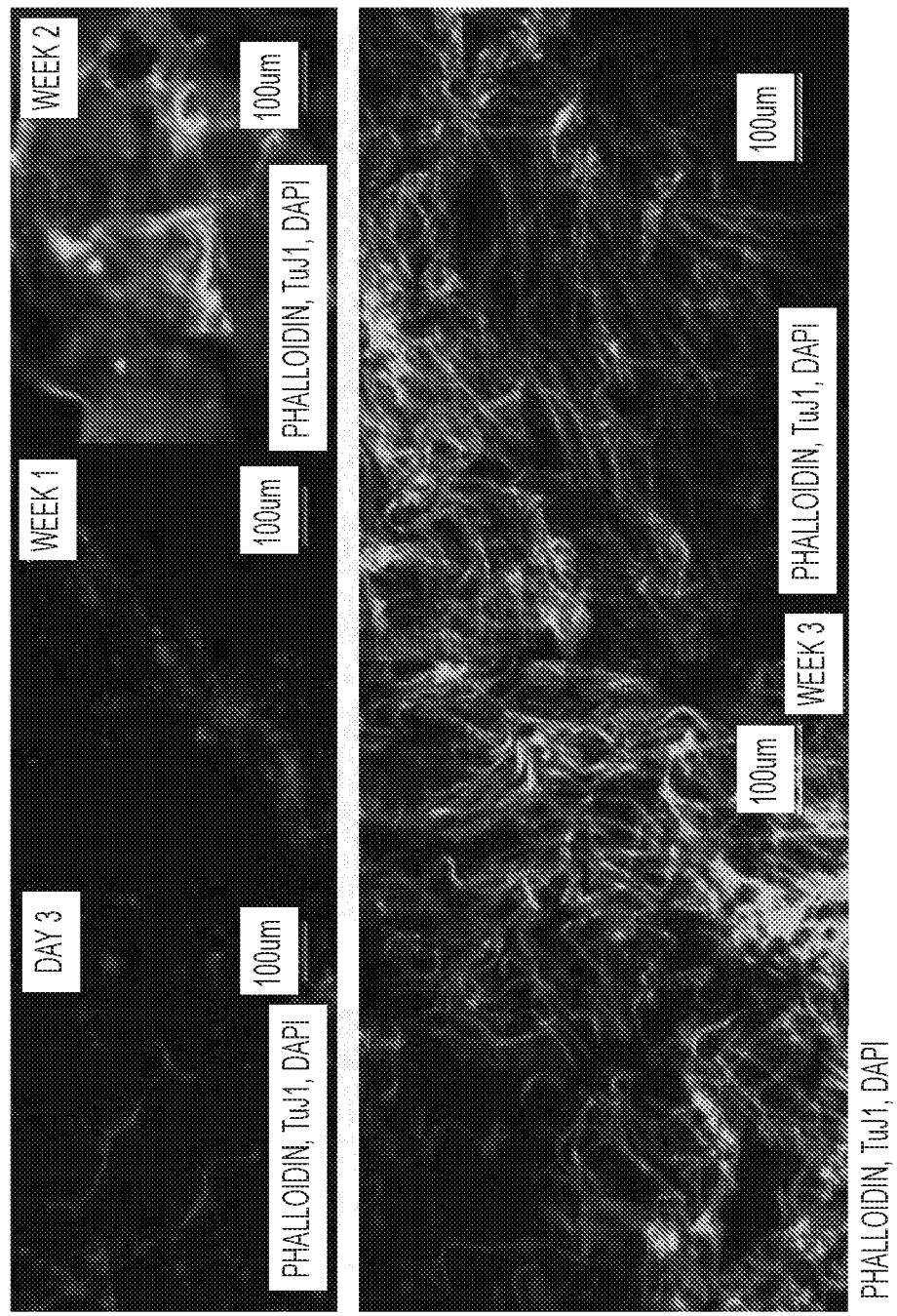
FIG. 19 shows exemplary photographs from certain provided embodiments. As is shown, when samples are sectioned horizontally, axonal connections from nerve may be resolved. However, when samples are imaged in a cross-section, axons are not immediately evident, though very intense antibody signal from nerve-dense areas are observed.
Figure 20:
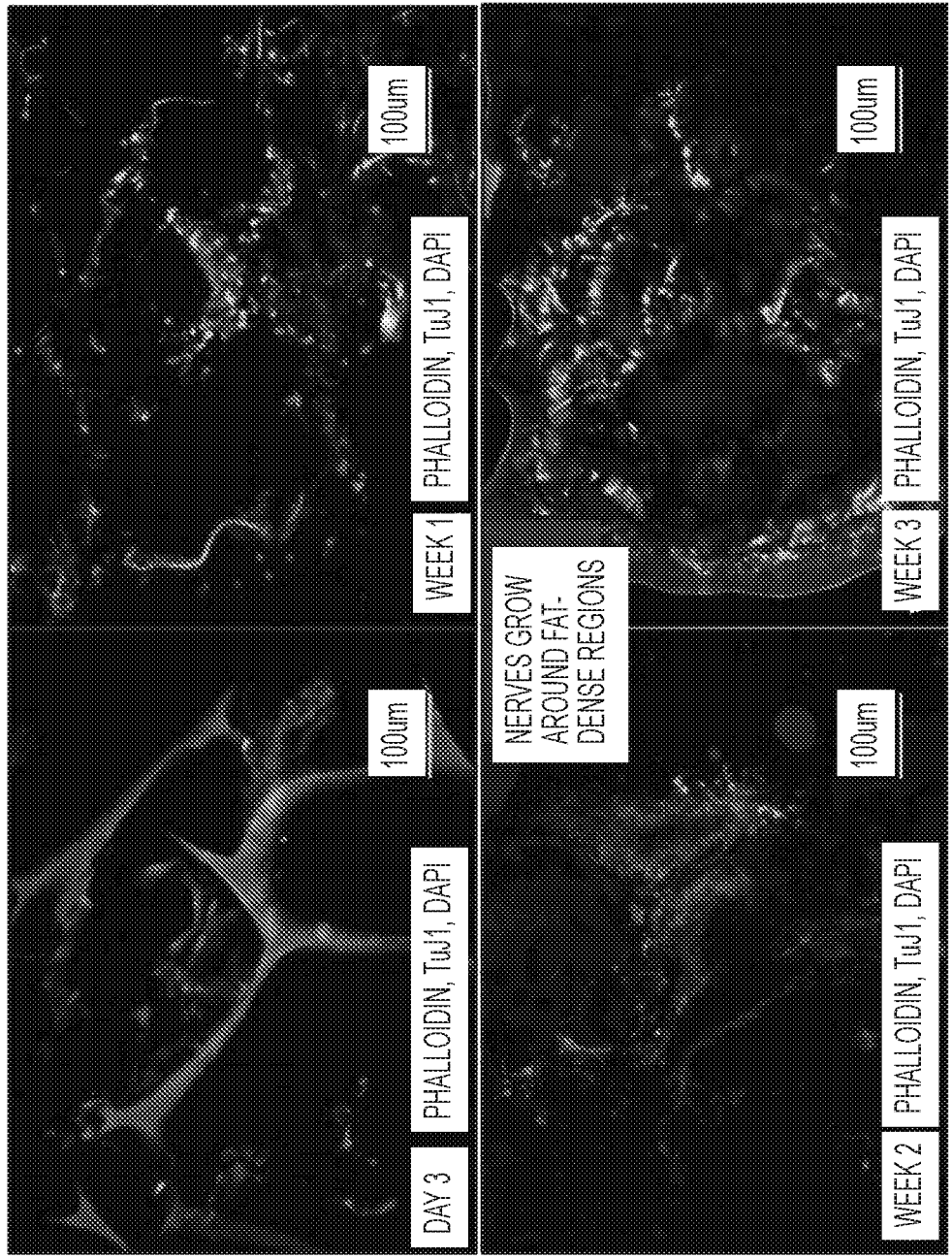
FIG. 20 shows exemplary photographs of hypodermal cross sections of certain embodiments after 3 days, 1 week, 2 weeks, or 3 weeks in culture. As shown, in some embodiments, nerves grow around, not through, lipid-droplet-dense regions.

Next, compositions were made similarly to those described above, except instead of a separate nerve gel layer, nerve cells were encapsulated in a collagen gel and coated over both sides of the hypodermis prior to assembly of the multi layered composition. As shown in FIG. 19, when horizontal sections of hypodermal layers coated in nerve gels were assessed via immunohistology, axonal connections are readily resolved by 2 weeks in culture. However, when cross-sections were assessed, as shown in FIG. 20, axons were not as noticeable, however, very intense signals from nerve dense areas were observed. It is of note, that the nerves appeared to grow around, not through, the lipid droplet dense regions of the hypodermal layer.

Example 2—Assessment of Biological Activity and Physical/Mechanical Characteristics of Provided Compositions In this example, multi layered compositions including a hypodermal layer that was coated in nerve gel, were assessed for biological function and certain physical/mechanical characteristics.

In order to characterize certain functional aspects of provided compositions, glycerol secretion, amounts of double stranded DNA, relative cytokine expression, and neuropeptide Y secretion were assessed.

Figure 21B:
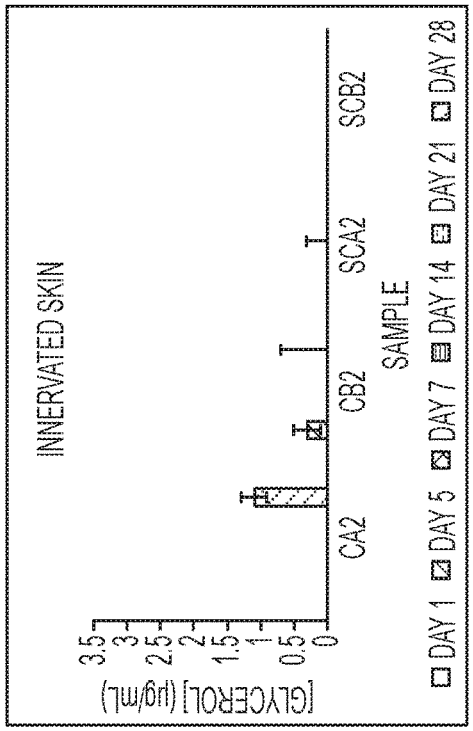
FIG. 21a-c shows glycerol secretion from certain exemplary embodiments and control conditions. 21a shows exemplary glycerol secretion from control skin compositions. 21b shows exemplary glycerol secretion from innervated skin compositions. 21c shows exemplary glycerol secretion from innervated skin compositions including a hypodermis layer.
Figure 21C:
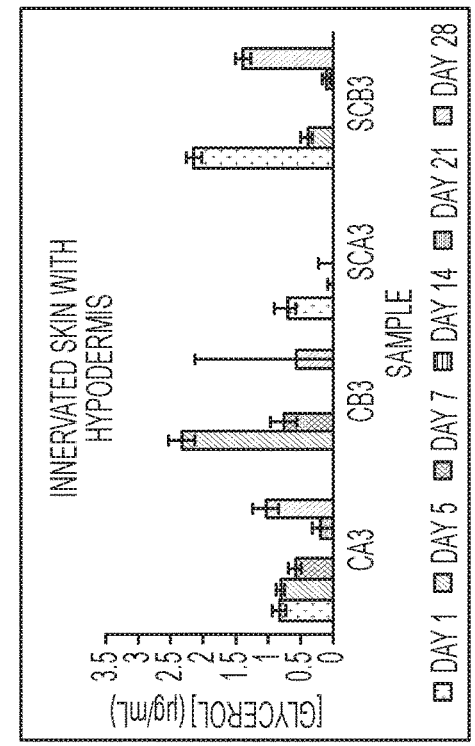
Figure 21A:
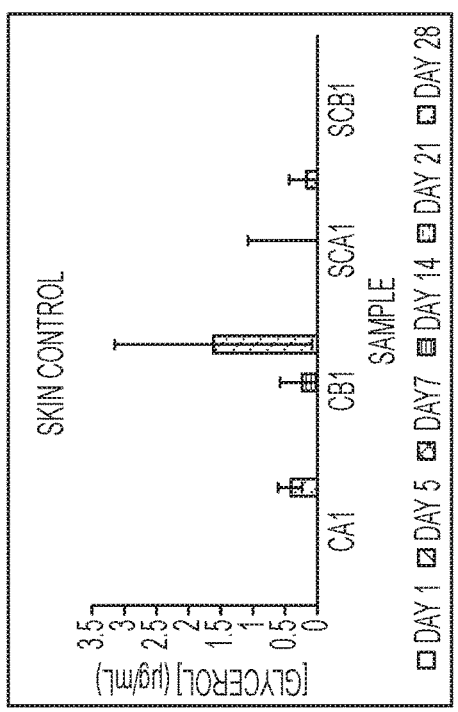

Glycerol secretion was measured for up to 28 days, in part, because this is an accepted manner of assessing function of the hypodermal layers. FIG. 21 shows an outline of the experiment as well as results for each of the skin control, innervated skin, and innervated skin with hypodermis groups. As is shown, the innervated skin with hypodermis groups exhibited significant glycerol secretion, with both silk fibroin-collagen and collagen-only compositions each exhibiting comparable levels of release. Without wishing to be held to a particular theory, it is possible that groups including keratinocytes exhibit a higher level of glycerol release than those that do not.

Double stranded DNA (dsDNA) was also assessed to verify viability and cellular proliferation within provided compositions for up to six weeks in culture. As shown in FIG. 22, in the skin control groups, there is only 1 layer (fibroblast gel with (B) and without (A) keratinocytes); compared to the innervated skin which has 2 layers, and the innervated skin with hypodermis which has 3. It is evident in FIG. 22 that with increased layers, there is a corresponding dampening of proliferation which may be due to both physical blocking of growth, as well as an increase in nutrient-limiting conditions. Additionally, particularly in SCA1 (silk-collagen no keratinocytes, skin control group) versus SCB1 (silk-collagen with keratinocytes, skin control group), there is a higher signal with respect to time up to 6 weeks. SCA1 is a fibroblast-only gel, SCB1 has a keratinocyte layer on the top of the gel, which seems to dampen proliferation. Additionally of note, the SC groups have much higher signal than the C groups, which we postulate is due to the enhanced growth conditions that the silk-collagen gels provide compared to collagen alone.

Figure 23:
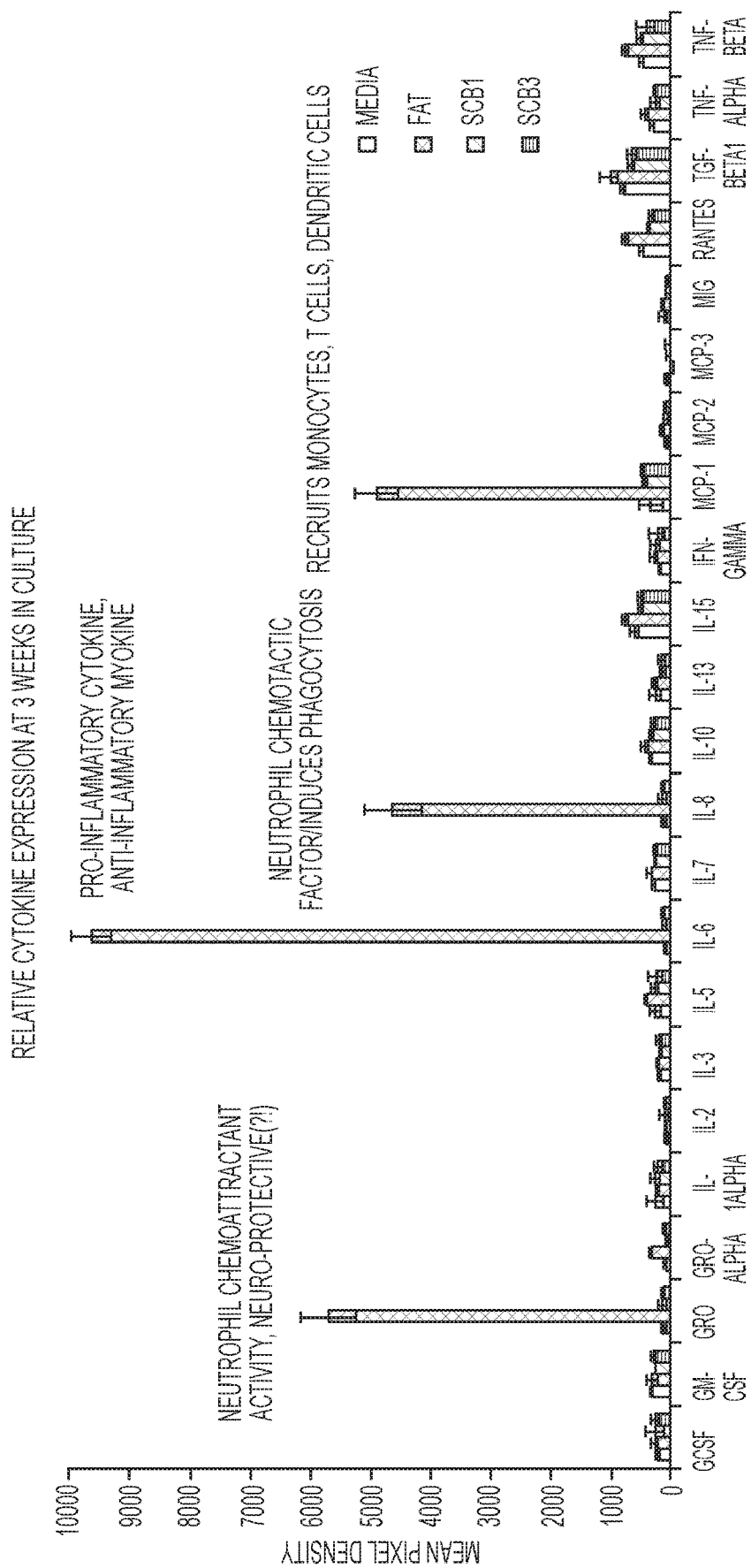
FIG. 23 shows an exemplary measure of cytokine expression for 23 cytokines from the following embodiments and controls silk-collagen composition, silk-collagen three-layer composition, a scaffold loaded with lipoaspirate (fat), and media only control.
Figure 24:
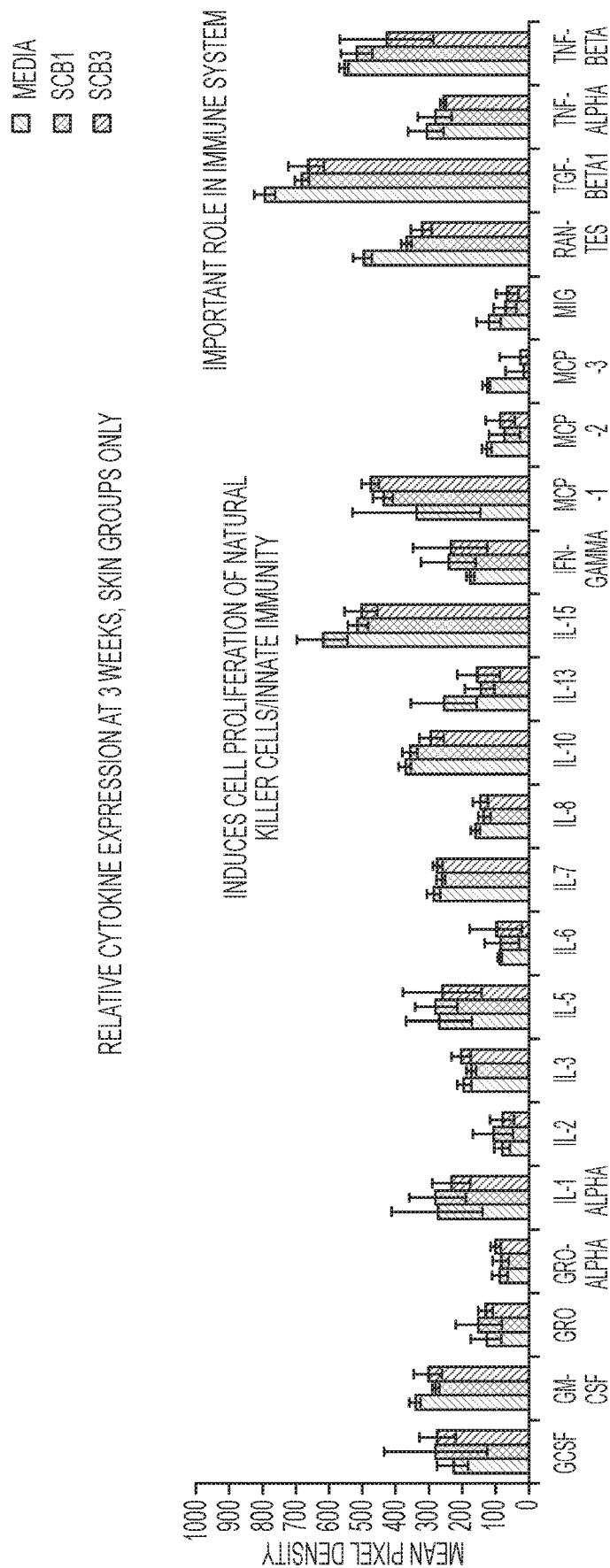
FIG. 24 shows an exemplary measure of cytokine expression for 23 cytokines from the following embodiments and controls silk-collagen composition, silk-collagen three-layer composition, and media only control.

In addition to assessments of glycerol secretion and viability/proliferation, an array of 23 human inflammatory cytokines were also assessed at 3 weeks in culture. FIGS. 23 and 24 show the results between three groups: 1) silk-collagen skin, 2) silk-collagen three-layer skin, and 3) a scaffold loaded with lipoaspirate (fat)). Significantly, it is observed that the fat scaffold expresses several inflammatory cytokines very strongly (GRO, IL-6, IL-8, MCP-1) which are noted in literature for adipose tissue. However, the skin groups, both skin only and the three-layered innervated skin were equivalent to the control (media only) group which suggests that the 3D models in standard culturing conditions may not express inflammatory cytokines, but the fat scaffold does. Thus, without wishing to be held to a particular theory, it is possible that the hypodermis to provided compositions allows for regulation of inflammation in the adipose tissue.

Neuropeptide Y was also assessed, in part, because it is known that neuropeptide Y is involved in skin function, adipose tissue growth, as well as involved in nociceptive neuron function.

Figure 25:
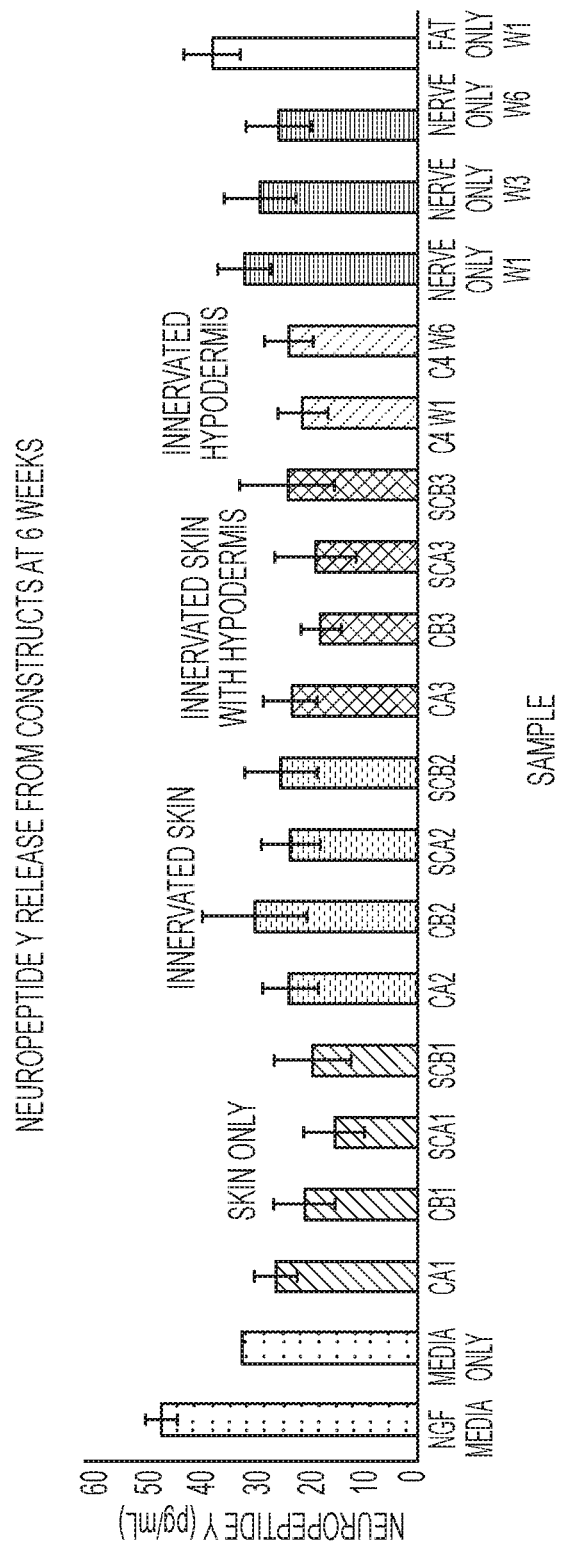
FIG. 25 shows an exemplary graph of neuropeptide Y expression across certain exemplary embodiments as well as certain control conditions.

Among the tested compositions (skin, innervated skin, innervated skin with hypodermis, innervated hypodermis, nerve only, and fat only) there was not a noticeable difference between groups, and all groups were essentially equivalent to the media only control groups (see FIG. 25). These results were achieved with the compositions in standard (unstressed) conditions, and, as such, are not unexpected.

Figure 26:
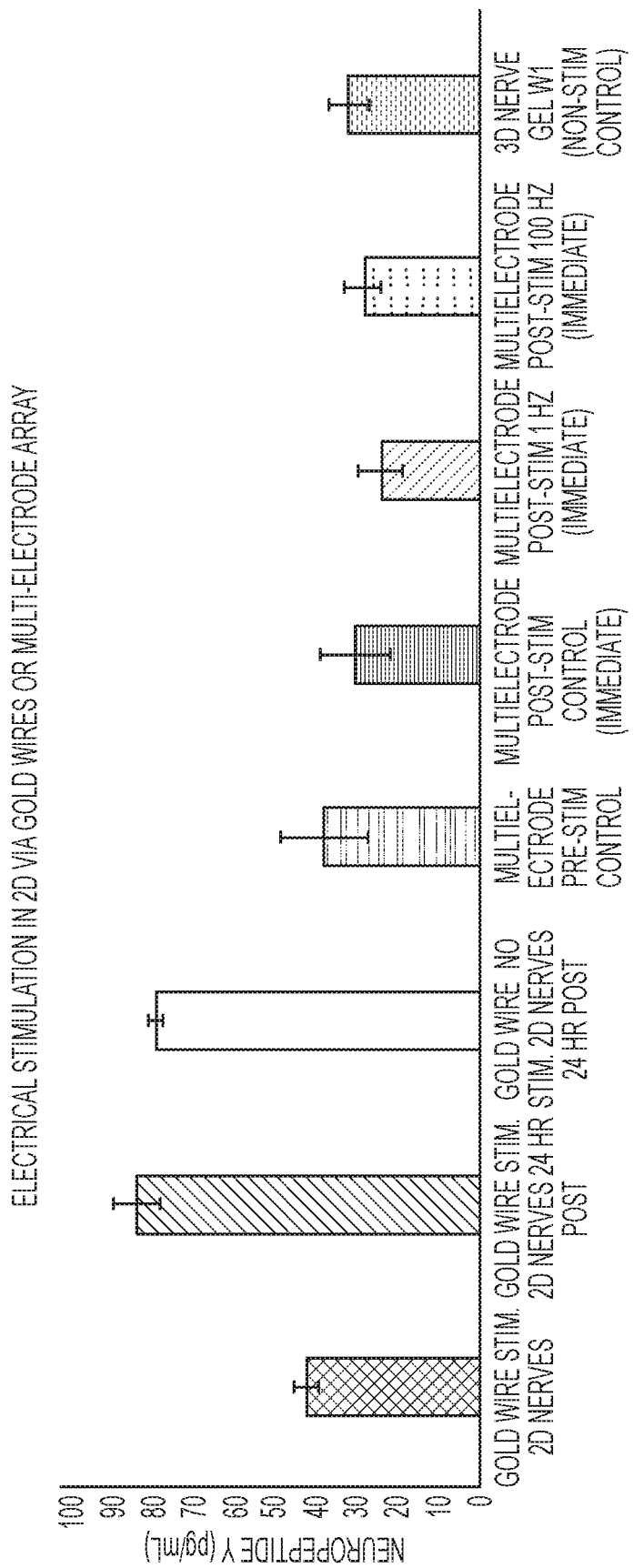
FIG. 26 shows an exemplary graph of neuropeptide Y expression across certain exemplary embodiments as well as certain control conditions, after electrical stimulation.

In order to assess the difference a stress makes on the neuropeptide Y release from provided compositions, electrical stimulation via 2D gold wires was used to assess certain groups. As shown in FIG. 26, in the stimulated conditions, there is a noticeable change in neuropeptide Y release before and after stimulation.

Figure 27:
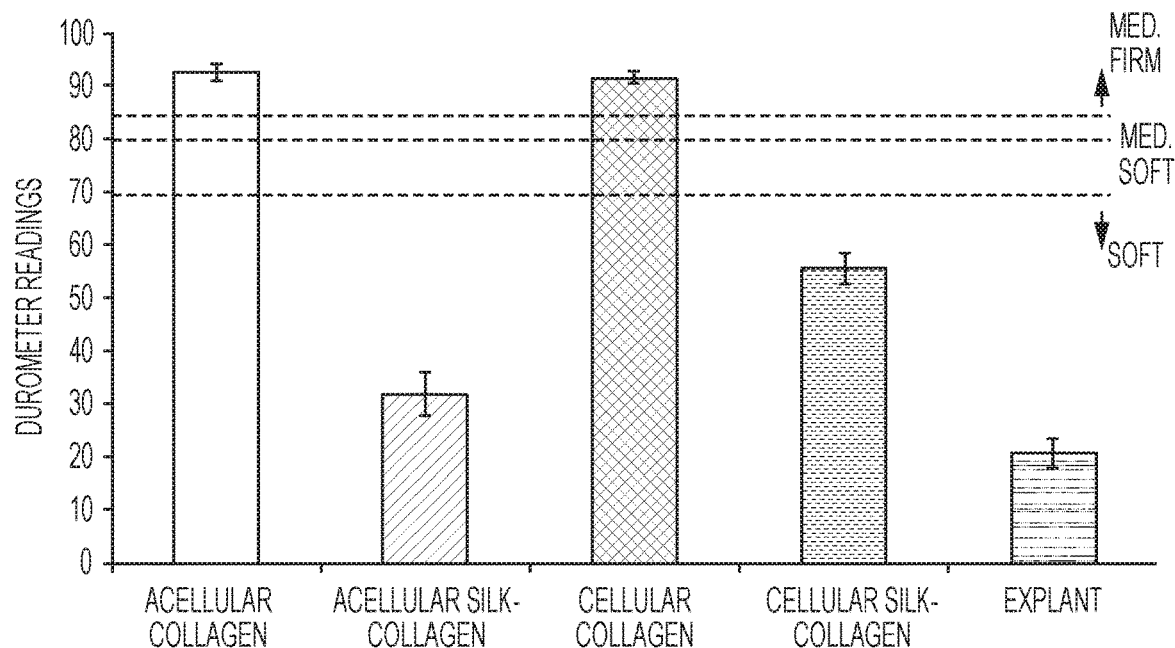
FIG. 27 shows an exemplary graph of Durometer reading Type OO or certain exemplary embodiments as well as certain control conditions as compared to a known control value for human skin.
Figure 27:
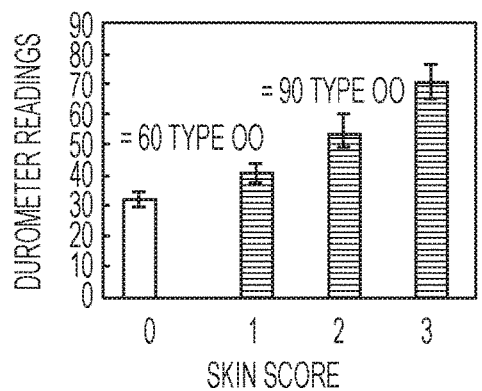

In order to characterize certain mechanical and/or physical properties of provided compositions, hardness, compressibility and stiffness of certain embodiments were measured. With regard to hardness, a durometer test was used, and the results shown in FIG. 27. Durometers are used, inter alia, to relate elastic and viscoelastic behavior of materials and have been used to measure dermal and epidermal changes via bulk properties. In this example, we tested durometer values of the tissues at 6 weeks in culture and found that silk-collagen dermis is more similar to human skin per Falanga (1993) than collagen-only dermis which is closer to diseased tissue. The silk-collagen construct was also more similar to explant readings than collagen constructs. The size disparity between silk-collagen and collagen may have had an effect on the readings as collagen shrinks to ~0.5 mm while silk-collagen was 2.2 mm thick.

Figure 28:
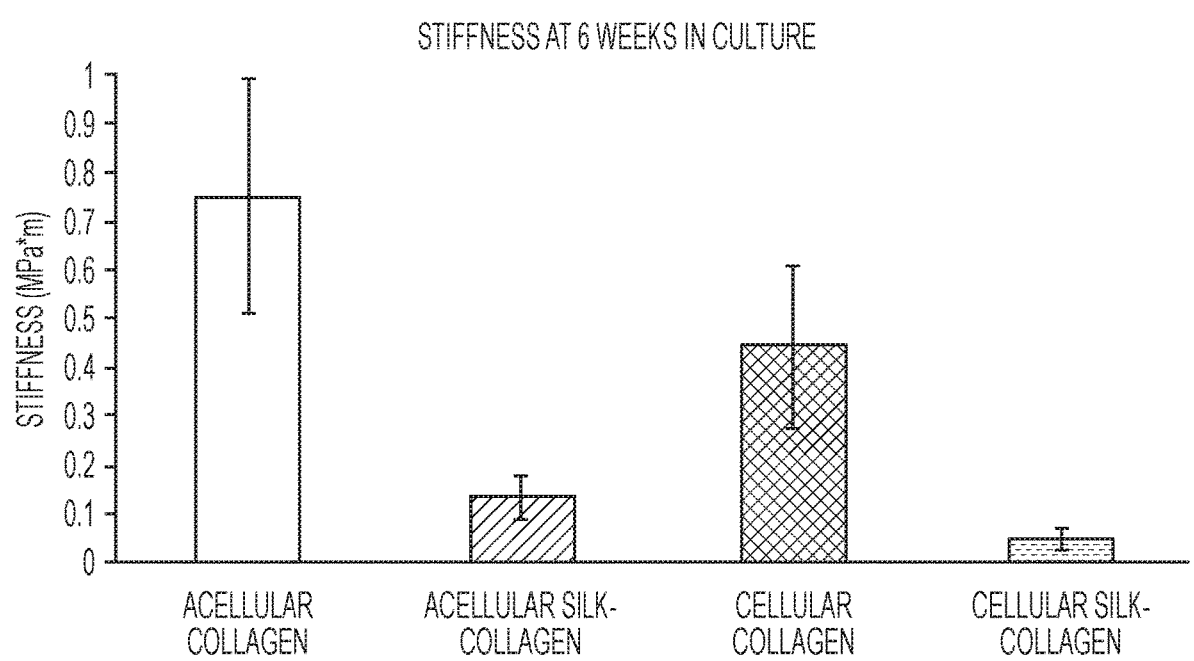
FIG. 28 shows an exemplary graph of stiffness values for certain embodiments as compared to collagen only controls.

Compressibility of certain compositions were also assessed and the data is shown in FIG. 28 and in Table 4 below:

TABLE 4

Young's Modulus and Stiffness

| Sample | Young's Modulus (kPa) | ±SD | Stiffness (MPa*m) | ±SD |
|---|---|---|---|---|
| cellular collagen | 8.399 | 1.950 | 0.751 | 0.237 |
| Acellular silk-collagen | 8.994 | 2.740 | 0.136 | 0.044 |
| Cellular collagen | 6.069 | 1.895 | 0.444 | 0.164 |
| Cellular silk-collagen | 2.464 | 0.688 | 0.049 | 0.017 |

In this example, stiffness was measured as follows:

$$\text{stiffness } (Pa*m) = \frac{E(Pa) * \text{cross sectional area}(m^2)}{\text{initial thickness}(m)}$$

The trends noted via the durometer test above were maintained in this compressive analysis. Silk fibroin-collagen compositions are significantly less stiff in both acellular and cellular conditions compared to collagen only compositions.

Figure 29:
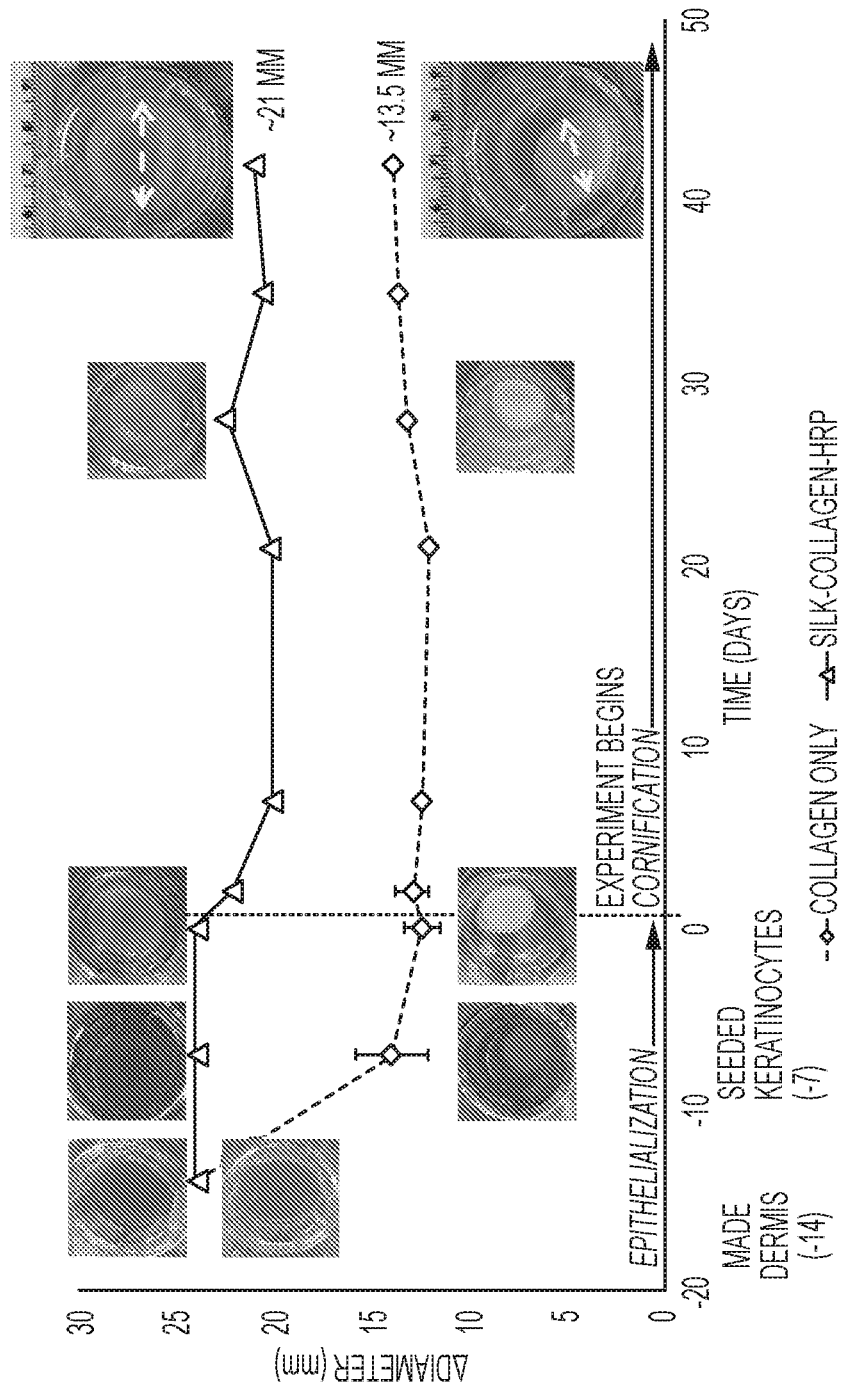
FIG. 29 shows an exemplary timeline and photographs of physical changes in certain embodiments over time as compared to collagen only controls.

Lastly, an assessment of the contractibility and water retention capability of certain embodiments was made. As is shown in FIG. 29, silk fibroin-collagen dermis compositions do not contract as much as collagen only compositions do, resulting in a much thicker (2.2 mm versus 0.5 mm) dermis layer as well as a much larger diameter (21 mm versus 13.5 mm) by 6 weeks in culture. It appears that this corresponds to an increase in syneresis in the collagen-only gels, meaning that the silk-collagen dermis gels have an enhanced ability to retain moisture with time. Without wishing to be held to a particular theory, it is possible that this finding relates to at least some, if not all, the functional and morphological differences we have found, and propose that provided silk-collagen skin is an improvement upon the collagen-only system.

Example 3—Electrical Stimulation of Certain Provided Compositions

Figure 30:
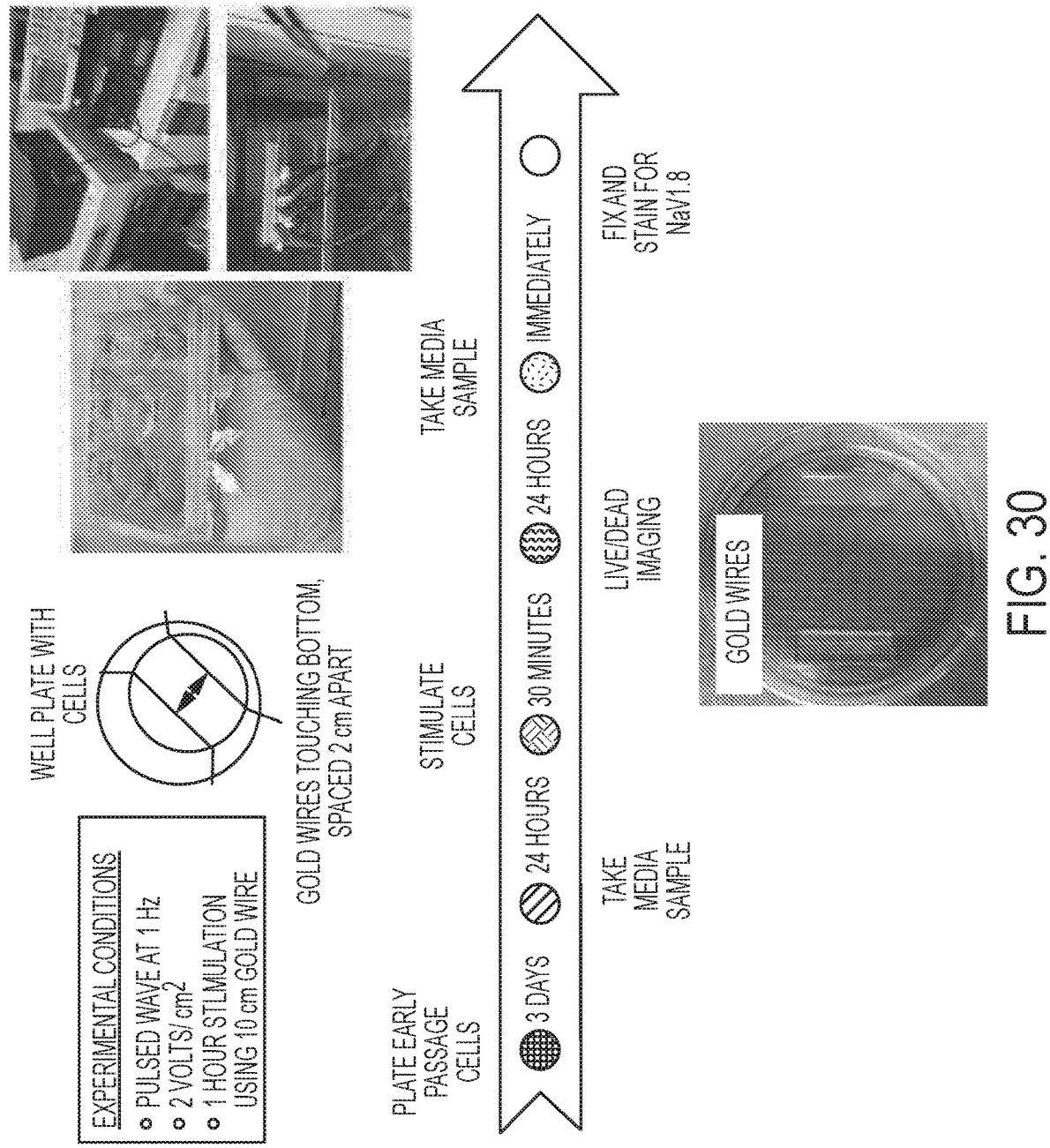
FIG. 30 shows a flow chart and photographs of certain exemplary provided methods. Specifically.

An outline of this example may be found in FIG. 30. Specifically, in this Example, fibroblasts, keratinocytes, and nerve cells were seeded in a monolayer and stimulated via gold wires and a function generator at 1 Hz for one hour (2 volts/cm), and media was collected before stimulation, 24 hours after stimulation, and 48 hours after stimulation for ELISA analysis of NAV1.8. Live/dead staining was performed immediately after stimulation.

Figure 31:
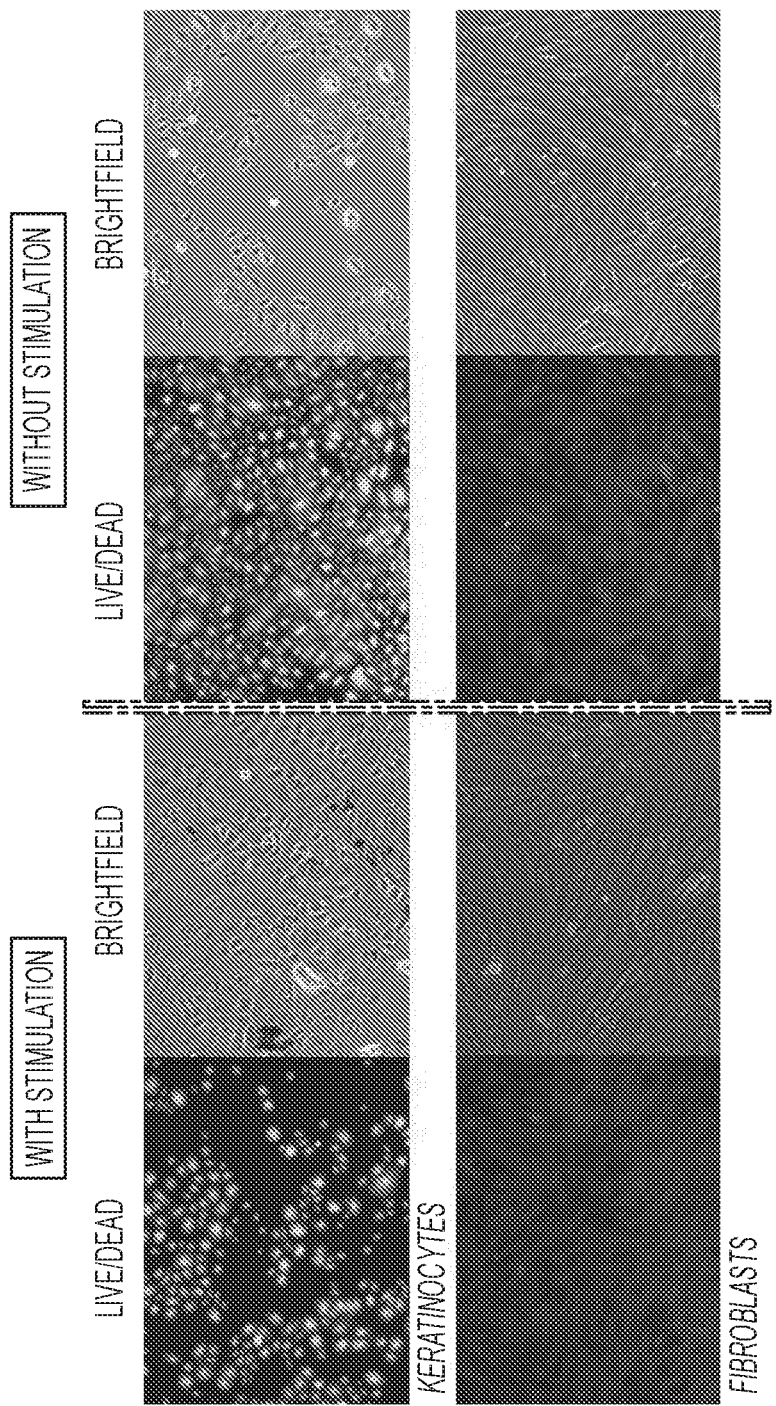
FIG. 31 shows exemplary photographs of live/dead staining of monolayer cells after electrical stimulation. Specifically, live/dead staining was performed on monolayer cells following 1 hour of electrical stimulation at 1 Hz (~1.5-2 volts/cm). Keratinocytes and fibroblasts were mostly alive after stimulation, though keratinocytes did experience some cell death via membrane explosion but this does not stain with DEAD.

FIG. 31 shows the live/dead staining that was performed on monolayer cells following 1 hour of electrical stimulation at 1 Hz (~1.5-2 volts/cm). Keratinocytes and fibroblasts (both skin cell types used in the compositions of this example) were mostly alive after stimulation, though keratinocytes did experience some cell death via membrane explosion but this does not stain with DEAD.

Figure 32:
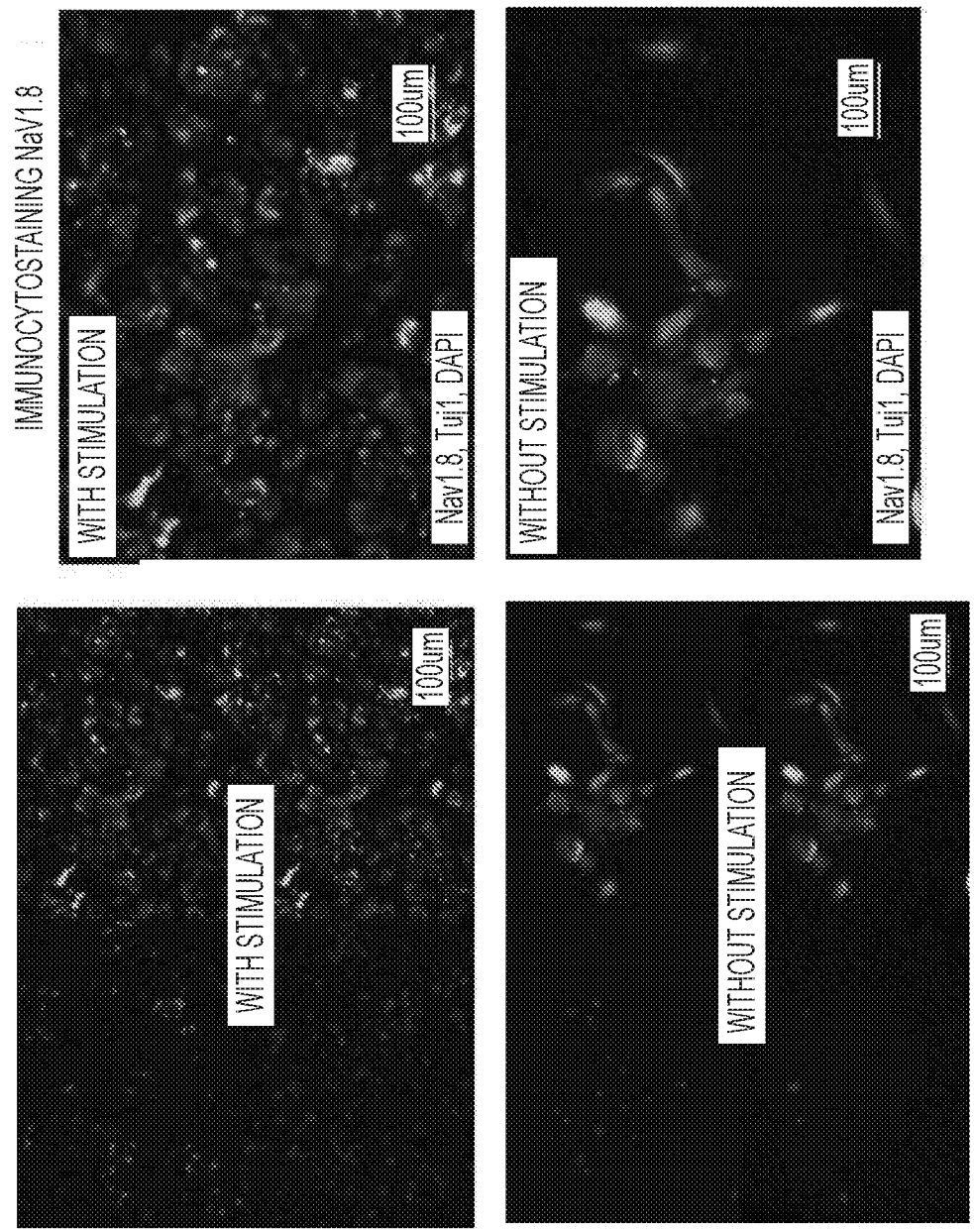
FIG. 32 shows exemplary photographs of NaV1.8 staining of hiNSCs electrically stimulated for an hour at 1 Hz, as compared to non-stimulated control.

NaV1.8 is a sodium channel associated with acute and chronic pain expressed by nociceptive neurons. In this Example, the presence or absence of NaV1.8 channels was assessed in order to better understand the potential properties of provided innervated compositions. FIG. 32 shows that one hour of stimulation at 1 Hz results in a greater NaV1.8 signal as compared to non-stimulated controls.

Figure 33:
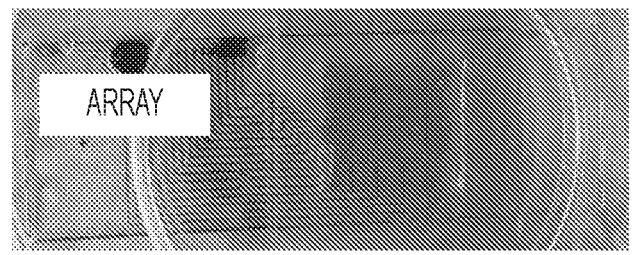
FIG. 33 shows exemplary photographs of NaV1.8 staining of hiNSCs that were stimulated for 1 hour at either 1 Hz or 100 Hz. As is shown, there are clear differences between the groups. Nerves at 100 Hz are very dense and NaV1.8 is detectable at every cell; however, 1 Hz nerves and control groups have very sparse signal from NaV1.8.
Figure 33:
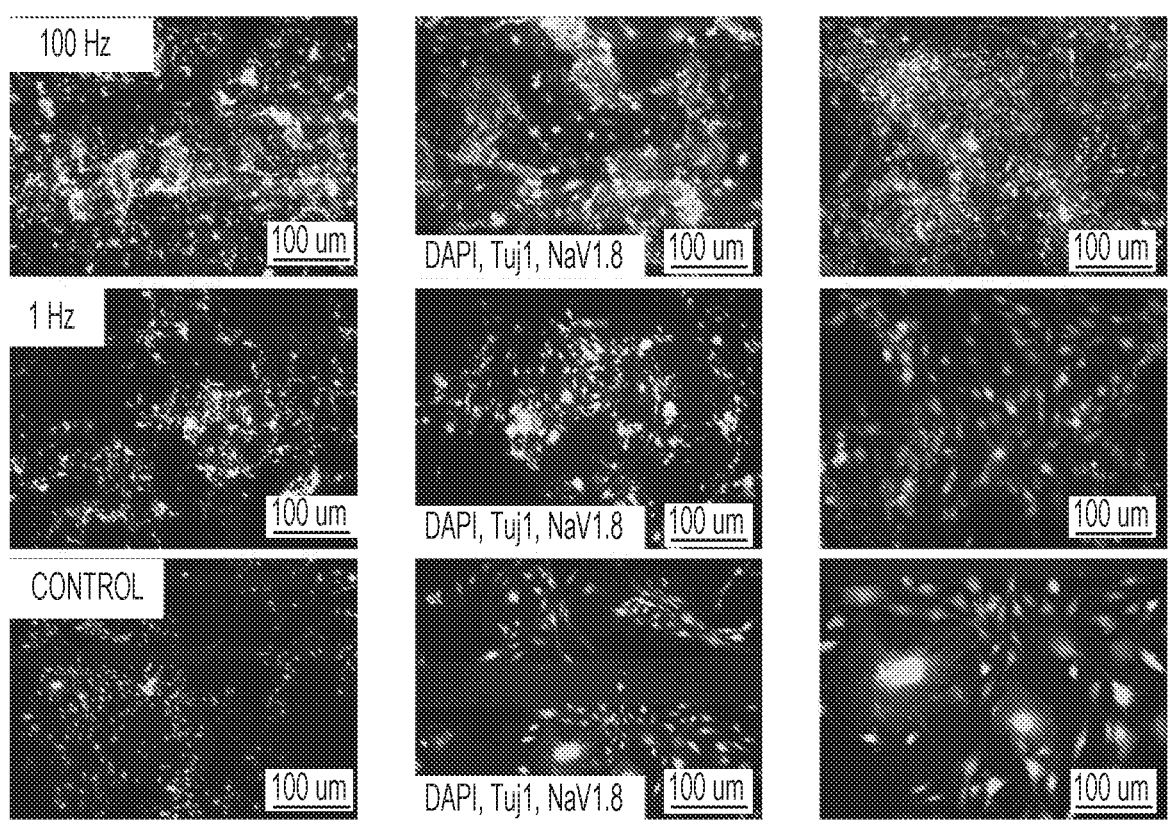

Additionally, the effects of stimulation for one hour at 1 Hz versus at 100 Hz on NaV1.8 expression was assessed. FIG. 33 shows that there were clear differences between hiNSCs that were stimulated for 1 hour at 1 Hz as compared to those stimulated at 100 Hz. Specifically, nerves at 100 Hz are very dense and NaV1.8 is detectable at every cell; however, 1 Hz nerves and control groups have very sparse signal from NaV1.8. FIG. 33 also shows an exemplary array embodiment compatible with some aspects of the present invention.

Figure 34:
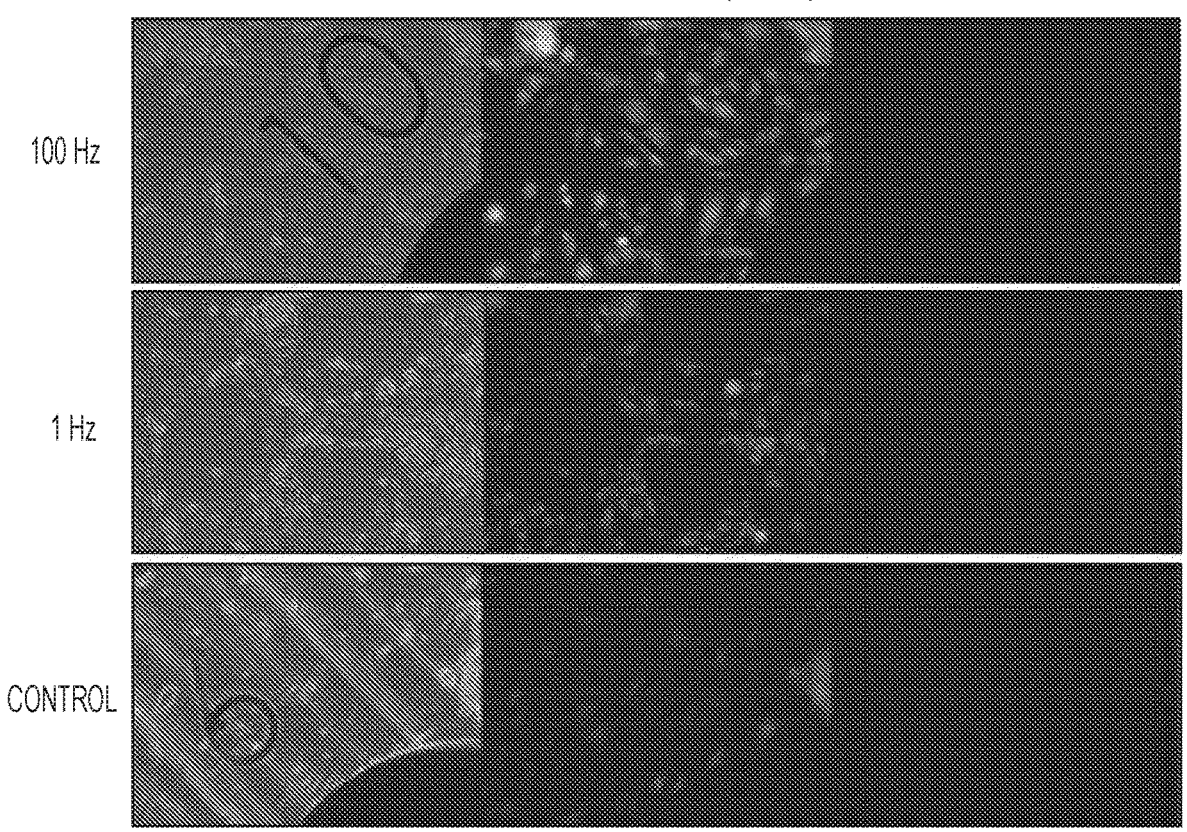
FIG. 34 shows photographs of exemplary live/dead staining of hiNSC after 1 week in culture, after electrical stimulation at 1 Hz, 100 Hz, or no stimulation (control). Dead stain is far right column, live is middle, brightfield is left.

Live/dead staining results for hiNSCs that were stimulated for 1 hour at 1 Hz as compared to those stimulated at 100 Hz are shown in FIG. 34. Dead stain is in the far right column, live is in the middle column, and brightfield view is shown on the left.

Example 4—Exposure of Provided Composition to Simulated Inflammation Via Lipopolysaccharide In this Example, certain provided compositions are exposed to a known inflammatory stimulus, namely lipopolysaccharide, in order to assess the response of the cells therein, including potentially immune cells in the lipoaspirate used in some embodiments. The methods used in this Example are as described above, including in FIG. 4, until 1 week after the constructs are raised to the air-liquid interface. On that day, control samples were dosed with 100 µL PBS to the surface of the skin (hypodermis samples, which are immerged in media, were dosed into the media); 5 µg/mL LPS is dosed to low LPS' groups, and 50 µg/mL were dosed to 'high LPS' groups. Samples were incubated with the treatment for 24 hours, at which point media samples were collected and the constructs were taken out of culture.

TABLE 5

Nomenclature for Example 4

| Abbreviation | Name | Description |
| --- | --- | --- |
| SCB1 | Full thickness skin without hypodermis | Two-layered silk-collagen gel with fibroblasts and keratinocytes (dermis/epidermis) |
| SCB3 | Full thickness skin with innervated hypodermis | Three-layered construct with innervated hypodermis beneath dermis/epidermis silk-collagen gel |
| Hypod./Hyperderm. | Hypodermis | Porous, HFIP/salt-leached silk scaffold with human lipoaspirate |

Figure 35:
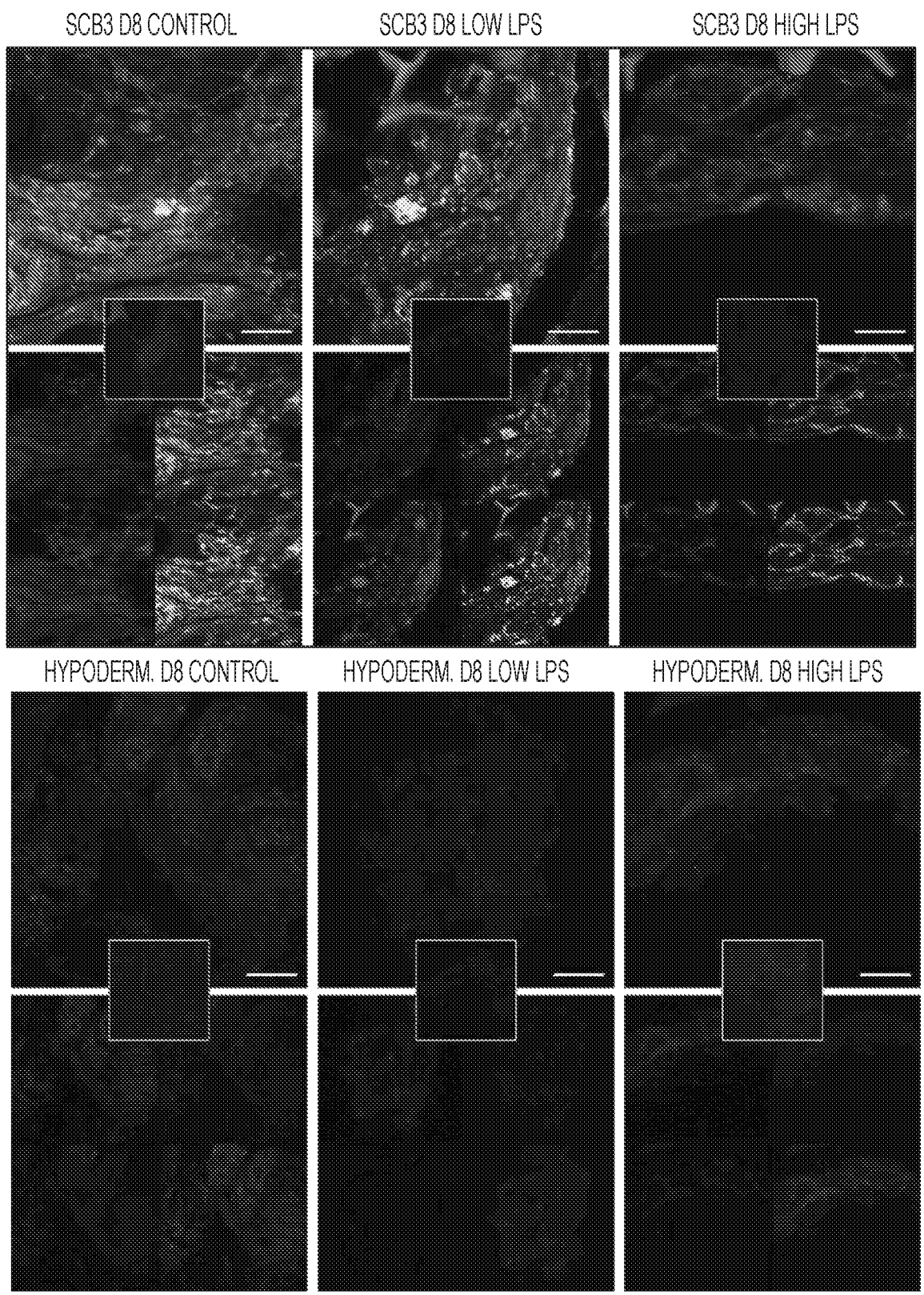
FIG. 35 shows exemplary photographs illustrating the effects of lipopolysaccharide (LPS) on hypodermis with and without innervation. For the images on row 1 (top row), shown are 3 average projections obtained via confocal microscopy. For the images in row 2, they are 4 selected overlay images from z-stack. Scale 100 µm; blue DAPI (nuclei), green βIII Tubulin (mature neuron marker), red CD68 (macrophage). Inset images are no primary antibody control. Rows 3 and 4 show images of hypodermis, with no substantial signal indicating the presence of neurons or high presence of immune cells, suggesting that the addition of hiNSCs to the hypodermis (row 1) enhances the survivability of immune cells in the adipose tissue, and that neural networks form in SCB3 groups but are not apparent in the hypodermis by itself.

As is shown in FIG. 35, SCB3 (full thickness hypodermis with innervation) samples demonstrated densely innervated networks which form in the pores of the silk-scaffold, and often around lipid droplets (SCB3 D8 low LPS, row 1). Without wishing to be held to a particular theory, it is contemplated that exposure to even low levels of LPS may affect axonal growth. Also as shown in FIG. 35, hypodermis samples (as received, without added hiNSCs) have no apparent nerves and low CD68 levels by day 8 in culture (one week after the constructs are raised to the air-liquid interface, plus 24 hours of exposure to LPS). Low levels of CD68 appear to indicate the presence of no, or very few, cells of macrophage lineage. Row 1 images were produced from 3 average projections via confocal microscopy. Row 2 images are 4 selected overlay images from z-stack. Scale 100 µm; blue DAPI (nuclei), green βIII Tubulin (mature neuron marker), red CD68 (macrophage). Inset images are no primary antibody control.

Figure 36:
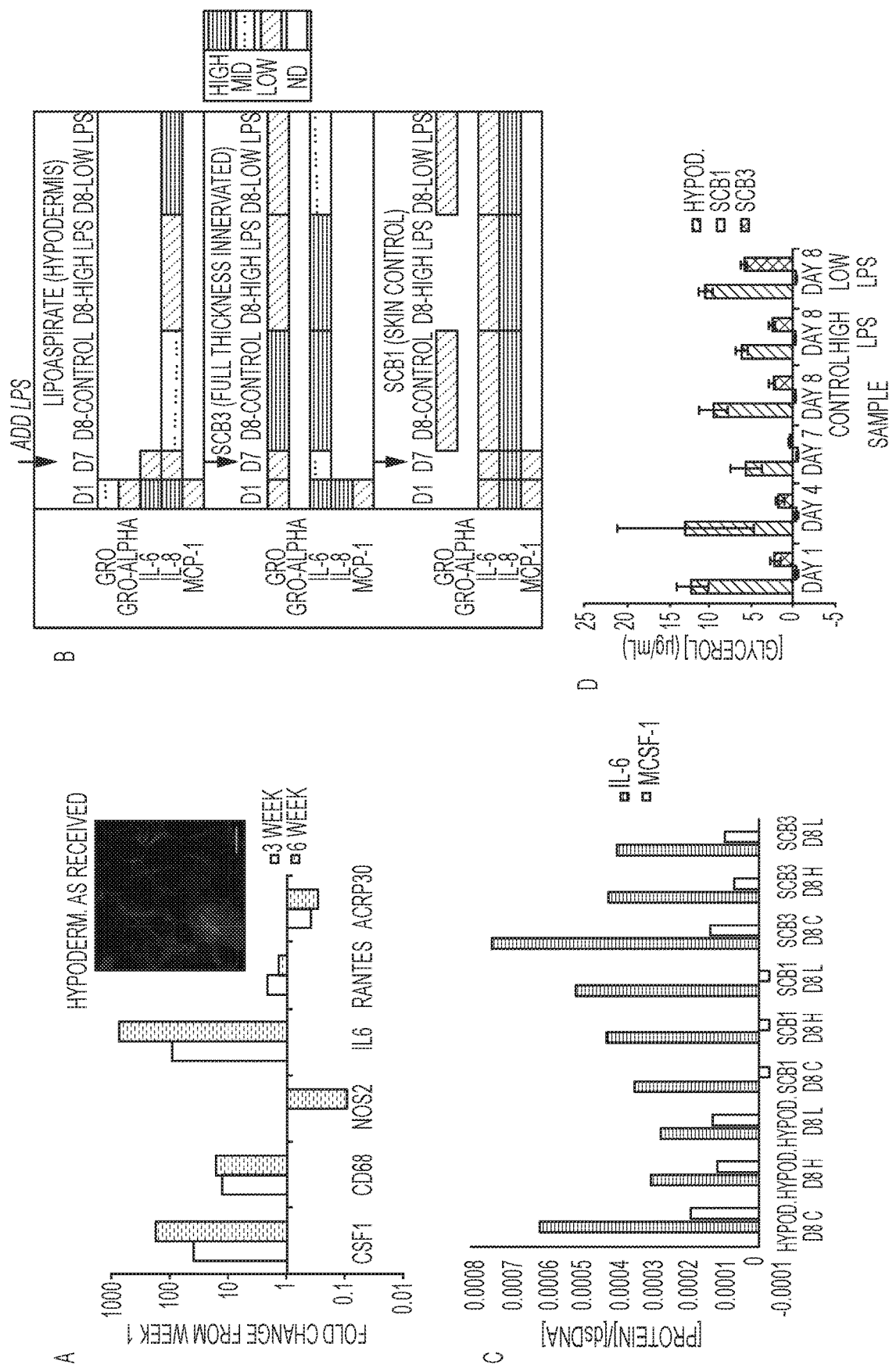
FIG. 36 shows exemplary graphs describing the gene and protein expression of several measures of inflammatory or other stress of certain provided compositions after exposure to LPS. Panel A) qPCR of hypodermis (patient 1) with time up to 6 weeks. CSF1 and CD68 are macrophage markers, NOS2, IL-6, RANTES are pro-inflammatory, and ACRP30 is an adipose marker. Samples were normalized to OS-9 a human control gene, and are presented as fold change from week 1. Inset image is of the hypodermis after 3 days in culture stained with DAPI and CD68 (scale 100 µm) which suggests there are immune cells initially present in the lipoaspirate. Correspondingly, CSF1 and CD68 are highly expressed with time. Panel B) A 23-target human inflammatory cytokine array was performed to determine differences in cytokine secretion with time and with respect to LPS treatment. In the hypodermis (which uses lipoaspirate from patient 3), day 1 has the highest cytokine secretion overall. IL-6 secretion increased from the control in the hypodermis, but when normalized to dsDNA concentration (see panel C) high and low concentration of LPS have equivalent IL-6. SCB3, unlike the hypodermis, secreted GRO (GRO alpha, beta, and gamma) which is a cytokine expressed by macrophages, epithelial and neutrophils. SCB1 also expresses GRO to a lesser extent and the signal is non-detectable under high LPS treatment. Panel C) Secretion of IL-6 (pro-inflammatory cytokine) and MCSF-1 (human macrophage colony-stimulating factor) normalized by dsDNA concentration. IL-6 decreases in the hypodermis and SCB3 upon exposure to high and low levels of LPS, a trend which is reversed in SCB1 (which does not have immune cells). Similarly, the hypodermis and SCB3 show decreases in MCSF-1 upon LPS exposure at both concentrations; whereas in SCB1 there is no signal. Panel D) Glycerol secretion from the hypodermis (without innervation) is relatively constant with time and LPS application; however, SCB3 groups demonstrate slight increase in glycerol secretion upon exposure to low concentration of LPS, but remains constant at high concentrations compared to the control.

Quantitative Analysis of LPS on Innervated Full Thickness Skin Compared to Skin Only and Hypodermis Only Groups As is shown in FIG. 36, in panel A, hypodermis was assessed via qPCR for the expression of macrophage markers (CSF1 and CD68), pro-inflammatory genes (IL6, RANTES, and NOS2), and an adipose marker, ACRP30. Samples were normalized to OS-9 a human control gene, and are presented as fold change from week 1. Inset image is of the hypodermis after 3 days in culture stained with DAPI and CD68 (scale 100 µm) which suggests there are immune cells initially present in the lipoaspirate. Correspondingly, CSF1 and CD68 are highly expressed with time.

Also as shown in FIG. 36, in panel B, a 23-target human inflammatory cytokine array was performed to determine differences in cytokine secretion over time and with respect to LPS treatment. In the hypodermis (which was derived from lipoaspirate by soaking a porous silk sponge in lipoaspirate tissue from a human sample), day 1 has the highest cytokine secretion overall. IL-6 secretion increased from the control in the hypodermis, but when normalized to dsDNA concentration (see panel C) high and low concentration of LPS have equivalent IL-6. SCB3, unlike the hypodermis, secreted GRO (GRO alpha, beta, and gamma) which is a cytokine expressed by macrophages, epithelial and neutrophils. SCB1 also expresses GRO to a lesser extent and the signal is non-detectable under high LPS treatment.

In panel C, FIG. 36 shows secretion of IL-6 (pro-inflammatory cytokine) and MCSF-1 (human macrophage colony-stimulating factor) normalized by dsDNA concentration. IL-6 decreases in the hypodermis and SCB3 upon exposure to high and low levels of LPS, a trend which is reversed in SCB1 (which does not have immune cells). Similarly, the hypodermis and SCB3 show decreases in MCSF-1 upon LPS exposure at both concentrations; whereas in SCB1 there is no signal.

In panel D, FIG. 36 shows glycerol secretion from the hypodermis (without innervation) is relatively constant with time and LPS application; however, SCB3 groups demonstrate slight decrease in glycerol secretion upon exposure to high concentration of LPS, but increases at low concentrations of LPS as compared to the control.

In this Example, it is shown that SCB3 groups (with innervation) all have signal from nerve (green βIII tubulin) whereas the hypodermis samples do not—meaning that there is not nerve present in the hypodermis, at least by the time the experiment takes place (typically 3 weeks post-abdominoplasty). It is also shown that SCB3 groups show consistent signal of CD68 (there is some auto-fluorescent background between all groups), seeming to cluster around densely populated areas. However, the hypodermis without innervation by day 8 does not show CD68 signal (see FIG. 36, panel A inset for the hypodermis as received). Without wishing to be held to a particular theory, it is possible that the combination of cell types included in SCB3 (all skin cells, hiNSCs, adipose cells, etc.) enhance the survivability/ presence of the CD68+ cells.

Figure 37:
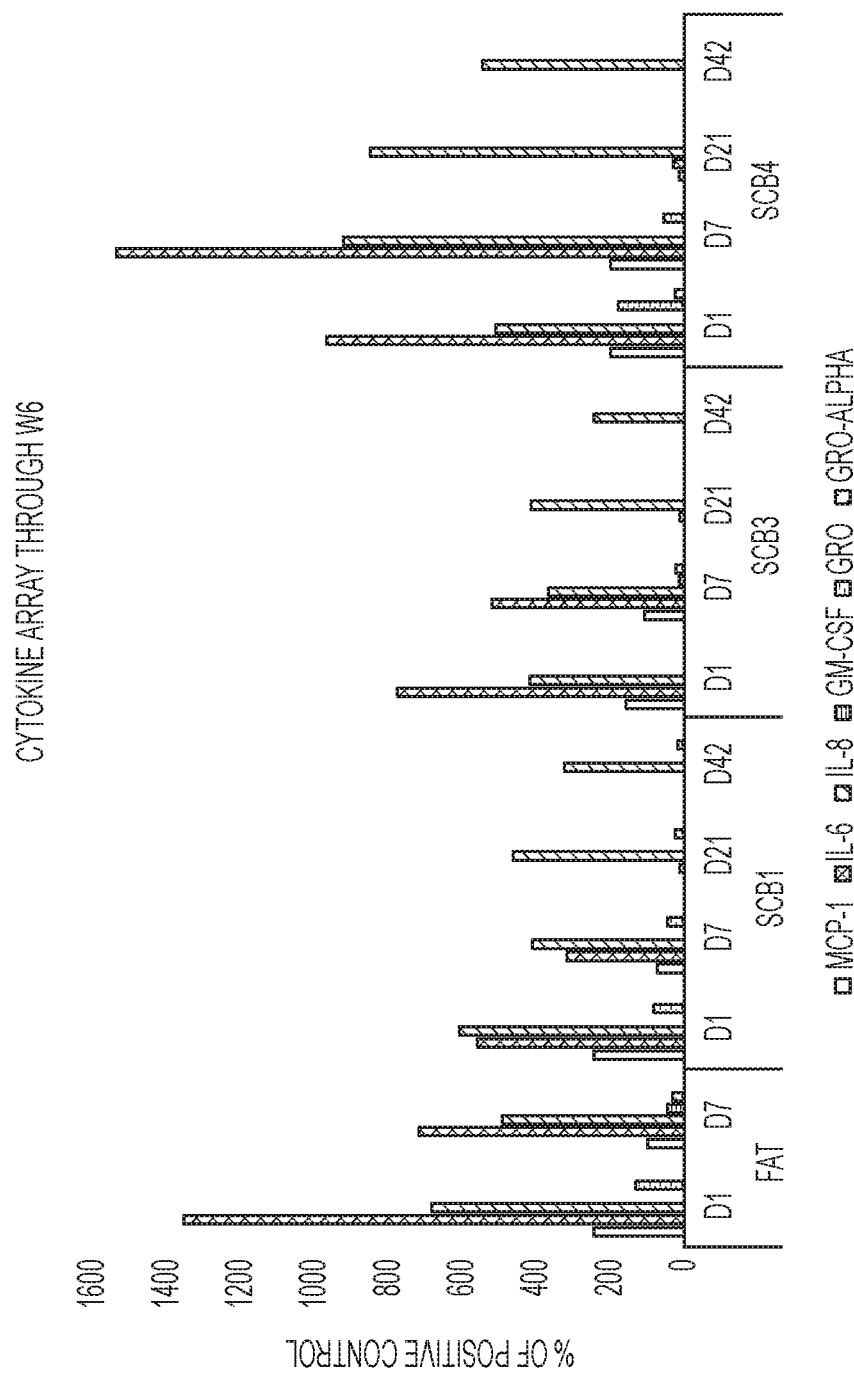
FIG. 37 shows a graph of the expression of certain cytokine genes including MCP-1, IL-6, GM-CSF, GRO, and GRO-alpha by certain provided compositions over 6 weeks (42 days, i.e., D42) as compared to positive control (biotin-conjugated IgG printed directly onto membrane). Conditions: Fat=hypodermis only, SCB1=full thickness skin composition without hypodermis, SCB3=full thickness skin composition with innervated hypodermis, SCB4=full thickness skin composition with hypodermis but without nerve cells.

FIG. 37 shows the results of a cytokine array run on samples of hypodermis (labeled "fat" in FIG. 37), SCB1, SCB3, and SCB4 (which is a full thickness skin+hypodermis model without nerve cells added). In general, IL-6 expression appears to decrease over time out to 6 weeks across all sample/model types. IL6 expression is highest in fat (hypodermis) alone and SCB4 (full thickness skin+ hypodermis model without nerve added)—lowest in SCB1 (skin alone i.e. keratinocytes and fibroblasts only)—but in SCB3 (full thickness skin+hypodermis+nerve added), IL6 is slightly lower than fat and SCB4 and decreases with time suggesting that neuro-modulation of inflammation may be occurring. FIG. 37 also shows that MCP1, a monocyte chemoattractant protein, is secreted amongst all groups with immune cell presence (i.e. all except SCB1) and that the level of expression is lowest in SCB3 (with nerve). An additional observation is that the highest level of IL-6 expression in all groups is at D1 and D7, and by day 42 (D42) the level of signal is mostly diminishing or gone, suggesting that this may be due to the development of a more stabilized system.

Figure 38:
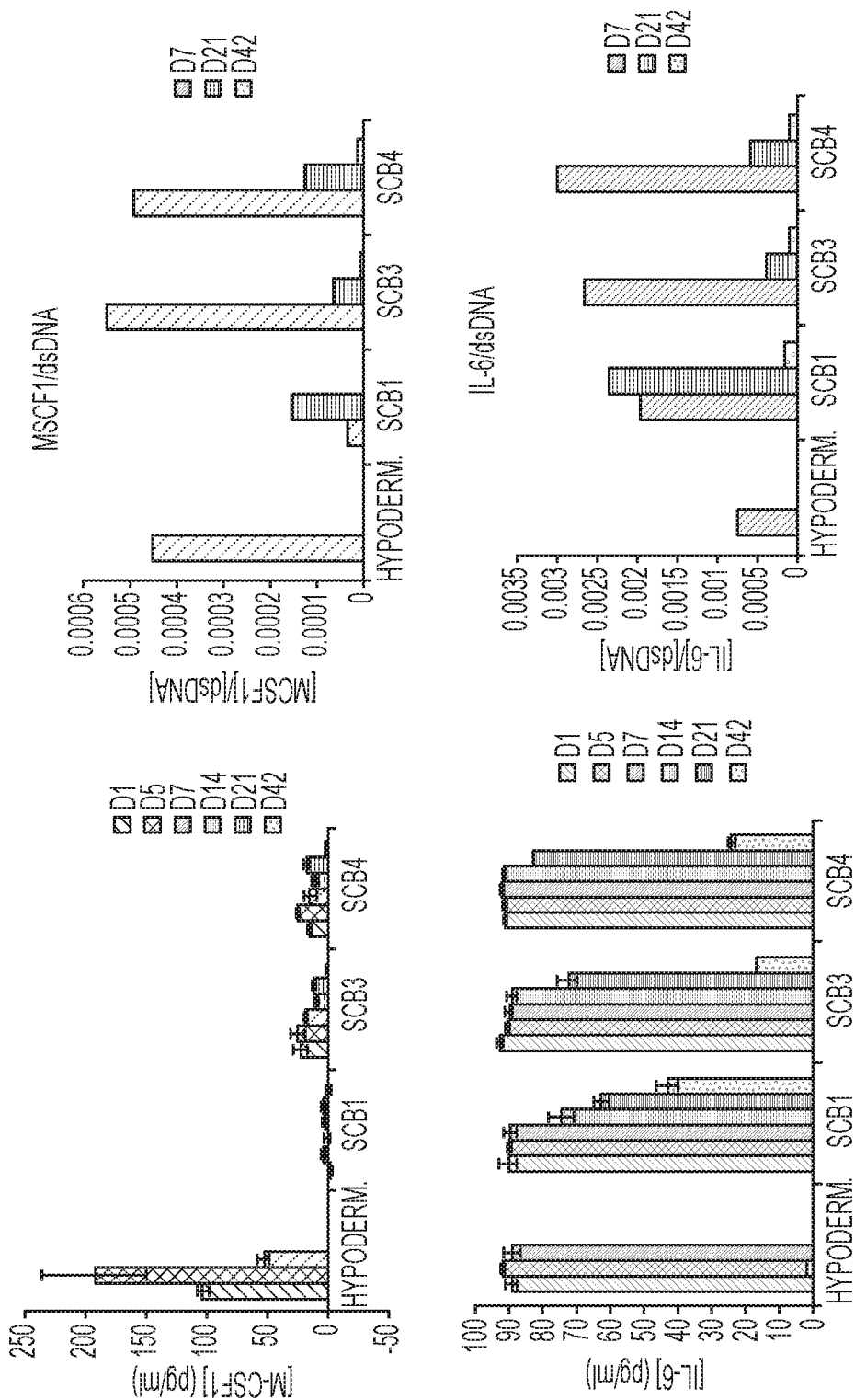
FIG. 38 shows exemplary graphs of expression of MCSF1 or IL-6 protein in certain provided compositions. The left most panels reflect raw expression data, while the right most panels reflect the expression data as a function of the double stranded DNA (dsDNA) in the sample. Conditions—"Hypoderm"=hypodermis only, SCB1=full thickness skin composition without hypodermis, SCB3=full thickness skin composition with innervated hypodermis, SCB4=full thickness skin composition with hypodermis but without nerve cells.

FIG. 38 shows enzyme-linked immunosorbent assays (ELISAs) array run on samples of hypodermis (labeled "Hypoderm." in FIG. 38), SCB1, SCB3, and SCB4 to detect the presence of IL-6 or MSCF1 protein (leftmost panels) as well as those levels as a function of the amount of dsDNA in the sample (rightmost panels). As shown in FIG. 38, MCSF1 macrophage colony stimulating factor was present in groups with immune cells (all except SCB1), and MCSF1 levels were lower in skin groups than in the hypodermal (fat only) control. Additionally, it was observed that IL-6 expression was high in all groups and decreased with time to day 42 (D42), as was observed in FIG. 37 at the nucleic acid level. Again, by D42, IL-6 expression is lowest in the SCB3 group.

Figure 39:
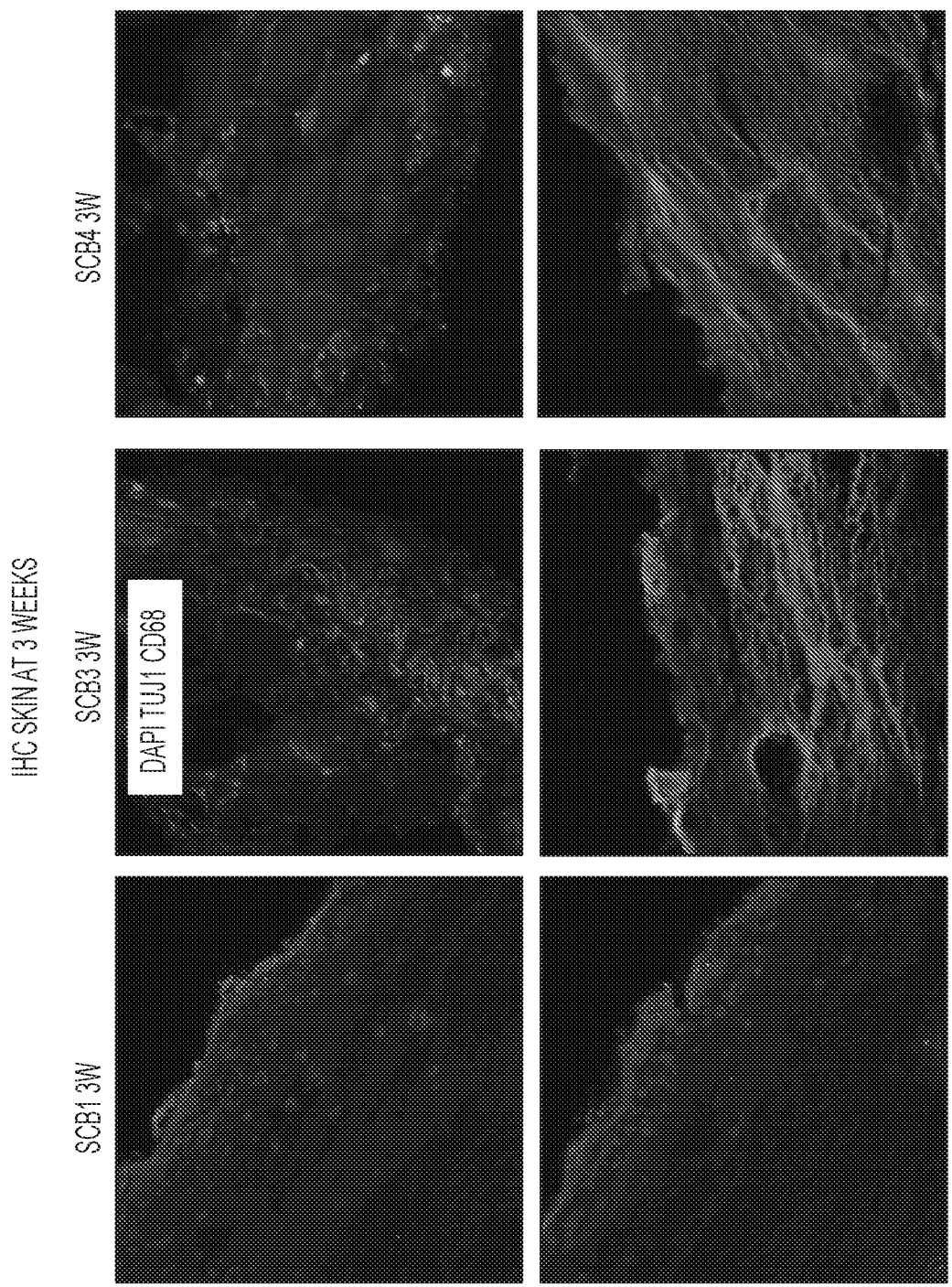
FIG. 39 shows exemplary photographs generated from immunohistochemical (IHC) assessment of certain SCB1, SCB3, and SCB4 compositions after 3 weeks in culture. Samples were stained for DAPI, TUJ1 (neuronal marker) and CD68 (macrophage marker). Images were taken at 20× magnification and scale is 100 µm. Conditions—SCB1=full thickness skin composition without hypodermis, SCB3=full thickness skin composition with innervated hypodermis, SCB4=full thickness skin composition with hypodermis but without nerve cells.

FIG. 39 shows representative photographs of immunohistochemistry of certain provided compositions at 3 weeks of samples assessed for the presence and level of each of CD68, TUJ1 and DAPI. It was found that nerve cells appeared to be present in skin models at hypodermis (top row, except SCB1 which is dermal/epidermal only) and epidermis (bottom row). Additionally, it appears that some neural networks may have formed in SCB3 and there also appeared to be some CD68 signal. Images were taken at 20× magnification, scale was 100 μm.

Figure 40:
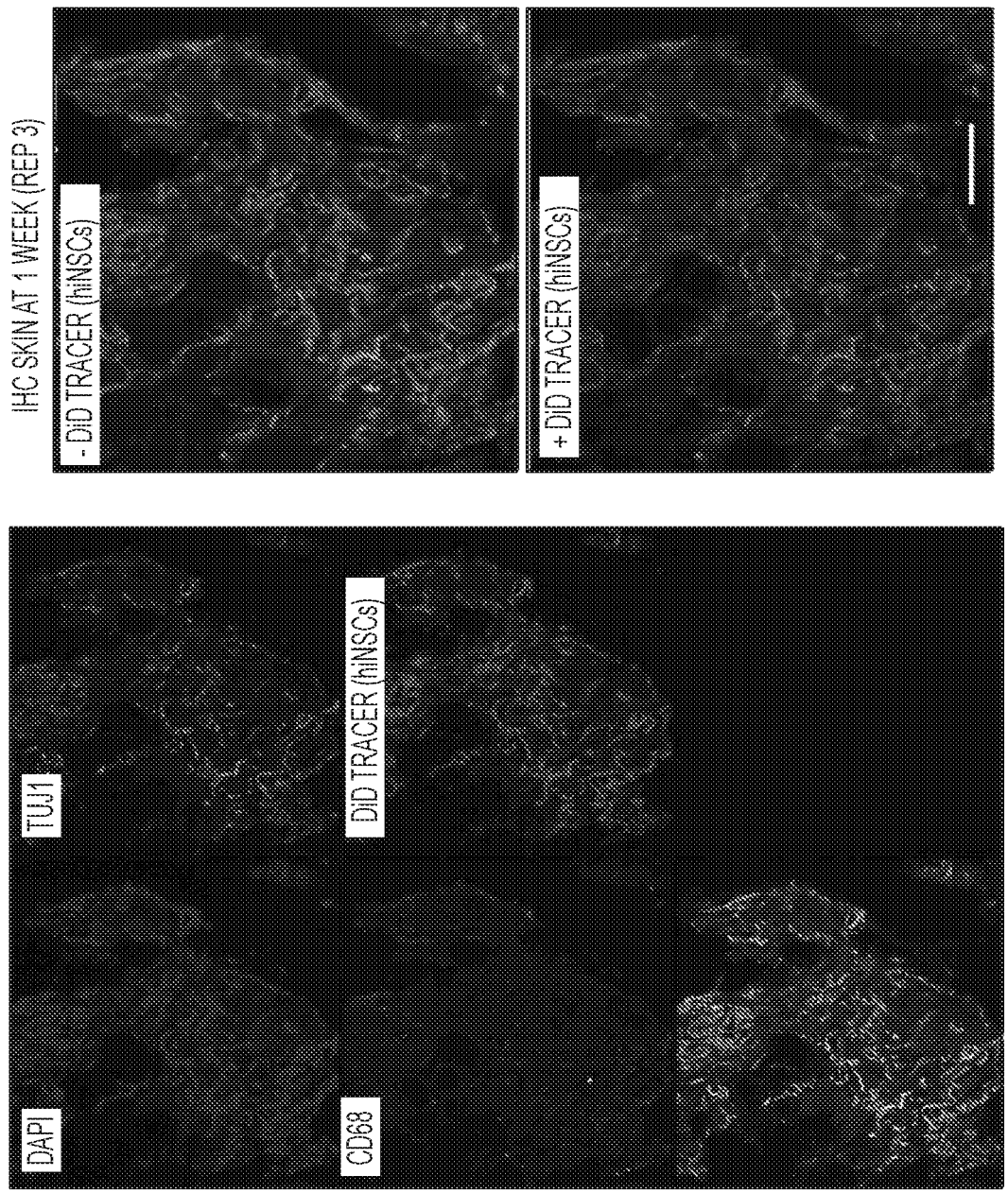
FIG. 40 shows exemplary photographs of immunohistochemical analyses of certain provided compositions. The lipophilic carbocyanine tracer DiD (ThermoFisher) was added to certain provided compositions and the development of neuronal networks was observed via Tuj1 staining. Scale is 100 µm.

In order to assess whether the nerve cells observed developed in the provided compositions or if they instead came from the adipose tissue that was added, a tracer (DiD, ThermoFisher, diluted 1:1000 in PBS) was added to hiNSCs in culture prior to seeding into SCB3 samples. Then, the DiD-labeled hiNSCs were added to SCB3 samples in the same standard method as described in FIG. 5. FIG. 40 shows that hiNSCs, when incubated with a tracer (DiD), exhibited overlapping signal with TUJ1, therefore the nerve networks seen in the images in FIG. 39 and FIG. 40 are very likely the nerves added to the skin model, not any nerves which may have been in the adipose tissue (patient inherent/tissue inherent).

Physical/Mechanical Properties

Figure 41:
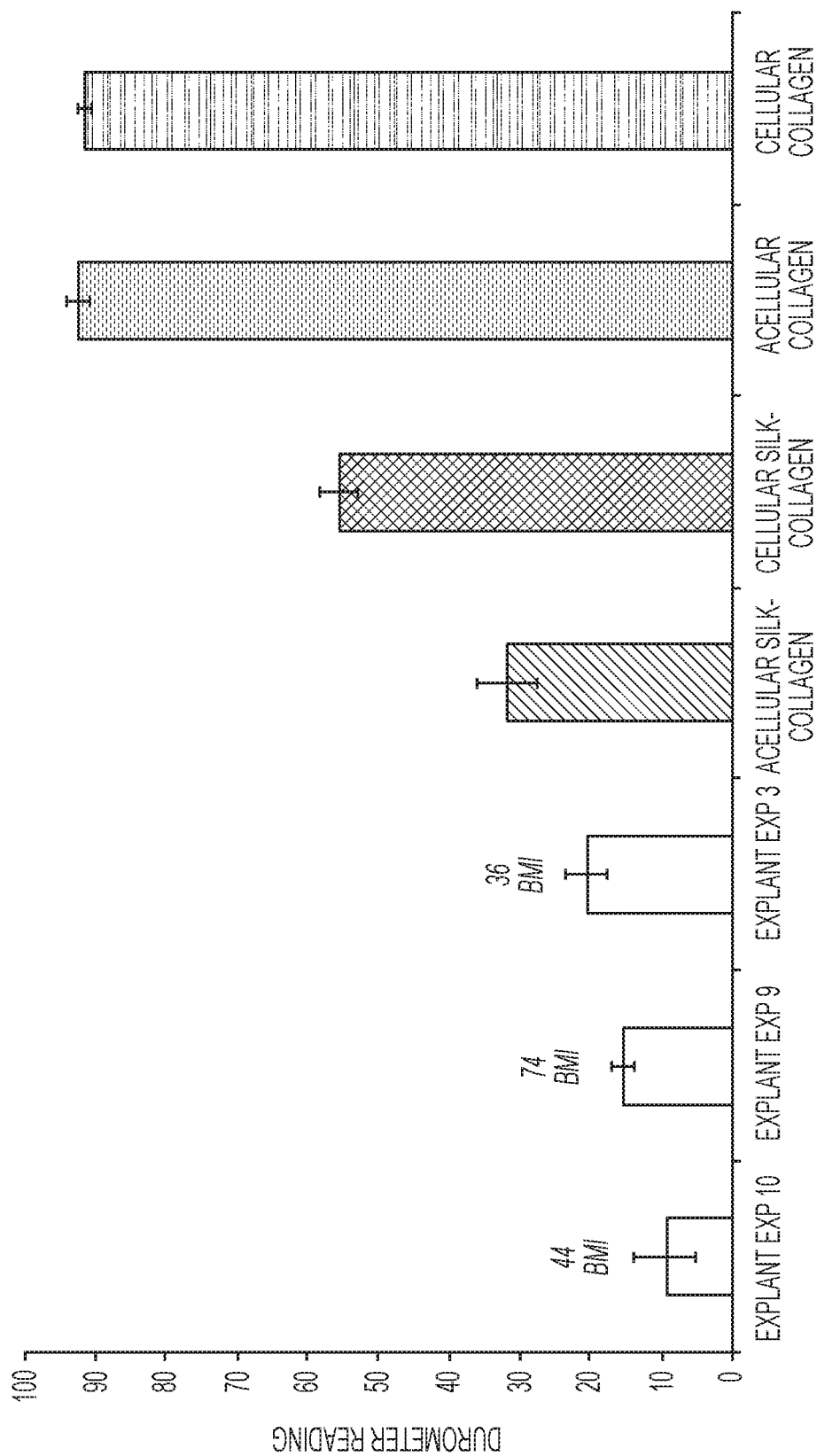
FIG. 41 shows a graph of hardness values for several donated hypodermal samples (explants) as well as scaffolds of various protein/polymer compositions.

FIG. 41 shows hardness measurements of various hypodermal/explant sample of individuals with different body mass indexes as compared to that of scaffolds made from various forms of silk and/or collagen. From the data shown, silk-collagen blends surprisingly seem to best mimic native tissue.

In order to further assess differences between collagen only scaffolds and silk-collagen blends, the mass loss over time of each type of scaffold was compared. Briefly, for silk-collagen samples, 2.166 mL of 60 minute boil silk (6-8% w/v silk) was added tp 2.166 mL of 3 mg/mL bovine collagen type 1 (same as in previous methods, Advanced Biomatrix), then 1.688 mL of 1×DMEM (Fisher), 21.6 uL HRP type IV (Sigma) and 21.6 uL of 1% $H_2O_2$ (Sigma) were combined and gently mixed. Conditions were the same for collagen-only sample, except 4.332 mL of collagen was added to 1.668 mL of 1×DMEM, rather than the silk and collagen. In both cases, 1.5 mL of either silk-collagen or collagen was added to a 12-well transwell plate after the transwell had been weighed empty. Samples were allowed to fully gel (up to 12 hours) at 37° C. Once samples were gelled they were weighed. Then, 1×DMEM was added to the transwell (1.5 mL bottom and 0.5 mL top) and the sample was weighed again after 1 hour. Then the sample was weighed with time until the end of experiment.

Figure 42:
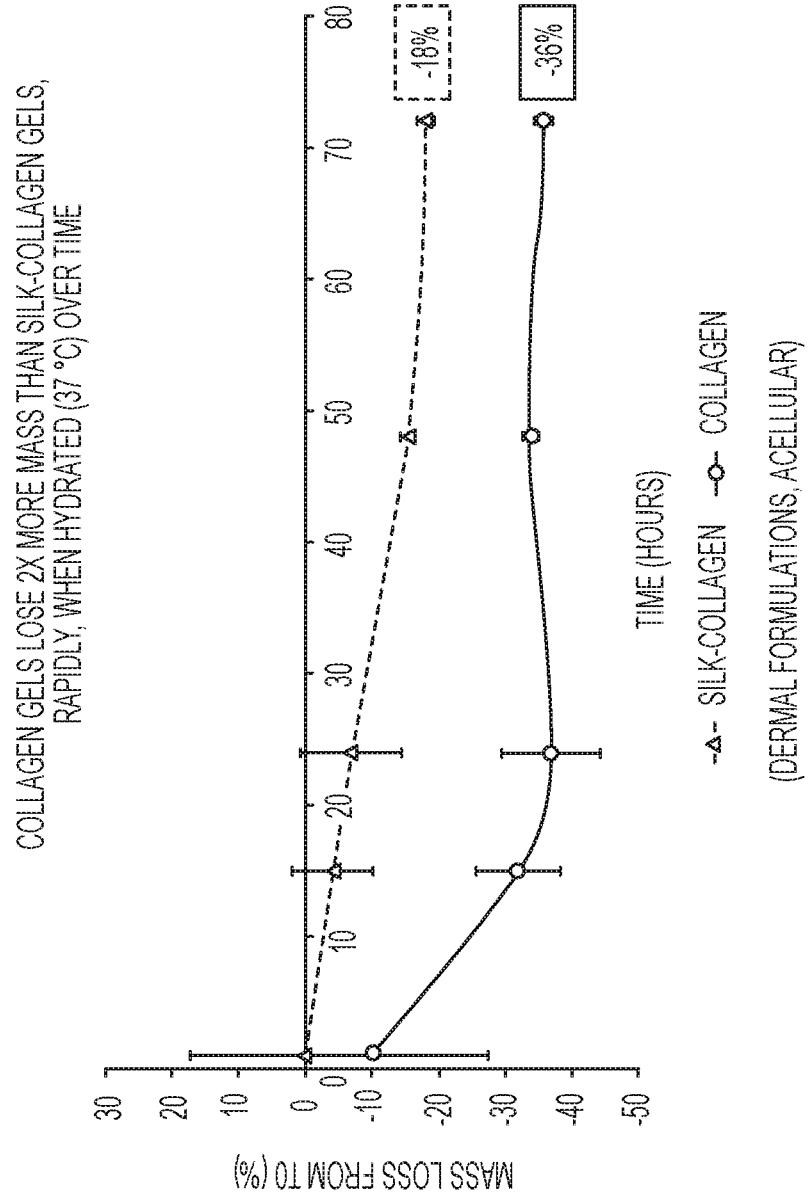
FIG. 42 shows an exemplary graph of mass loss of collagen scaffolds vs silk-collagen blend scaffolds over time in hours.

As is shown in FIG. 42, collagen only scaffolds lost more than two times the mass lost by silk-collagen blends. Accordingly, it is likely that silk-collagen blends may provide for more robust and stable compositions.

Figure 43:
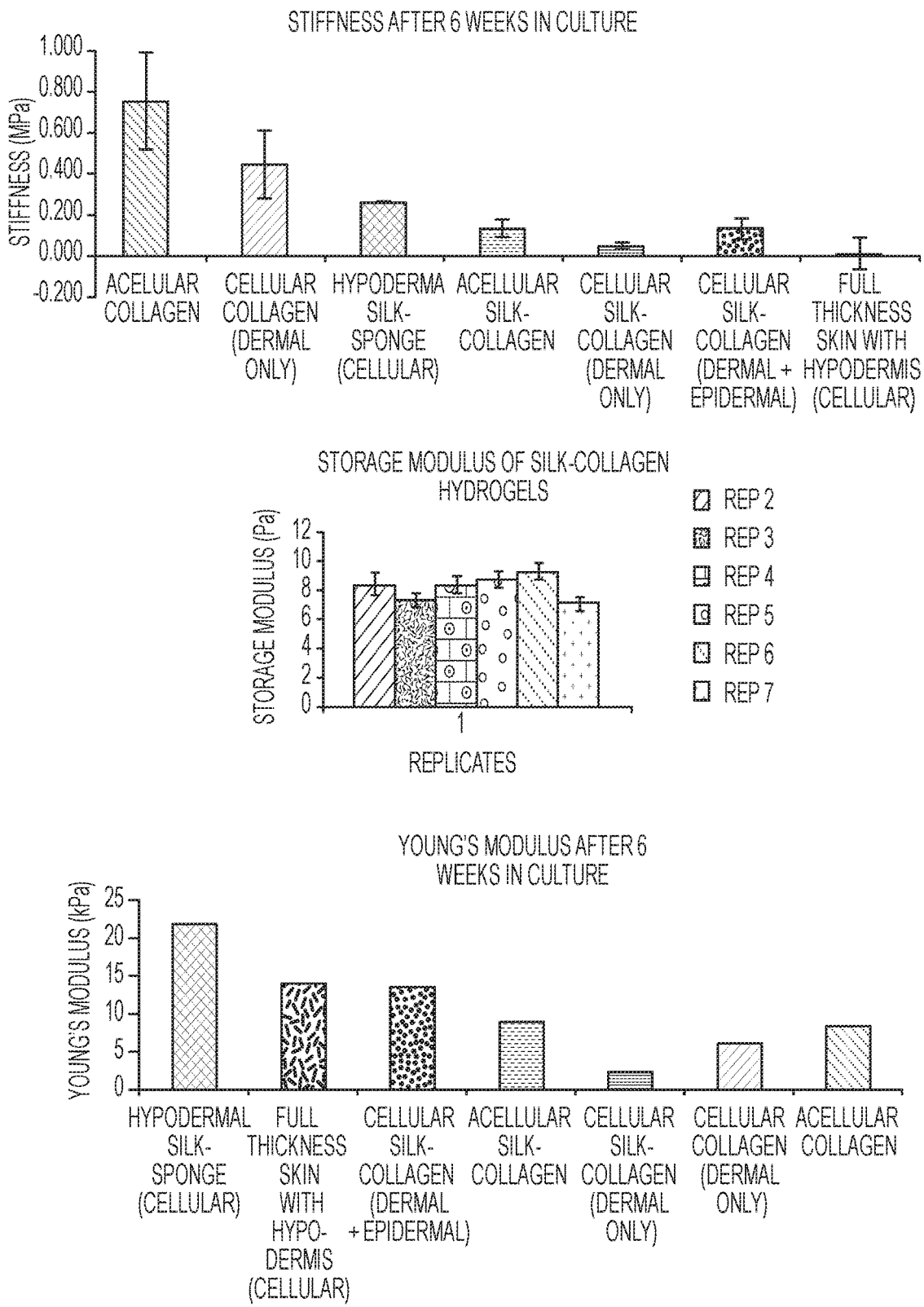
FIG. 43 shows exemplary graphs describing the stiffness, Young's modulus, and storage modulus of certain provided compositions.

FIG. 43 shows comparisons of the stiffness and Young's modulus of scaffolds of various composition including collagen only, silk only, and blends thereof. Generally, silk-collagen blends exhibited a lower degree of stiffness than collagen only scaffolds. Also shown in FIG. 43 is the storage modulus of several representative silk collagen scaffolds. Accordingly, the lower degree of stiffness observed for silk-collagen blend compositions better resemble the mechanical properties of native human skin that the stiffer collagen only based systems.

Figure 44:
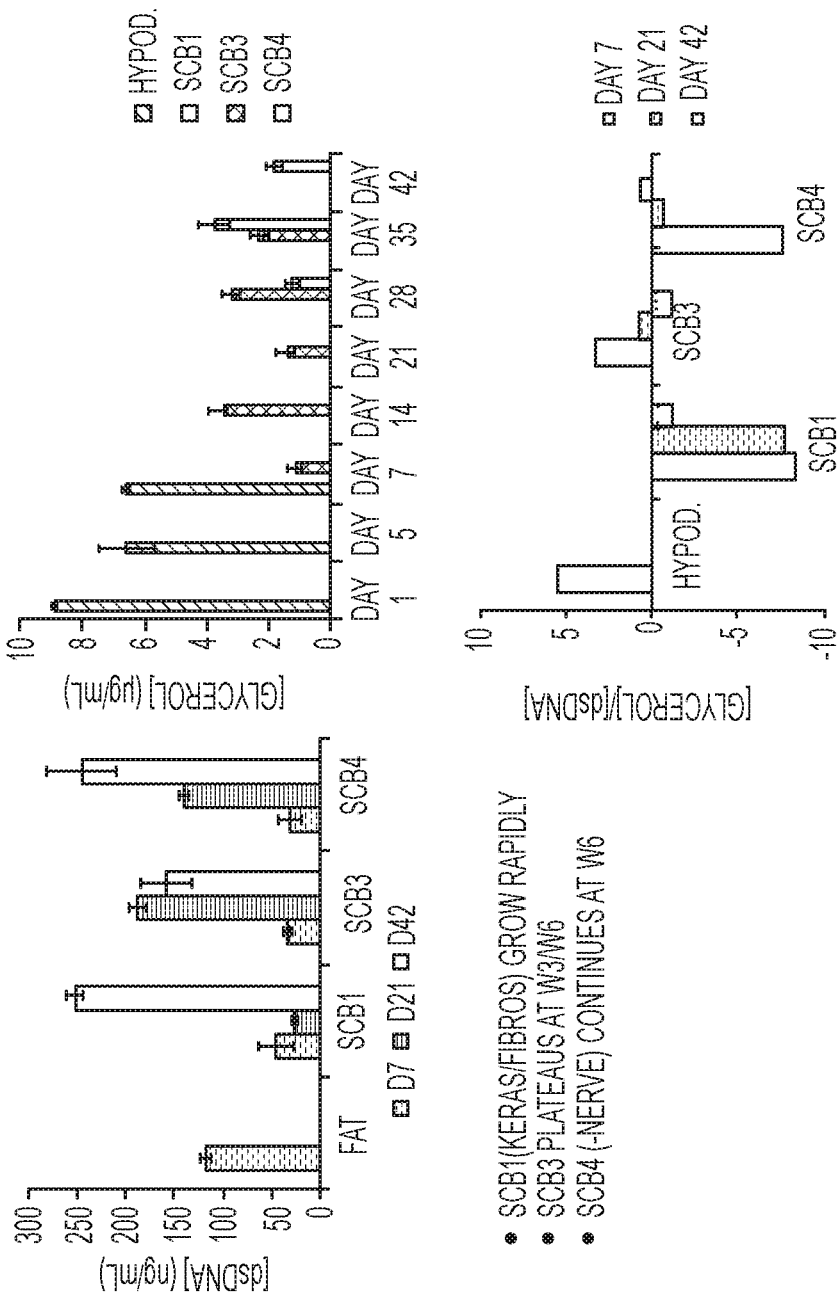
FIG. 44 shows exemplary graphs of double stranded DNA (dsDNA) content and glycerol secretion over up to 6 weeks of growth for certain provided compositions.

FIG. 44 shows the amount of glycerol secretion of time for each of a hypodermis control, SCB1, SCB3, and SCB4 compositions both in raw data and as a function of the dsDNA in the sample. Unsurprisingly, the SCB1 compositions which lack a hypodermis component exhibited no glycerol secretion over the time periods tested. SCB3 compositions exhibited glycerol secretion over five weeks of testing, while the SCB4 compositions did not exhibit glycerol secretion until the four week timepoint.

EQUIVALENTS AND SCOPE

While the present invention has been described herein in conjunction with various embodiments and examples, it is not intended that the scope be limited to such embodiments or examples. On the contrary, the present invention encompasses various alternatives, modifications, and equivalents, as will be appreciated by those of skill in the art. Accordingly, the descriptions, methods and diagrams of should not be read as limited to the described order of elements unless stated to that effect.

We claim:

1. A multi-layer silk composition comprising
   a first layer comprising silk fibroin and keratinocytes;
   a second layer comprising silk fibroin and fibroblasts;
   a third layer comprising silk fibroin and adipocytes; and
   a plurality of nervous system cells,
wherein at least some of the plurality of nervous system cells span at least two layers.

2. The composition of claim 1, wherein all of the cells in each of the first, second and third layers are human cells.

3. The composition of claim 2, wherein the human cells are primary cells or cell lines.

4. The composition of claim 1, wherein the nervous systems cells comprise at least one of neurons, glia, and neural stem cells.

5. The composition of claim 1, wherein at least a plurality of the nervous system cells are functional.

6. The composition of claim 1, further comprising a plurality of at least one type of immune cells.

7. The composition of claim 6, wherein the at least one type of immune cells includes macrophages.

8. The composition of claim 1, further comprising a plurality of at least one type of endothelial cell.

9. The composition of claim 8, wherein the endothelial cells comprise a monolayer.

10. The composition of claim 1, further comprising an electrical device that is functionally connected to at least some of the plurality nervous system cells.

11. The composition of claim 10, wherein activation of the electrical device results in the firing of one or more neurons.

12. The composition of claim 10, wherein the electrical device comprises at least one electrode.

13. The composition of claim 10, wherein the electrical device comprises silk fibroin.

14. The composition of claim 1, further comprising at least one of collagen, laminin, fibronectin, hyaluronic acid, fibrinogen, sulfated glycosaminoglycans, and/or one or more growth factors, in at least one layer.

15. The composition of claim 14, wherein the one or more growth factors comprise epidermal growth factor, fibroblast growth factor, nerve growth factor, platelet-derived growth actor, insulin-like growth factor, or tumor necrosis factor-β, and combinations thereof.

16. The composition of claim 1, wherein at least one layer is exposed to an air-liquid interface.

17. The composition of claim 1, wherein the third layer comprises lipoaspirate.

18. A method of making a multi-layer silk composition comprising
- providing a first layer comprising silk fibroin and keratinocytes;
- providing a second layer comprising silk fibroin and fibroblasts;
- providing a third layer comprising silk fibroin and adipocytes;
- providing a plurality of nervous system cells; and
- associating the first layer, second layer, third layer, and plurality of nervous system cells to form a multi-layer silk composition, wherein at least some of the plurality of nervous system cells span at least two layers.

19. A method comprising
a) providing a multi-layer silk composition comprising a first layer, a second layer, a third layer, and a plurality of nervous system cells, the first layer comprising silk fibroin and keratinocytes, the second layer comprising silk fibroin and fibroblasts, the third layer comprising silk fibroin and adipocytes, wherein at least some of the plurality of nervous system cells span at least two layers, wherein at least some of the cells in the composition are cancer cells;
b) exposing the composition to one or more therapeutic agents and/or inflammatory agents; and
c) characterizing the response of the cells in the composition to the one or more therapeutic agents.

20. The method of claim 19, wherein the one or more therapeutics agents comprise at least one cancer therapeutic agent.

\* \* \* \* \*